United States Patent
Chaudhuri et al.

(10) Patent No.: US 10,350,280 B2
(45) Date of Patent: Jul. 16, 2019

(54) METHODS TO ANALYZE GENETIC ALTERATIONS IN CANCER TO IDENTIFY THERAPEUTIC PEPTIDE VACCINES AND KITS THEREFORE

(71) Applicant: MedGenome Inc., Foster City, CA (US)

(72) Inventors: Amitabha Chaudhuri, Redwood City, CA (US); Ravi Gupta, Bangalore (IN); Priyanka Shah, Uttar Pradesh (IN); Malini Manoharan, Bangalore (IN); Kiran V. Paul, Kerala (IN); Rohit Gupta, Bangalore (IN)

(73) Assignee: MedGenome Inc., Foster City, CA (US)

( * ) Notice: Subject to any disclaimer, the term of this patent is extended or adjusted under 35 U.S.C. 154(b) by 0 days.

(21) Appl. No.: 15/791,301

(22) Filed: Oct. 23, 2017

(65) Prior Publication Data

US 2018/0085447 A1   Mar. 29, 2018

Related U.S. Application Data

(63) Continuation of application No. PCT/US2017/004773, filed on Aug. 31, 2017.

(60) Provisional application No. 62/382,179, filed on Aug. 31, 2016.

(51) Int. Cl.

| *C07K 4/00* | (2006.01) |
| *A61K 39/00* | (2006.01) |
| *C12Q 1/6886* | (2018.01) |
| *G16B 20/00* | (2019.01) |
| *G16B 35/00* | (2019.01) |
| *G16C 20/60* | (2019.01) |

(52) U.S. Cl.
CPC ........ *A61K 39/0011* (2013.01); *C12Q 1/6886* (2013.01); *G16B 20/00* (2019.02); *G16B 35/00* (2019.02); *G16C 20/60* (2019.02); *A61K 2039/5154* (2013.01); *A61K 2039/5158* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| 9,115,402 B2 | 8/2015 | Hacohen et al. |
| 2015/0133321 A1 | 5/2015 | Bhaumik et al. |
| 2016/0090417 A1 | 3/2016 | Cogswell et al. |
| 2016/0101170 A1 | 4/2016 | Hacohen et al. |
| 2016/0125129 A1 | 5/2016 | Sahin et al. |
| 2016/0177396 A1 | 6/2016 | Rabbani et al. |

FOREIGN PATENT DOCUMENTS

| WO | WO 2004/016799 A2 | * | 2/2004 |
| WO | WO 2014/168874 A2 |   | 10/2014 |
| WO | WO 2014/180569 A1 | * | 11/2014 |
| WO | WO 2014/166874 A3 |   | 12/2014 |
| WO | WO 2016/040682 A1 |   | 3/2016 |

OTHER PUBLICATIONS

Nielson et al (PLOS One, 2007, 8(e796): 1-10).*
Doytchinova et al (J Med Chem, 2006, 49: 2193-2199).*
Chowell et al (PNAS, 2015, 112(14): E1754-62).*
DeLisi et al (PNAS, 1985, 82: 7048-7052).*
Margalit et al (J Immunol, 1987, 138: 2213-2229).*
Schumacher, T.N. and R.D. Schreiber, Neoantigens in cancer immunotherapy. Science, 2015. 348(6230): p. 69-74 (Exhibit 1).
Gubin, M.M., et al., Tumor neoantigens: building a framework for personalized cancer immunotherapy. J Clin Invest, 2015. 125(9): p. 3413-21. (Exhibit 2).
Van der Burg, S.H., et al., Vaccines for established cancer: overcoming the challenges posed by immune evasion. Nat Rev Cancer, 2016. 16(4): p. 219-33. (Exhibit 3).
Romero, P., et al., The Human Vaccines Project: A roadmap for cancer vaccine development. Sci Transl Med, 2016. 8(334): p. 334ps9. (Exhibit 4).
Yadav, M., et al., Predicting immunogenic tumour mutations by combining mass spectrometry and exome sequencing. Nature, 2014. 515(7528): p. 572-6. (Exhibit 5).
Vaughan, K., et al., Deciphering the MHC-associated peptidome: a review of naturally processed ligand data. Expert Rev Proteomics, 2017: p. 1-8. (Exhibit 6).
Wieczorek, M., et al., Major Histocompatibility Complex (MHC) Class I and MHC Class II Proteins: Conformational Plasticity in Antigen Presentation. Front Immunol, 2017. 8: p. 292. (Exhibit 7).
Basler, M., C.J. Kirk, and M. Groettrup, The immunoproteasome in antigen processing and other immunological functions. Curr Opin Immunol, 2013. 25(1): p. 74-80. (Exhibit 8).
Eggensperger, S. and R. Tampe, The transporter associated with antigen processing: a key player in adaptive immunity. Biol Chem, 2015. 396(9-10): p. 1059-72. (Exhibit 9).
Mahmutefendic, H., et al., Endosomal trafficking of open Major Histocompatibility Class I conformers—implications for presentation of endocytosed antigens. Mol Immunol, 2013. 55(2): p. 149-52. (Exhibit 10).
Roche, P.A. and K. Furuta, The ins and outs of MHC class II-mediated antigen processing and presentation. Nat Rev Immunol, 2015. 15(4): p. 203-16. (Exhibit 11).
Neefjes, J., et al., Towards a systems understanding of MHC class I and MHC class II antigen presentation. Nat Rev Immunol, 2011. 11(12): p. 823-36. (Exhibit 12).
Leavy, O., Antigen presentation: cross-dress to impress. Nat Rev Immunol, 2011. 11(5): p. 302-3. (Exhibit 13).

(Continued)

*Primary Examiner* — Sean E Aeder
(74) *Attorney, Agent, or Firm* — Adriano & Associates

(57) ABSTRACT

The invention describes a method for identifying T-cell activating neo-epitopes from all genetically altered proteins. The mutated proteins contribute to neo-epitopes after they are proteolytically degraded within antigen presenting cells, such as dendritic cells and macrophages.

24 Claims, 9 Drawing Sheets

Specification includes a Sequence Listing.

(56) References Cited

OTHER PUBLICATIONS

Joffre, O.P., et al., Cross-presentation by dendritic cells. Nat Rev Immunol, 2012. 12(8): p. 557-69. (Exhibit 14).
Branca, M.A., Rekindling cancer vaccines. Nat Biotechnol, 2016. 34(10): p. 1019-1024. (Exhibit 15).
Ott, P.A., et al., An immunogenic personal neoantigen vaccine for patients with melanoma. Nature, 2017. 547(7662): p. 217-221. (Exhibit 16).
Sahin, U., et al., Personalized RNA mutanome vaccines mobilize poly-specific therapeutic immunity against cancer. Nature, 2017. 547(7662): p. 222-226. (Exhibit 17).
Carreno, B.M. And E.R. Mardis, A Vaccine for Cancer? Sci Am, 2016. 314(4): p. 46. (Exhibit 18).
Carreno, B.M., et al., Cancer immunotherapy. A dendritic cell vaccine increases the breadth and diversity of melanoma neoantigen-specific T cells. Science, 2015. 348(6236): p. 803-8. (Exhibit 19).
Liu, X.S. and E.R. Mardis, Applications of Immunogenomics to Cancer. Cell, 2017. 168(4): p. 600-612. (Exhibit 20).
Hundal, J., et al., Cancer Immunogenomics: Computational Neoantigen Identification and Vaccine Design. Cold Spring Harb Symp Quant Biol, 2016. 81: p. 105-111. (Exhibit 21).
Turajlic, S., et al., Insertion-and-deletion-derived tumour-specific neoantigens and the immunogenic phenotype: a pan-cancer analysis. Lancet Oncol, 2017. 18(8): p. 1009-1021. (Exhibit 22).
Romero Arenas, M.A., et al., Preliminary whole-exome sequencing reveals mutations that imply common tumorigenicity pathways in multiple endocrine neoplasia type 1 patients. Surgery, 2014. 156(6): p. 1351-7; discussion 1357-8. (Exhibit 23).
Karosiene, E., et al., NetMHCcons: a consensus method for the major histocompatibility complex class I predictions. Immunogenetics, 2012. 64(3): p. 177-86. (Exhibit 24).
Nielsen, M., et al., The role of the proteasome in generating cytotoxic T-cell epitopes: insights obtained from improved predictions of proteasomal cleavage. Immunogenetics, 2005. 57(1-2): p. 33-41. (Exhibit 25).
Hall, M.A., Correlation-based Feature Selection for Machine Learning. 1999. (Exhibit 26).
Sidney, J., et al., HLA class I supertypes: a revised and updated classification. BMC Immunol, 2008. 9: p. 1. (Exhibit 27).
Greenbaum, J., et al., Functional classification of class II human leukocyte antigen (HLA) molecules reveals seven different supertypes and a surprising degree of repertoire sharing across supertypes. Immunogenetics, 2011. 63(6): p. 325-35. (Exhibit 28).
Invitation to Pay Additional Fees and, Where Applicable, Protest Fee, dated Dec. 8, 2017, issued in connection with the corresponding PCT application, PCT/US17/49773 (Exhibit 30).
International Search Report and Written Opinion of the International Searching Authority dated Jan. 31, 2018—Exhibit 31 (provided herein).
Parker Kenneth C. et al, Scheme for Ranking Potential HLA-A2 Binding Peptides Based on Independent Binding of Individual Peptide Side-Chains, *Journal of Immunology*, Jan. 1994, vol. 152 No. 1, pp. 163-175—Exhibit 32 (provided herein).
Nakashima, Hiroshi & Nishikawa, Ken. (1992). The amino acid composition is different between the cytoplasmic and extracellular sides in membrane proteins. Federation of European Biochemical Societies (FEBS). vol. 303, No. 2,3, 141-146 (Exhibit 37).
Kakraba, Samuel & Knisley, Debra. (2016). A graph-theoretic model of single point mutations in the cystic fibrosis transmembrane conductane regulator. Journal of Advances in Biotechnology. vol. 6, No. 1, 780-786. 10.24297/jbt.v6i1.4013. (Exhibit 38).
Bull, Henry B. & Breese, Keith. (1974). Surface Tension of Amino Acid Solutions: A Hydrophobicity Scale of the Amino Acid Residues. Archives of Biochemistry and Biophysics 161, 665-670 (1974) (Exhibit 39).
Bundi, Arno & Wuthrich, Kurt. (1979). H-NMR Parameters of the Common Amino Acid Residues Measured in Aqueous Solutions of the Linear Tetrapeptides H-Gly-Gly-X-L-Ala-OH. Biopolymers, vol. 18, 285-297 (1979) (Exhibit 40).

Cedano, Juan et al. (1997). Relation Between Amino Acid Composition and Cellular Location of Proteins. J. Mol. Biol. (1997) 266, 594-600 (Exhibit 41).
Charton, Marvin & Charton, Barbara I. The Dependence of the Chou-Fasman Parameters on Amino Acid Side Chain Structure. J. theor. Biol. (1983) 102, 121-134 (Exhibit 42).
Cid, Hilda et al. Hydrophobicity and structural classes in proteins. Protein Engineering vol. 5 No. 5 pp. 373-375. 1992 (Exhibit 43).
Geisow. Michael J. & Roberts, Robin D. B. Amino acid preferences for secondary structure vary with protein class. Int. J. Biol. Macromol., 1980, vol. 2, 387-389 (Exhibit 44).
Jones, Daniel D. Amino Acid Properties and Side-chain Orientation in Proteins: A Cross Correlation Approach. J. theor. Biol. (1975) 50, 167-183 (Exhibit 45).
Kanehisa, Minoru I. & Tsong Tian Yow. Local Hydrophobicity Stabilizes Secondary Structures in Proteins. Biopolymers, vol. 19, 1617-1628 (1980) (Exhibit 46).
Levitt, Michael. Conformational Preferences of Amino Acids in Globular Proteins. Biochemistry 1978, 17, 20, 4277-4285 (Exhibit 47).
Maxfieldi, Frederick R. & Scheraga, Harold A. Status of Empirical Methods for the Prediction of Protein Backbone Topography. Biochemistry 1976, vol. 15, No. 23, 5138-5153 (Exhibit 48).
Nakashima, Hiroshi et al. Distinct Character in Hydrophobicity of Amino Acid Compositions of Mitochondrial Proteins. Proteins: Structure, Function, and Genetics 8:173-178 (1990) (Exhibit 49).
Palau, Jaume, et al. Protein secondary structure Studies on the limits of prediction accuracy. Int. J. Peptide Protein Res. 19,1982,394-401 (Exhibit 50).
Yutani, Katsuhide, et al. Dependence of conformational stability on hydrophobicity of the amino acid residue in a series of variant proteins substituted at a unique position of tryptophan synthase α subunit. Proc. Natl. Acad. Sci. USA vol. 84, pp. 4441-4444, Jul. 1987 Biochemistry (Exhibit 51).
Meek, James L., Prediction of peptide retention times in high-pressure liquid chromatography on the basis of amino acid composition. Proc. Natl. Acad. Sci. USA vol. 77, No. 3, pp. 1632-1636, Mar. 1980 Medical Sciences (Exhibit 52).
Ponnuswamy, P.K. Hydrophobic Packing and Spatial Arrangement of Amino Acid Residues in Globular Proteins. Biochimica et Biophysica Acta, 623 (1980) 301-316 (Exhibit 53).
Qian, Ning & Sejnowski, Terrence J. Predicting the Secondary Structure of Globular Proteins Using Neural Network Models. J. Mol. Biol. (1988) 202, 865-884 (Exhibit 54).
Radzicka, Anna & Wolfenden, Richard. Comparing the Polarities of the Amino Acids: Side-Chain Distribution Coefficients between the Vapor Phase, Cyclohexane, 1-0ctano1, and Neutral Aqueous Solution. Biochemistry 1988, 27, 1664-1670 (Exhibit 55).
Richardson, Jane S. & and Richardson, David C. Amino Acid Preferences for Specific Locations at the Ends of α Helices. Science 1988, vol. 240, 1648-1652 (Exhibit 56).
Robson, B. & Suzuki, E. Conformational Properties of Amino Acid Residues in Globular Proteins. J. Mol. Biol. (1976) 107, 327-356 (Exhibit 57).
Kidera, Akinori, et al. Statistical Analysis of the Physical Properties of the 20 Naturally Occurring Amino Acids. Journal of Protein Chemistry, vol. 4, No. 1, 1985 (Exhibit 58).
Sueki, M. et al. Helix-Coil Stability Constants for the Naturally Occurring Amino Acids in Water. 22. Histidine Parameters from Random Poly[(hydroxybutyl)glutamine-co-L-histidine]. Macromolecules 1984,17, 148-155 (Exhibit 59).
Suyama, Mikita & Ohara,Osamu. DomCut: prediction of inter-domain linker regions in amino acid sequences. Bioinformatics Applications Note, vol. 19 No. 5 2003, pp. 673-674 DOI: 10.1093/bioinformatics/btg031 (Exhibit 60).
Tanaka, Seiji & Scheraga, Harold A. Statistical Mechanical Treatment of Protein Conformation. 5. A Multistate Model for Specific-Sequence Copolymers of Amino Acids. Macromolecules. Jan.-Feb. 1977;10(1):9-20 (Exhibit 61).
Vasquez, Max et al. Computed Conformational States of the 20 Naturally Occurring Amino Acid Residues and of the Prototype Residue α-Aminobutyric Acid. Macromolecules 1983,16, 1043-1049 (Exhibit 62).

(56) References Cited

OTHER PUBLICATIONS

Wilce, Mathew C. J. Physicochemical Basis of Amino Acid Hydrophobicity Scales: Evaluation of Four New Scales of Amino Acid Hydrophobicity Coefficients Derived from RP-HPLC of Peptides. Anal. Chem. 1995,67, 1210-1219 (Exhibit 63).

Zaslavsky, B. Yu. et al. Measurement of Relative Hydrophobicity of Amino Acid Side-Chains by Partition in an Aqueous Two-Phase Polymeric System: Hydrophobicity Scale for Non-Polar and Ionogenic Side-Chains. Journal of Chromatography, 240(1982) 21-28 (Exhibit 64).

Chou, Peter Y. & Fasman, Gerald D. Prediction of the Secondary Structure of Proteins From Their Amino Acid Sequence. Advances in Enzymology and Related Areas of Molecular Biology, vol. 47, 45-148 (Exhibit 65).

Mitaku, Shigeki et al. Amphiphilicity index of polar amino acids as an aid in the characterization of amino acid preference at membrane-water interfaces. Bioinformatics, vol. 18, pp. 608-616 (2002) (Exhibit 66).

Rackovsky, S. & Scheraga, H. A. Differential Geometry and Polymer Conformation. 4. Conformational and nucleation properties of individual amino acids. Macromolecules 15, 1340-1346 (1982) (Exhibit 67).

Stanton, David T. & Jurs, Peter C. Development and Use of Charged Partial Surface Area Structural Descriptors in Computer-Assisted Quantitative Structure-Property Relationship Studies. Anal. Chem. 1990, 62, 2323-2329 (Exhibit 68).

Wang. Renxiao et al. Calculating partition coefficient by atom-additive method. Perspectives in Drug Discovery and Design, 19 47-66, 2000. (Exhibit 69).

\* cited by examiner

Figure 1. Steps to identify immunogenic peptides from cancer tissues

Figure 2. Steps for the creation of classification models for predicting TCR-binding peptides derived from normal and cancer tissues.

Fig. 3 a-b. (a) Binding affinity distribution of immunogenic and non-immunogenic peptides, (b) Distribution of peptide with >= 500nM and < 500nM.

Figure 4. A schematic of the steps used for creating the classification models to separate TCR-binding peptides (immunogenic) from those that did not bind TCR (non-immunogenic)

Fig. 5 a-b. (a) Sensitivity and specificity of the 500 training/test instances using J4.8 classification approach, (b) ROC curve from the ensemble classifier.

Fig. 6 a-b. (a) Sensitivity and specificity of the 433 classifier instances using J4.8 classification approach, (b) The ROC curve for the 433 classifiers (colored in RED), 45 classifiers (colored in Blue).

Figure 7 a-c. Features to identify selected peptides. (a) Number of features that define occupancy of amino acids at each position of the 9-mer peptide. (b) Number of features that define hydrophobicity and helix/turn properties of amino acids. (c) Enrichment of amino acids with helix-turn and hydrophobicity properties at each position of the 9-mer peptides.

METHODS TO ANALYZE GENETIC ALTERATIONS IN CANCER TO IDENTIFY THERAPEUTIC PEPTIDE VACCINES AND KITS THEREFORE

CROSS REFERENCE TO RELATED APPLICATIONS

The subject application claims priority under 35 U.S.C. 111(a) to PCT Application No. PCT/US2017/049773, filed Aug. 31, 2017, which claims the benefit of U.S. Provisional Application No. 62/382,179 filed Aug. 31, 2016, all of which are incorporated herein by reference in their entireties into the present patent application for all purposes.

FIELD OF THE DISCLOSURE

The present disclosure is directed to methods of identifying immunogenic mutant peptides having therapeutic utility as cancer vaccines

BACKGROUND OF THE INVENTION

Genetic alterations are detected in all tumor cells. These alterations, occurring at the level of DNA, are transcribed and translated to generate altered proteins that in many instances drive cancer. These altered proteins can sometime contribute to immune recognition by T and B cells evoking activation of the immune response, which can lead to the elimination of tumor cells expressing the altered proteins [1-3].

Tumor cells, including malignant tumor cells or cancer cells, accumulate a large number of somatic mutations, from as low as ten, to as high as thousands depending on the cancer type. Only a subset of these mutations can evoke an immune response. Identifying such mutations can lead to the generation of therapeutic vaccines that can be given to patient as a polypeptide or as nucleic acids (both DNA and RNA) [4].

For a mutation to be recognized as foreign, the mutant amino acid should be present as part of a peptide that binds class I or class II major histocompatibility complex (MHC or alternatively known as human leukocyte antigen or HLA in human) molecules and be presented on the surface of antigen presenting cells (professional APCs). The MHC- or HLA-bound peptide interacts with the T-cell receptor (TCR) expressed on the surface of T cells. Productive binding with the TCR activates T-cells, which can kill tumor cells directly through its cytolytic activity (CD8+ cytotoxic T-cells) or perform helper function (CD4+ helper T-cells) to induce antibody production. In this context, the definition of an immunogenic peptide is restricted to peptides that can interact with $CD8^+$ or $CD4^+$ T cells. For the interaction to happen, the peptide must be presented on the surface of cells in complex with MHC or HLA class I or class II proteins. The MHC class I- or HLA class I-bound peptide interacts with $CD8^+$ T cells, and the MHC class II- or HLA class II-bound peptide interacts with $CD4^+$ T cells. Although MHC or HLA binding and surface presentation is required for T cell activation, but, the displayed peptide bound to MHC or HLA proteins on the surface of cell is necessary but not sufficient for T cell activation as TCR must also interact with the displayed peptide. Most peptides presented on the cell surface in complex with MHC or HLA fail to engage T cells and therefore are not immunogenic [5]. Immunogenicity require not only peptide-binding and display by MHC class I or class II proteins but also binding of the MHC class I or class II-displayed peptide by TCR of the CD8+ T-cell or CD4+ T-cell, respectively [6]. While much is known about the rules governing peptide binding by MHC or HLA molecules, little is known about the rules governing peptide binding by TCR, other than that the rules governing peptide binding by TCR are different from peptide binding by MHC or HLA proteins.

Class I HLA proteins are encoded by HLA-A, HLA-B and HLA-C genes. These proteins bind peptides of 8-11 amino acids in length, with the preferred length being 9 amino acids long. The peptide binding groove of class HLA is formed by two alpha helices supported by an anti-parallel beta sheet. The peptide-binding groove is deeper compared to class II HLA molecules and requires residues to be projected outside the binding groove to make interactions with the TCR [7].

Peptides bind to class HLA molecules in a multistep process. The steps are as follows: 1) generation of protein fragments by immunoproteasomal or proteasomal processing as part of the natural turnover of proteins in cells [8]; 2) Entry of the protein fragment into the lumen of the endoplasmic reticulum by binding to peptide transporters (TAP) [9]; 3) Binding to the peptide-binding groove of the class I HLA molecules; 4) Transport through vesicles to the cell surface and 5) presentation on the surface of cells [10] [11].

In the case of endogenous proteins, such as altered proteins in tumor or cancer cells, these proteins being produced intracellularly by the cell do not require cellular uptake. As such, peptides derived by immunoproteasomal or proteasomal processing as part of the natural turnover of proteins in cells may be displayed by class I MHC or HLA molecules in all cell types in which the altered protein is expressed by the cell. In contrast, in the case of a peptide used in tumor or cancer vaccine, the peptide is exogenous to the cell and must be taken up by professional antigen-presenting cells in a process called cross-presentation in order to be displayed by class I MHC or HLA proteins [12-14]. The peptide used in tumor or cancer vaccine is longer than the peptide displayed by class I MHC or HLA proteins, as the peptide is taken up by the cell and undergo proteolysis to produce shorter peptide(s). Equal number of amino acids are added to the amino- and carboxy-termini, so as to extend the length of the final peptide displayed by class I MHC or HLA proteins. Typically, five to eighteen amino acids are added to each end of the 8-11 amino acid long peptide displayed on cell surface by class I MHC or HLA proteins, such that the peptide formulated in the tumor or cancer vaccine is approximately 18 to 47 amino acids in length. The upper limit of peptide length in tumor or cancer vaccine is less than or equal to 50 amino acids. The antigen-presenting cells capable of cross presentation are professional antigen-presenting cells and include dendritic cells (primarily), macrophages, and B lymphocytes.

The binding of MHC-peptide complex to the $CD8^+$ T cells, henceforth referred to as cytolytic or cytotoxic T cells (CTLs) activates a series of signaling pathways in CTLs resulting in their expansion to generate a population of effector CTLs. These CTLs will recognize tumor cells displaying the mutant peptide on their surface and kill them by apoptosis. Therefore, peptides derived from cancer mutations that are capable of mounting a CTL response can be used as cancer vaccines for treating cancer patients [15].

Two studies have demonstrated that immunogenic peptides can provide long term benefit to cancer patients when used as monotherapy [16, 17]. Therefore, accurate identification of immunogenic peptides from tumor-derived mutant protein can provide an avenue of treatment for cancer patients [18] [19]. However, the lack of efficient method for identifying bonafide immunogenic peptides have not only increased the cost of vaccination, but also increased the uncertainty of whether the vaccine will deliver the desired effect of inducing an anti-tumor response.

Next generation sequencing technology can catalogue all tumor mutations from a patient's tumor cells rapidly. However, identifying immunogenic peptides derived from such mutations is still a formidable challenge. The challenge comes from the fact that accurate methods of selecting immunogenic peptides from a pool of immunogenic and non-immunogenic peptides [20] [18].

Most screening platform uses HLA-binding prediction as a measure of immunogenicity [21]. The prediction can be further confirmed by actual detection of the peptide on the cell surface by mass spectrometry [5]. However, surface presentation of a peptide in complex with HLA is not an indication of immunogenicity. For a peptide to be immunogenic, the peptide presented on the surface of cells must engage T cell receptor. There is a need in the art for a high throughput methodology for prediction of immunogenic peptide for cancer therapy.

SUMMARY OF THE DISCLOSURE

The practice matter of the invention disclosed in this application has employed, unless otherwise indicated, computational prediction algorithms organized in a step-wise workflow to identify tumor or cancer vaccines from tumor-derived proteins, which are expressed and mutated or altered only in cancer cells. The invention covers the identification of T-cell neo-epitopes from four classes of genetically altered proteins—i) proteins altered in amino acid sequence in which one or more amino acids are altered or mutated, which may be arranged in a sequence or distributed randomly across the length of the protein; ii) proteins produced from genes with internal insertion or deletion in the coding sequence; iii) proteins translated from fusion genes; and iv) proteins produced from splice variants.

Selection of immunogenic peptides comprises: a) selecting a set of cancer variants from mouse and human cancer cell lines and mouse and human cancer tissues where each variant in the genomic sequence correspond to both protein coding and protein non-coding sequences; b) variants of mouse cell lines and cancer tissues are identified by mouse whole exome and/or whole genome sequencing and variants from human cancer cell lines and human cancer tissues are identified by whole exome and/or whole genome sequencing; c) variants in mouse tissues and cell lines are identified by comparing with the reference sequence of mouse, and variants in human tissues and cell lines are identified by comparing with the reference sequence of human; d) variants are identified by comparing with the reference sequence, where the reference sequence is mouse reference sequence available in the public domain, or human reference sequence available in the public domain (e.g., current mouse reference sequence is (GRCm38/mm10) and current human reference sequence is (hg19)); e) variants from mouse tissues and cell lines include all genomic variants that alter the sequence of the RNA and the sequence of the protein translated from the RNA; f) variants from human tissues and cell lines include all genomic variants that alter the sequence of the proteins translated from the messenger RNA—protein variants; g) selecting the variants based on their expression in the mouse or human cell lines and tissues from the transcriptomic analysis; h) generating 8-11 amino acid peptides from the altered protein variants; and i) selecting a set of 8-11 amino acid immunogenic peptides from the previous step by predicting immunogenicity of the variant peptide comprising the altered amino acids encoded by the variant coding sequence; thereby selecting immunogenic peptides from altered or mutated proteins unique to cancer or tumor cells or tissues.

In some embodiments, according to any of the methods described above, the method further comprises selecting peptides that bind T cells by engaging with the T cell receptor (TCR) by obtaining peptides that carry features of TCR binding. Steps include one or more of: a) determining features associated with each of the amino acids in a 9-mer peptide; b) determining features that are unique or shared between amino acids that make up the composition of the 9-mer peptide; c) determining features that favor interactions between TCR and the HLA-bound peptide, comprising amino acid positions 3-8 of the 9-mer peptide; d) determining features that favor HLA binding comprising amino acid positions 1-2 and 9 of the 9-mer peptide; e) determining features that are different between the non-mutated and the mutated peptide; g) determining and/or applying features that select immunogenic peptides from a list of immunogenic and non-immunogenic peptides thereby identifying immunogenic peptides from altered proteins expressed in tumor or cancer cell lines and/or tissues.

According to any one of the methods described above immunogenic peptide is defined by a combination of one or more of the following parameters: i) peptide is derived from a gene which is mutated in the DNA from tumor or cancer cell but not in normal cell as determined by DNA sequencing; ii) the mutant gene is expressed in tumor or cancer and detected by transcriptome sequencing; iii) mutation changes one or more amino acids in the translated protein determined by in silico protein translation (conceptual translation of protein coding region or sequences) from the transcript encoding the mutant protein; iv) mutated or altered peptide derived from the mutant or altered protein binds TCR; v) affinity of mutated peptide to class I HLA or equivalent; vi) sensitivity of the peptide to processing by proteasomal and/or immunoproteasomal enzymes and vii) ability of the peptide to bind peptide transporter present on the endoplasmic reticulum. In some embodiments, predicting immunogenicity is further based on HLA-typing analysis.

The present application in another aspect also provides tumor-specific immunogenic peptides identified by any of the above methods or combination of methods from human tumor patients. In some embodiments, the composition comprises of two or more tumor specific immunogenic mutant peptides described herein. In some embodiments, the composition further comprises an adjuvant The present application in another aspect also provides cancer-specific immunogenic peptides identified by any of the above methods or combination of methods from human cancer patients. In some embodiments, the composition comprises of two or more cancer specific immunogenic mutant peptides described herein. In some embodiments, the composition further comprises an adjuvant The present application in yet another aspect provides a method of creating an immunogenic composition comprising at least one tumor or cancer specific mutant peptide or a larger precursor encoding the 8- to 11-mer mutant immunogenic peptide identified by any of the methods described herein. In one embodiment, the method of creating an immunogenic composition comprises at least one tumor specific mutant peptide or a larger precursor encoding the 9-mer immunogenic peptide identified by any of the methods described herein. In some embodiments, the immunogenic composition contains two or more immunogenic tumor-specific mutant peptides. In some embodiments, the immunogenic composition contains two or more immunogenic cancer-specific mutant peptides.

The present application also provides an immunogenic composition comprising at least one nucleic acid encoding tumor or cancer specific immunogenic peptide, or one nucleic acid encoding a larger precursor containing the 9-mer mutant immunogenic peptide identified by any of the methods described herein. In some embodiments, the immunogenic composition comprising a nucleic acid encoding two or more (up to about 20) tumor-specific mutant immunogenic peptides. In some embodiments, the immunogenic composition comprising a nucleic acid encoding two or more (up to about 20) cancer-specific mutant immunogenic peptides. In other embodiments, the immunogenic composition can be composed of a mixture of immunogenic peptides, or a DNA encoding one or more immunogenic peptides, or a RNA encoding one or more immunogenic peptides.

DETAILED DESCRIPTION OF THE INVENTION

Figure 1:
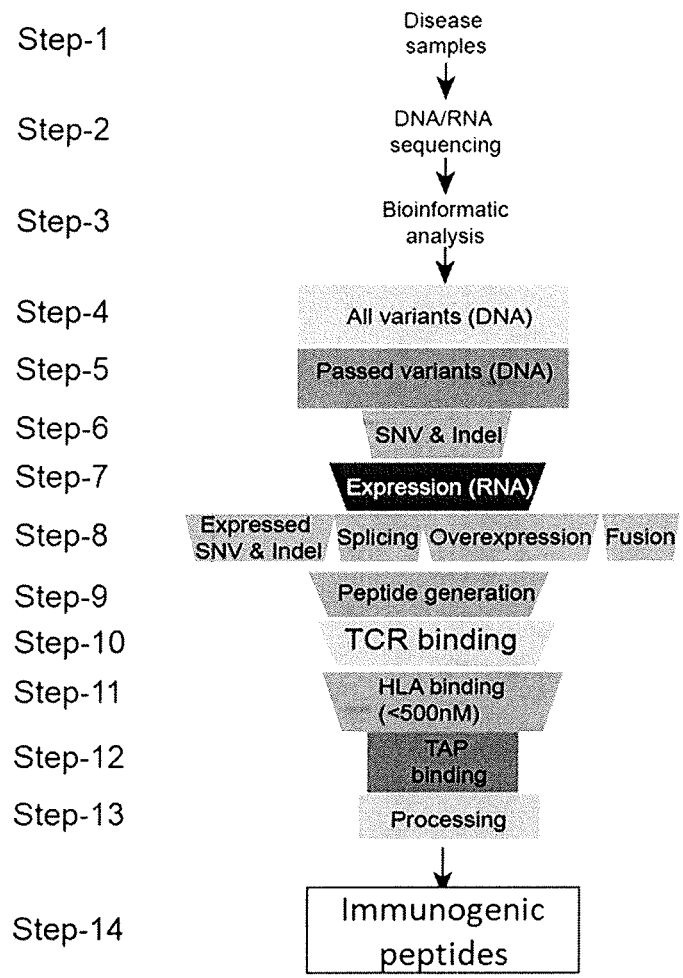
FIG. 1. Steps to identify immunogenic peptides from cancer tissues.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term "about." As used herein, the term "about" when used before a numerical designation, e.g., temperature, time, amount, concentration, and such other, including a range, indicates approximations which may vary by (+) or (−) 10%, 5% or 1%.

As used herein, the term "substantially free" includes being free of a given substance or cell type or nearly free of that substance or cell type, e.g. having less than about 1% of the given substance or cell type.

As used in this application, "cancer-specific mutant peptide" refers to a peptide that comprises at least one mutated amino acid present in the cancer tissue and absent in the normal tissue. The "cancer immunogenic peptide or tumor immunogenic peptide" refers to a peptide that comprises at least one mutated amino acid that is present in the cancer tissue and absent in the normal tissue and is capable of binding TCR and evoking a T cell response in the individual. The immunogenic peptides of the invention which are selected by the methods of the invention may be synthesized or expressed to be part of a larger polypeptide tumor vaccine. Alternatively, the nucleic acid encoding the immunogenic peptide of the invention may be used as part of a larger tumor vaccine. Cancer-tumor immunogenic peptides can arise from i) proteins altered in amino acid sequence in which one or more amino acids are altered, which may be arranged in a sequence or distributed randomly across the length of the protein; ii) proteins translated from fusion genes; iii) proteins produced from splice variants or from mutations in splicing sites, which results in the introduction of intronic region or part of an intronic region in frame with the protein coding sequence or exclusion of part or whole exon(s) resulting in an altered protein with new sequence at the site of the lost exonic region; iv) Proteins produced from insertions and/or deletions of nucleotides that cause frameshift in the protein coding sequence resulting in the introduction of one or more amino acids absent in the normal protein [22]; or vi) protein arising from loss of stop codons (stop loss) that adds additional amino acids at the end of the protein [23].

An "immunogenic peptide" in this application refers to a mutant peptide capable of transducing a signal CD4$^+$ and CD8$^+$ T cells. An "immunogenic peptide used as a vaccine" in this application refers to a longer peptide of length ranging from about >11-mer up to about 50-mer containing within the longer peptide the minimal sequence of the immunogenic peptide.

A "variant coding sequence" in this application refers to a nucleic acid sequence (DNA or RNA) from a cancer sample containing one or more variant nucleotides compared to the sequence in the reference normal sample. The sequence variation results in a change in the amino acid sequence of the protein encoded by the nucleic acid sequence.

The "expressed variant coding sequence" in this application refers to a nucleic acid sequence derived from RNA expressed in the tumor or cancer tissue of the individual.

A nucleic acid sequence "encoding" a peptide refers to a sequence of DNA or RNA containing the coding sequence of the peptide.

The "conceptual translation or in silico translation of the coding sequences" refers to translation of the coding sequence of a nucleic acid to amino acid sequence based on a codon table specifying amino acids, so as to obtain peptide or protein with a defined amino acid sequence. A computer and software may be used to perform the "conceptual translation or in silico translation of the coding sequences."

The "genetically altered protein(s) expressed by the mammalian tumor cell or the mammalian tumor tissue" refers to altered or mutated protein(s) reflective of changes in the genetic material present in the mammalian tumor cell or tissue.

The "class I HLA or equivalent" is class I MHC molecules of human or any other mammalian species.

The "HLA-binding neoepitope" in the context of class I HLA molecules refers to a peptide sequence of 8-11 amino acids in length in which one or more amino acids are mutated, which can bind or is predicted to bind to specific class I HLA molecules. The "HLA-binding epitope" in the context of class I HLA molecules refers to peptides containing mutated or non-mutated amino acids. For example, the HLA may be a class I HLA molecules.

The "MHC-binding neo-epitope" in the context of class I MHC molecules refers to a peptide sequence of 8-11 amino acids in length in which one or more amino acids are mutated, which can bind or is predicted to bind to specific class I MHC molecules. The "MHC-binding epitope" in the contest of class I MHC molecules refers to peptides containing mutated or non-mutated amino acids.

The "HLA-binding neo-epitope" in the context of class II HLA molecules refers to a peptide sequence of 13-21 amino acids in length in which one or more amino acids are mutated, which can bind or is predicted to bind to specific class II HLA molecules. The "HLA-binding epitope" in the contest of class II HLA molecules refers to peptides containing mutated or non-mutated amino acids.

The "MHC-binding neo-epitope" in the context of class II MHC molecules refers to a peptide sequence of 13-21 amino acids in length in which one or more amino acids are mutated, which can bind or is predicted to bind to specific class II MHC molecules. The "MHC-binding epitope" in the contest of class II MHC molecules refers to peptides containing mutated or non-mutated amino acids.

"T-cell neo-epitopes" refers to a peptide in which one or more amino acids are mutated, which can bind or is predicted to bind to T-cell receptor of CD8+ T-cell or CD4+ T-cell.

An "immunogenic peptide" is by definition a "HLA-binding neoepitope" or "HLA-binding epitope". However, all HLA-binding neoepitopes or HLA-binding epitopes may not be "immunogenic peptides".

The "peptide precursor" is a protein present in the cancer tissue that contains the peptide of interest. Multiple "peptide precursors" can contain the peptide of interest.

A "disease tissue" in this application refers to tumor or cancer tissue from human or mice.

A "tumor" or "neoplasm" is an abnormal growth of tissue whether benign or malignant.

A "cancer" may be a malignant tumor or malignant neoplasm. Cancer refers to any one of cancer, tumor growth, cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancers (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

Examples of tumors include colorectal cancer, osteosarcoma, non-small cell lung cancer, breast cancer, ovarian cancer, glial cancer, solid tumors, metastatic tumor, acute lymphoblastic leukemia, acute myelogenous leukemia, adrenocortical carcinoma, Kaposi sarcoma, lymphoma, anal cancer, astrocytomas, basal cell carcinoma, bile duct cancer, bladder cancer, bone cancer, brain tumor, breast cancer, bronchial tumor, cervical cancer, chronic lymphocytic leukemia, chronic myelogenous leukemia, chronic myeloproliferative disorders, colon cancer, colorectal cancers, ductal carcinoma in situ, endometrial cancer, esophageal cancer, eye cancer, intraocular, retinoblastoma, metastatic melanoma, gallbladder cancer, gastric cancer, gastrointestinal carcinoid tumor, gastrointestinal stromal tumors, glioblastoma, glioma, hairy cell leukemia, head and neck cancer, hepatocellular carcinoma, hepatoma, Hodgkin lymphoma, hypopharyngeal cancer, Langerhans cell histiocytosis, laryngeal cancer, lip and oral cavity cancer, liver cancer, lobular carcinoma in situ, lung cancer, non-small cell lung cancer, small cell lung cancer, lymphoma, AIDS-related lymphoma, Burkitt lymphoma, non-Hodgkin lymphoma, cutaneous T-cell lymphoma, melanoma, squamous neck cancer, mouth cancer, multiple myeloma, myelodysplastic syndromes, myelodysplastic/myeloproliferative neoplasms, nasal cavity and paranasal sinus cancer, nasopharyngeal cancer, neuroblastoma, oral cavity cancer, oropharyngeal cancer, osteosarcoma, ovarian cancer, pancreatic carcinoma, papillary carcinomas, parathyroid cancer, pharyngeal cancer, pheochromocytoma, pineal parenchymal tumors, pineoblastoma, pituitary tumor, pleuropulmonary blastoma, primary central nervous system lymphoma, prostate cancer, rectal cancer, renal cell cancer, salivary gland cancer, sarcoma, Ewing sarcoma, soft tissue sarcoma, squamous cell carcinoma, Sezary syndrome, skin cancer, Merkel cell carcinoma, testicular cancer, throat cancer, thymoma, thymic carcinoma, thyroid cancer, urethral cancer, endometrial cancer, uterine cancer, uterine sarcoma, vaginal cancer, vulvar cancer, Waldenstrom macroglobulinemia, and Wilms tumor. In one embodiment, the tumor is a glioma. In one embodiment, the tumor is a tumor other than a glioma.

For example, an inhibition of growth of a cancer cell means that the rate of growth of a cancer cell that has been treated with a peptide of the invention is 5-fold, 10-fold, 20-fold, 30-fold, 40-fold, 50-fold, 100-fold, or more, less than that of a cancer cell that has not been treated with a peptide of the invention. As used herein, "inhibition" as it refers to the rate of growth of a cancer cell that has been treated with a peptide of the invention also means that the rate is 90%, 80%, 70%, 60%, 50%, 40%, 30%, 25%, 20%, 15%, 10%, 5% or less, lower than the rate of growth of a cancer cell that has not been treated with a peptide of the invention.

An inhibition of growth of a cancer cell also means that the number or growth of cancer cells that have been treated with a peptide of the invention is 5-fold, 10-fold, 20-fold, 30-fold, 40-fold, 50-fold, 100-fold, or more, less than the number or growth of cancer cells that have not been treated with a peptide of the invention. As used herein, "inhibition" as it refers to the rate of growth of a cancer cell also means that the number or growth of cancer cells that have been treated with a peptide of the invention is 90%, 80%, 70%, 60%, 50%, 40%, 30%, 25%, 20%, 15%, 10%, 5% or less, lower than the growth or number of cancer cells that have not been treated with a peptide of the invention.

As used herein, "cancer" may be used interchangeably with "tumor," and vice versa, except when expressly or inherently prohibited. Similarly, "MHC" may be used interchangeably with "HLA," and vice versa, except when expressly or inherently prohibited.

The term "unmutated or wild-type peptide" refers to a peptide derived from normal or healthy tissue cells or tissue. Normal or healthy cells or tissue are free of disease, and in the context of the invention, free of tumor/cancer tissue or cells. Unlike cancer-specific mutant peptide, tumor peptide variant(s) or cancer peptide variant(s), which are mutant or altered peptide specific to cancer or tumor cells or tissues and not present in non-tumor/cancer cells or tissue, the "unmutated or wild-type peptide" may be present in cancer or tumor cells or tissue.

As used herein, the terms "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the present disclosure. "Consisting of" shall mean excluding more than trace elements of other ingredients and substantial method steps. Embodiments defined by each of these transition terms are within the scope of the present disclosure.

Methods of the Invention

The invention describes a method for identifying immunogenic peptides from all genetically altered proteins derived from mammalian cancer samples using a high throughput approach. An accurate high throughput platform for the detection of immunogenic epitopes is critical for clinical translation. The immunogenic peptides can be administered as personal cancer vaccines to individuals affected by the disease in the form of peptides, or as nucleotide-based precursors (e.g., DNA or RNA). The immunogenic peptides can have other applications in identifying specific TCR sequences that engage with the peptide, leading to the development of engineered T cells or CAR-T cells. Additionally, the immunogenic peptides can be used for developing TCR-mimetic reagents to target tumor cells. The methods described herein are useful in personalized cancer immunotherapy space for the treatment of individual cancer patients.

Thus, the present invention in one aspect provides a method of identifying cancer-specific mutant immunogenic peptide from the disease tissue of the individual by combining sequence-specific variant detection method with methods to determine immunogenicity of the peptides.

In another aspect, the present invention provides a method of identifying cancer-specific immunogenic peptides that bind T-cell receptor (TCR).

Also provided are enablement steps useful to practice the invention. Further included are a list of immunogenic peptides from cancer mutations detected by next generation sequencing, cancers presenting such peptides and nucleic acids encoding such peptides identified.

The invention provides methods of selecting cross species cancer vaccines from genetically altered proteins expressed by mouse and human cancer cells and/or tissues. In one embodiment, the method comprises (a) calculating the probability of HLA binding with optimal processing sites from a library of mutant cancer peptides; (b) calculating the probability of TCR binding to generate a T-cell response; and selecting the mutant cancer peptides having the highest probability so calculated from step (a) that can modulate the immune response of a mouse and a human, when challenged with the mutant cancer peptide thereby selecting cross species cancer vaccines; wherein the mouse and human subjects carry the same mutation and express the same HLA molecule that binds the mutant cancer peptide.

In accordance with the practice of the invention the tumor may be derived from any cancer. Examples of cancer cells or tissues include, but are not limited to, cancers of the Breast, Lung, Head & Neck, Skin, Ovary, Pancreatic, Liver, Brain, Prostate, Cervical Thyroid, Bone and Stomach.

The invention further provides methods of selecting mammalian tumor vaccine(s) from genetically altered protein(s) expressed by a mammalian tumor cell or a mammalian tumor tissue from a subject. In one embodiment of the invention, the method comprises the step of obtaining a sample from the subject. The sample may be directly processed as soon as it is obtained or the sample may be stored for a period of time before it is processed in accordance with the invention. The sample obtained from the subject may be cultured in vitro or used to produce cell line before processing in accordance with the invention. The method further comprises the step of identifying the genetically altered protein(s) expressed by the mammalian tumor cell or the mammalian tumor tissue in the sample through nucleic acid sequence(s) encoding the altered protein(s). Additionally, the method includes the step of producing peptide fragment(s) comprising at least one amino acid mutation from the genetically altered protein(s) so identified, so as to obtain peptide variant(s) associated with the mammalian tumor cell or the mammalian tumor tissue. In one embodiment, the peptide fragments are produced in silico using a sliding window method for a fixed or defined peptide length with one amino acid step producing a series of overlapping peptides of a pre-defined length with any mutant amino acid occupying different amino acid position in the series of peptides produced by the sliding window method.

Further, the method additionally comprises the step of selecting the peptide variant(s) which binds T-cell receptor (TCR). In one embodiment, this step comprises i) selecting the peptide variant(s) with a pre-defined length; ii) characterizing the peptide variant(s) in silico by selecting and matching features associated with an amino acid at each position of the peptide with selected pre-defined features for each position of peptides recognized by TCR associated with either CD8+ T-cell or CD4+ T-cell, so as to obtain predictive ability of the peptide variant(s) to interact with the TCR; iii) selecting the peptide variant(s) in step (ii) based on predicted ability of the peptide variant(s) to interact with the TCR, so as to be an immunogenic peptide that may or can serve as a mammalian tumor vaccine(s). Basis for mammalian tumor vaccine(s) using peptide variant(s) identified and selected by the methods of the invention require lengthening the selected peptide variant(s) such that following vaccination the lengthened selected peptide variant(s) is taken up by antigen-presenting cells, processed to the size of the selected peptide variant(s) (before lengthening) and displayed by antigen-presenting cells. In one embodiment, the antigen-presenting cells are professional antigen-presenting cells. In an embodiment, the professional antigen-presenting cells are dendritic cells, macrophages and B lymphocytes. Merely as examples, the peptide variant(s) so selected with a pre-defined length may be a peptide fragment of 8, 9, 10, or 11 amino acids in length. Such a peptide with 8 to 11 amino acids is bound and displayed by class I MHC molecules or class I HLA molecules for TCR binding or interaction. In a preferred embodiment, the peptide variant(s) may be a peptide fragment of 9, 10 or 11 amino acids in length. For example, in a more preferred embodiment, the peptide variant(s) may be a peptide fragment of 9 amino acids in length. In another embodiment, the peptide variant(s) may be a peptide fragment of 13, 14, 15, 16, 17, 18, 19, 20 or 21 amino acids in length. Such a peptide with 13 to 21 amino acids is bound and displayed by class II MHC molecules or class II HLA molecules for TCR binding or interaction. In a preferred embodiment, the peptide variant(s) may be a peptide fragment of 14, 15, 16 or 17 amino acids in length. For example, in a more preferred embodiment, the peptide variant(s) may be a peptide fragment of 16 or 17 amino acids in length. In an embodiment of the invention, the pre-defined length of the peptide variant(s) may vary with the proviso that the size of the peptide variant(s) permits interaction with MHC class I protein(s). In one embodiment, the interaction with MHC class I proteins is a binding reaction that permits display of the peptide variant by MHC class I protein(s). Alternatively, in another embodiment, the pre-defined length of the peptide variant(s) may vary with the proviso that the size of the peptide variant(s) permits interaction with MHC class II protein(s). In one embodiment, the interaction with MHC class II proteins is a binding reaction that permits display of the peptide variant by MHC class II protein(s).

In one embodiment, the immunogenic peptide may be selected further by its ability to bind MHC class-I or class-II protein(s) comprising: a) calculating the binding affinity of the immunogenic peptide to MHC class-I or class-II protein(s); and b) further selecting a set of peptide variant(s) from the previous step where the binding affinity of the unmutated or wild-type peptide is weaker than the variant or the mutated peptide for MHC class-I or class-II protein(s).

In another embodiment, the step of selecting mammalian tumor vaccine(s) includes selecting immunogenic peptide variant(s) for vaccination.

In accordance with the practice of the invention, the mammalian tumor cell or the mammalian tumor tissue may be derived from a mammal, wherein the mammal is selected from the group consisting of human, mouse, rat, cat, dog, bovine, pig, sheep, goat, cow, horse, hamster, guinea pig, rabbit, mink, monkey, chimpanzee, and ape. In one embodiment, the mammalian tumor cell or the mammalian tumor tissue is derived from a mammal, wherein the mammal is a mouse. In one embodiment, the mammalian tumor cell or the mammalian tumor tissue is derived from a mammal, wherein the mammal is a rat. In another embodiment, the mammalian tumor cell or the mammalian tumor tissue is derived from a mammal, wherein the mammal is a human.

In yet another embodiment of the invention, identifying the genetically altered protein(s) expressed by the mammalian tumor cell or the mammalian tumor tissue through nucleic acid sequence(s) encoding the altered protein(s) may comprise (a) the identifying tumor variants from transcriptome analysis of the mammalian tumor cell or mammalian tumor tissue corresponding to protein coding and protein non-coding sequences; and (b) performing conceptual translation or in silico translation of the coding sequences in step (a) so as to identify the genetically altered protein(s) expressed by the mammalian tumor cell or the mammalian tumor tissue.

For example, identifying tumor variants from transcriptome analysis of the mammalian tumor cell or mammalian tumor tissue may comprise the steps of a) determining nucleotide sequence of transcripts produced by the mammalian tumor cell or mammalian tumor tissue; and b) comparing the determined nucleotide sequence of transcripts in (a) with a reference nucleotide sequence of transcripts produced by mammalian non-tumor cell or mammalian non-tumor tissue, so as to identify nucleotide sequence changes in the protein coding and protein non-coding sequences.

In one embodiment, the reference nucleotide sequence of transcripts produced by mammalian non-tumor cell or mammalian non-tumor tissue may be obtained from a publically available database. Alternatively, the reference nucleotide sequence of transcripts produced by mammalian non-tumor cell or mammalian non-tumor tissue may be obtained from a clonal population of a normal culture cell or a collection of clonal population of normal cultured cells, a normal tissue or a collection of normal tissues, a collection of normal tissues from different organ systems, an individual or a collection of individuals, a collection of individuals with similar genetic background, an individual of the same sex or a collection of individuals of the same sex, an individual of a different sex or a collection of individuals of a different sex, an individual of a particular age group or a collection of individuals of a particular age group, a collection of individuals from different stages of development, an individual or group of individuals of a species or sub-species or a combination thereof, wherein normal refers to absence of tumor or tumor material in specimen used to determine the reference nucleotide sequence of transcripts. In one embodiment, the different stages of development may be selected from the group consisting of embryo, fetus, neonate, infant, toddler, early childhood, child, preadolescence, adolescence, adult, middle age and old age and equivalent stages thereof.

For example, the collection of individuals with similar genetic background may be selected from the group consisting of a group of inbred animals or individuals, a collection of family members, a collection of individuals within a family tree, a collection of individuals breeding within a geographic restricted region, a collection of individuals of the same ethnicity and a collection of individuals of the same race.

For example, the species or sub-species may belong to the genus selected from any of *Homo*, *Mus* and *Rattus*. In one embodiment, the species is *Homo sapiens* such as the sub-species is *Homo sapiens*. In another embodiment, the species is any of *Mus musculus*, *Mus booduga*, *Mus caroli*, *Mus cervicolor*, *Mus cookie*, *Mus cypriacus*, *Mus famulus*, *Mus fragilicauda*, *Mus macedonicus*, *Mus nitidulus*, *Mus spicilegus*, *Mus spretus*, *Mus terricolor*, *Mus crociduroides*, *Mus mayori*, *Mus pahari*, *Mus vulcani*, *Mus baoulei*, *Mus bufo*, *Mus callewaerti*, *Mus goundae*, *Mus haussa*, *Mus indutus*, *Mus mahomet*, *Mus mattheyi*, *Mus minutoides*, *Mus musculoides*, *Mus neavei*, *Mus orangiae*, *Mus oubanguii*, *Mus setulosus*, *Mus setzeri*, *Mus sorella*, *Mus tenellus*, *Mus triton*, *Mus fernandoni*, *Mus phillipsi*, *Mus platythrix*, *Mus saxicola*, *Mus shortridgei* or *Mus lepidoides*. In this case, the sub-species may be any of *Mus musculus*, *Mus musculus molossinus*, *Mus musculus castaneus* or *Mus musculus domesticus*.

In yet a further example, the species may be any of *Rattus norvegicus*, *Rattus*, *Rattus annandalei*, *Rattus enganus*, *Rattus everetti*, *Rattus exulans*, *Rattus hainaldi*, *Rattus hoogerwerfi*, *Rattus korinchi*, *Rattus macleari*, *Rattus montanus*, *Rattus morotaiensis*, *Rattus nativitatis*, *Rattus ranjiniae*, *Rattus sanila*, *Rattus stoicus*, *Rattus timorensis*, *Rattus nitidus*, *Rattus pyctoris*, *Rattus turkestanicus*, *Rattus adustus*, *Rattus andamanensis*, *Rattus argentiventer*, *Rattus baluensis*, *Rattus blangorum*, *Rattus burros*, *Rattus hoffmanni*, *Rattus koopmani*, *Rattus losea*, *Rattus lugens*, *Rattus mindorensis*, *Rattus mollicomulus*, *Rattus osgoodi*, *Rattus palmarum*, *Rattus satarae*, *Rattus simalurensis*, *Rattus tanezumi*, *Rattus tawitawiensis*, *Rattus tiomanicus*, *Rattus bontanus*, *Rattus foramineus*, *Rattus marmosurus*, *Rattus pelurus*, *Rattus salocco*, *Rattus xanthurus*, *Rattus arfakiensis*, *Rattus arrogans*, *Rattus elaphinus*, *Rattus feliceus*, *Rattus giluwensis*, *Rattus jobiensis*, *Rattus leucopus*, *Rattus mordax*, *Rattus niobe*, *Rattus novaeguineae*, *Rattus omichlodes*, *Rattus pococki*, *Rattus praetor*, *Rattus richardsoni*, *Rattus steini*, *Rattus vandeuseni*, *Rattus verecundus*, *Rattus colletti*, *Rattus fuscipes*, *Rattus lutreolus*, *Rattus sordidus*, *Rattus tunneyi* or *Rattus villosissimus*.

In yet another embodiment, the reference nucleotide sequence of transcripts produced by mammalian non-tumor cell or mammalian non-tumor tissue may be a composite of nucleotide sequence of transcripts from multiple normal specimen or sources, wherein normal refers to absence of tumor or tumor material in specimen or sources.

In a further embodiment of the invention, the step of identifying the genetically altered protein(s), may further comprise performing genomic analysis for tumor variants in the sequence of the genome present in the mammalian tumor cell or the mammalian tumor tissue but absent or deficient in the mammalian non-tumor cell or the mammalian non-tumor tissue. Merely by way of example, the genomic analysis for tumor variants may include determining nucleotide sequence of the genome or exome.

In another embodiment of the invention, the genetically altered protein(s) expressed by the mammalian tumor cell or the mammalian tumor tissue may be absent or deficient in the mammalian non-tumor cell or the mammalian non-tumor tissue.

In a further embodiment of the invention, the step of producing peptide fragment(s) may comprise at least one amino acid mutation from each genetically altered protein, so as to obtain peptide variant(s) associated with the mammalian tumor cell or the mammalian tumor tissue, the step comprises: defining length of the peptide fragment(s) to be produced from the genetically altered protein; and producing in silico peptide fragment(s) of the pre-defined length at a site of alteration in the protein comprising at least one mutated amino acid of the genetically altered protein.

In another embodiment of the invention, the method comprises identifying a set of tumor variant(s) from a sample comprising mammalian tumor cell or the mammalian tumor tissue from a subject. In accordance with the practice of the invention, in one embodiment, each variant in the genomic sequence corresponds to protein coding or protein non-coding sequence comprising the steps of determining nucleic acid sequence of tumor genetic material and comparing to non-tumor reference sequence to identify tumor variant(s). In an embodiment, the method further comprises the step of detecting the tumor variant(s) expressed by the mammalian tumor cell or the mammalian tumor tissue resulting in an alteration in mRNA sequence and sequence of protein translated from the mRNA. Additionally, the method comprises the step of translating in silico the mRNA so identified in step (b) to obtain genetically altered protein(s) produced or expected to be produced by the mammalian tumor cell or the mammalian tumor tissue. Further, the method comprises generating peptide fragment(s) of a pre-defined length in silico from the altered protein(s), after which, the method further provides the steps of identifying peptide variant(s) of the mammalian tumor cell or the mammalian tumor tissue which is not associated with mammalian non-tumor cell or tissue; predicting immunogenicity of the peptide variant(s) comprising a step of in silico assessment of peptide ability to interact with T-cell receptor; and selecting immunogenic peptide variant(s) based on the predicted ability of the peptide variant(s) to interact with the TCR, which may be used as a basis for mammalian tumor vaccine(s). Basis for mammalian tumor vaccine(s) using peptide variant(s) identified and selected by the methods of the invention requires lengthening the selected peptide variant(s) such that following vaccination, the lengthened selected peptide variant(s) is taken up by antigen-presenting cells, processed to the size of the selected peptide variant(s) (before lengthening) and displayed by antigen-presenting cells. In one embodiment, the antigen-presenting cells are professional antigen-presenting cells. In an embodiment, the professional antigen-presenting cells are dendritic cells, macrophages and B lymphocytes.

In another embodiment of the invention, the immunogenic peptide may be further selected by its potential or ability to be produced inside the cell by processes comprising the steps of determining the action of proteases, which are part of the proteasomal or immunoproteasomal complexes, based on the probability that the processing event of the altered protein(s) will produce the immunogenic peptide so selected; and determining the entry of the immunogenic peptide into the endoplasmic reticulum compartment by binding to peptide transporters expressed on the surface of the compartment. For example, the peptide transporter may be a transporter associated with antigen processing (TAP) comprising TAP1 and TAP2.

In accordance with the practice of the invention, the methods of the invention may further comprise predicting immunogenicity of peptide variant(s) derived from the mammalian tumor cell or the mammalian tumor tissue, and optionally, immunogenicity of corresponding non-variant peptide from mammalian non-tumor cell or the mammalian non-tumor tissue.

In another embodiment of the invention, the immunogenic peptide may be further selected by its potential or ability to be produced inside the cell by processes comprising: a) determining action of proteases, which are part of the lysosome and/or endosomal compartments, based on the probability that the processing event of the altered protein(s) will produce the immunogenic peptide so selected; and b) determining the fusion of the endosomal and/or lysosomal vesicles with Golgi-derived vesicles to permit loading of the immunogenic peptide onto MHC class II proteins.

In one embodiment of the invention, the length of the peptide fragment(s) to be produced from the genetically altered protein or the peptide fragment(s) of the pre-defined length is 8 amino acids or more. In another embodiment, the length of the peptide fragment(s) to be produced from the genetically altered protein or peptide fragment(s) of the pre-defined length is less than 18 amino acids.

In yet a further embodiment, the length of the peptide fragment(s) to be produced from the genetically altered protein or the peptide fragment(s) of the pre-defined length may be a length that permits binding by MHC class I protein. For example, the length that permits binding by MHC class I protein may be selected to be 8, 9, 10, or 11 amino acids long. In another example, the length that permits binding by MHC class II protein is selected to be 13, 14, 15, 16, 17, 18, 19, 20 or 21 amino acids long.

In another embodiment, the length of the peptide fragment(s) to be produced from the genetically altered protein or the peptide fragment(s) of the pre-defined length is about 9, 10 or 11 amino acids long. In a specific example, the length of the peptide fragment(s) to be produced from the genetically altered protein or the peptide fragment(s) of the pre-defined length is 9 amino acids long.

In yet another embodiment, the length of the peptide fragment(s) further supports interaction with the TCR of CD8+ T-cell or CD4+ T-cell.

In still another embodiment, the interaction with the TCR of CD8+ T-cell or CD4+ T-cell results in a complex comprising the peptide, MHC class I protein and TCR of CD8+ T-cell, or alternatively, the peptide, MHC class II protein and TCR of CD4+ T-cell.

In an additional embodiment, interaction with the TCR of CD8+ T-cell or CD4+ T-cell results in a complex comprising the peptide, MHC class I protein and TCR of CD8+ T-cell, or alternatively, the peptide, MHC class II protein and TCR of CD4+ T-cell.

Also, in another embodiment, the mammalian tumor cell is a cell of a mammalian cell line derived from the tumor of a mammal. Merely by way of example, the mammal is selected from the group of human, mouse, rat, cat, dog, bovine, pig, sheep, goat, cow, horse, hamster, guinea pig, rabbit, mink, monkey, chimpanzee, and ape. In one embodiment, the mammal is a mouse or a human. In another embodiment, the tumor is a cancer. In yet a further embodiment, the mammalian tumor cell is a cell of a mouse cancer cell line. In a further still embodiment, the mammalian tumor cell is a cell of a human cancer cell line. Further, the mammalian tumor cell or mammalian tumor tissue may be present in or derived from a mouse or human subject.

Additionally, in accordance with the practice of the invention, the features associated with an amino acid at each position of the peptide may be physicochemical and/or biological properties of the amino acid. For example, each physicochemical and/or biological property of an amino acid may be assigned a numerical value within the context of other numerical values assigned to other amino acids.

Suitable examples of pre-defined features in accordance with the invention, include, but are not limited to, one of more of alpha-CH chemical shifts, hydrophobicity index (1), signal sequence helical potential, membrane-buried preference parameters, conformational parameter of inner helix, conformational parameter of beta-structure, conformational parameter of beta-turn, average flexibility indices, residue volume, information value for accessibility—average fraction 35%, information value for accessibility—average fraction 23%, retention coefficient in TFA, retention coefficient in HFBA, transfer free energy to surface, apparent partial specific volume, alpha-NH chemical shifts, alpha-CH chemical shifts, spin-spin coupling constants 3JHalpha-NH, normalized frequency of alpha-helix, normalized frequency of extended structure, steric parameter, polarizability parameter, free energy of solution in water-kcal/mole, Chou-Fasman parameter of the coil conformation, a parameter defined from the residuals obtained from the best correlation of the Chou-Fasman parameter of beta-sheet, number of atoms in the side chain labelled 1+1, number of atoms in the side chain labelled 2+1, number of atoms in the side chain labelled 3+1, number of bonds in the longest chain, a parameter of charge transfer capability, a parameter of charge transfer donor capability, average volume of buried residue, residue accessible surface area in tripeptide, residue accessible surface area in folded protein, proportion of residues 95% buried, proportion of residues 100% buried, normalized frequency of beta-turn-1, normalized frequency of alpha-helix, normalized frequency of beta-sheet, normalized frequency of beta-turn-2, normalized frequency of N-terminal helix, normalized frequency of C-terminal helix, normalized frequency of N-terminal non helical region, normalized frequency of C-terminal non helical region, normalized frequency of N-terminal beta-sheet, normalized frequency of C-terminal beta-sheet, normalized frequency of N-terminal non beta region, normalized frequency of C-terminal non beta region, frequency of the 1st residue in turn, frequency of the 2nd residue in turn, frequency of the 3rd residue in turn, frequency of the 4th residue in turn, normalized frequency of the 2nd and 3rd residues in turn, normalized hydrophobicity scales for alpha-proteins, normalized hydrophobicity scales for beta-proteins, normalized hydrophobicity scales for alpha+beta-proteins, normalized hydrophobicity scales for alpha/beta-proteins, normalized average hydrophobicity scales, partial specific volume, normalized frequency of middle helix, normalized frequency of beta-sheet, normalized frequency of turn, size, amino acid composition, relative mutability, membrane preference for cytochrome b: MPH89, average membrane preference: AMP07, consensus normalized hydrophobicity scale, solvation free energy, atom-based hydrophobic moment, direction of hydrophobic moment, molecular weight, melting point, optical rotation, pK-N, pK-C, hydrophobic parameter pi, graph shape index, smoothed upsilon steric parameter, normalized van der Waals volume, STERIMOL length of the side chain, STERIMOL minimum width of the side chain, STERIMOL maximum width of the side chain, N.M.R. chemical shift of alpha-carbon, localized electrical effect, number of hydrogen bond donors, number of full nonbonding orbitals, positive charge, negative charge, pK-a (RCOOH), helix-coil equilibrium constant, helix initiation parameter at position i−1, helix initiation parameter (at position i, i+1, and i+2), helix termination parameter (at position j−2, j−1, and j), helix termination parameter at position j+1, partition coefficient, alpha-helix indices, alpha-helix indices for alpha-proteins, alpha-helix indices for beta-proteins, alpha-helix indices for alpha/beta-proteins, beta-strand indices, beta-strand indices for beta-proteins, beta-strand indices for alpha/beta-proteins, aperiodic indices, aperiodic indices for alpha-proteins, aperiodic indices for beta-proteins, aperiodic indices for alpha/beta-proteins, hydrophobicity factor, residue volume, composition, polarity, volume, partition energy, hydration number, hydrophilicity value, heat capacity, absolute entropy, entropy of formation, normalized relative frequency of alpha-helix, normalized relative frequency of extended structure, normalized relative frequency of bend, normalized relative frequency of bend R, normalized relative frequency of bend S, normalized relative frequency of helix end, normalized relative frequency of double bend, normalized relative frequency of coil, average accessible surface area, percentage of buried residues, percentage of exposed residues, ratio of buried and accessible molar fractions, transfer free energy, hydrophobicity (1), pK (—COOH), relative frequency of occurrence, relative mutability, amino acid distribution, sequence frequency, average relative probability of helix, average relative probability of beta-sheet, average relative probability of inner helix, average relative probability of inner beta-sheet, flexibility parameter for no rigid neighbors, flexibility parameter for one rigid neighbor, flexibility parameter for two rigid neighbors, Kerr-constant increments, net charge, side chain interaction parameter (1), side chain interaction parameter (2), fraction of site occupied by water, side chain volume, hydropathy index, transfer free energy, CHP/water, hydrophobic parameter, distance between C-alpha and centroid of side chain, side chain angle theta(AAR), side chain torsion angle phi(AAAR), radius of gyration of side chain, van der Waals parameter RO, van der Waals parameter epsilon, normalized frequency of alpha-helix with weights, Normalized frequency of beta-sheet with weights, normalized frequency of reverse turn with weights, normalized frequency of alpha-helix (unweighted), normalized frequency of beta-sheet (unweighted), normalized frequency of reverse turn (unweighted), frequency of occurrence in beta-bends, conformational preference for all beta-strands, conformational preference for parallel beta-strands, conformational preference for antiparallel beta-strands, average surrounding hydrophobicity, normalized frequency of alpha-helix, normalized frequency of extended structure, normalized frequency of zeta R, normalized frequency of left-handed alpha-helix, normalized frequency of zeta L, normalized frequency of alpha region, refractivity, retention coefficient in HPLC (pH7.4), retention coefficient in HPLC (pH2.1), retention coefficient in NaClO4, retention coefficient in NaH2PO4, average reduced distance for C-alpha, average reduced distance for side chain, average side chain orientation angle, effective partition energy, normalized frequency of alpha-helix, normalized frequency of beta-structure, normalized frequency of coil, AA composition of total proteins, SD of AA composition of total proteins, AA composition of mt-proteins, normalized composition of mt-proteins, AA composition of mt-proteins from animal, normalized composition from animal, AA composition of mt-proteins from fungi and plant, normalized composition from fungi and plant, AA composition of membrane proteins, normalized composition of membrane proteins, transmembrane regions of non-mt-proteins, transmembrane regions of mt-proteins, ratio of average and computed composition, AA composition of CYT of single-spanning proteins, AA composition of CYT2 of single-spanning proteins, AA composition of EXT of single-spanning proteins, AA composition of EXT2 of single-spanning proteins, AA composition of MEM of single-spanning proteins, AA composition of CYT of multi-spanning proteins, AA composition of EXT of multi-spanning proteins, AA composition of MEM of multi-spanning proteins, 8 A contact number, 14 A contact number, transfer energy, organic solvent/water, average non-bonded energy per atom, short and medium range non-bonded energy per atom, long range non-bonded energy per atom, average non-bonded energy per residue, short and medium range non-bonded energy per residue, optimized beta-structure-coil equilibrium constant, optimized propensity to form reverse turn, optimized transfer energy parameter, optimized average non-bonded energy per atom, optimized side chain interaction parameter, normalized frequency of alpha-helix from LG, normalized frequency of alpha-helix from CF, normalized frequency of beta-sheet from LG, normalized frequency of beta-sheet from CF, normalized frequency of turn from LG, normalized frequency of turn from CF, normalized frequency of alpha-helix in all-alpha class, normalized frequency of alpha-helix in alpha+beta class, normalized frequency of alpha-helix in alpha/beta class, normalized frequency of beta-sheet in all-beta class, normalized frequency of beta-sheet in alpha+beta class, normalized frequency of beta-sheet in alpha/beta class, normalized frequency of turn in all-alpha class, normalized frequency of turn in all-beta class, normalized frequency of turn in alpha+beta class, normalized frequency of turn in alpha/beta class, HPLC parameter, partition coefficient, surrounding hydrophobicity in folded form, average gain in surrounding hydrophobicity, average gain ratio in surrounding hydrophobicity, surrounding hydrophobicity in alpha-helix, surrounding hydrophobicity in beta-sheet, surrounding hydrophobicity in turn, accessibility reduction ratio, average number of surrounding residues, intercept in regression analysis, slope in regression analysis×1.0E1, correlation coefficient in regression analysis, hydrophobicity (2), relative frequency in alpha-helix, relative frequency in beta-sheet, relative frequency in reverse-turn, helix-coil equilibrium constant, beta-coil equilibrium constant, weights for alpha-helix at the window position of −6, weights for alpha-helix at the window position of −5, weights for alpha-helix at the window position of −4, weights for alpha-helix at the window position of −3, weights for alpha-helix at the window position of −2, weights for alpha-helix at the window position of −1, weights for alpha-helix at the window position of 0, weights for alpha-helix at the window position of 1, weights for alpha-helix at the window position of 2, weights for alpha-helix at the window position of 3, weights for alpha-helix at the window position of 4, weights for alpha-helix at the window position of 5, weights for alpha-helix at the window position of 6, weights for beta-sheet at the window position of −6, weights for beta-sheet at the window position of −5, weights for beta-sheet at the window position of −4, weights for beta-sheet at the window position of −3, weights for beta-sheet at the window position of −2, weights for beta-sheet at the window position of −1, weights for beta-sheet at the window position of 0, weights for beta-sheet at the window position of 1, weights for beta-sheet at the window position of 2, weights for beta-sheet at the window position of 3, weights for beta-sheet at the window position of 4, weights for beta-sheet at the window position of 5, weights for beta-sheet at the window position of 6, weights for coil at the window position of −6, weights for coil at the window position of −5, weights for coil at the window position of −4, weights for coil at the window position of −3, weights for coil at the window position of −2, weights for coil at the window position of −1, weights for coil at the window position of 0, weights for coil at the window position of 1, weights for coil at the window position of 2, weights for coil at the window position of 3, weights for coil at the window position of 4, weights for coil at the window position of 5, weights for coil at the window position of 6, average reduced distance for C-alpha, average reduced distance for side chain, side chain orientational preference, average relative fractional occurrence in A0(i), average relative fractional occurrence in AR(i), average relative fractional occurrence in AL(i), average relative fractional occurrence in EL(i), average relative fractional occurrence in E0(i), average relative fractional occurrence in ER(i), average relative fractional occurrence in A0(i−1), average relative fractional occurrence in AR(i−1), average relative fractional occurrence in AL(i−1), average relative fractional occurrence in EL(i−1), average relative fractional occurrence in E0(i−1), value of theta(i), value of theta(i−1), transfer free energy from chx to wat, transfer free energy from oct to wat, transfer free energy from yap to chx, transfer free energy from chx to oct, transfer free energy from vap to oct, accessible surface area, energy transfer from out to in (95% buried), mean polarity, relative preference value at N", relative preference value at N', relative preference value at N-cap, relative preference value at N1, relative preference value at N2, relative preference value at N3, relative preference value at N4, relative preference value at N5, relative preference value at Mid, relative preference value at C5, relative preference value at C4, relative preference value at C3, relative preference value at C2, relative preference value at C1, relative preference value at C-cap, relative preference value at C', relative preference value at C", Information measure for alpha-helix, information measure for N-terminal helix, Information measure for middle helix, information measure for C-terminal helix, information measure for extended, information measure for pleated-sheet, information measure for extended without H-bond, information measure for turn, information measure for N-terminal turn, information measure for middle turn, information measure for C-terminal turn, information measure for coil, information measure for loop, hydration free energy, mean area buried on transfer, mean fractional area loss, side chain hydropathy—uncorrected for solvation, side chain hydropathy—corrected for solvation, loss of side chain hydropathy by helix formation, transfer free energy, principal component I, principal component II, principal component III, principal component IV, Zimm-Bragg parameter s at 20 C, Zimm-Bragg parameter sigmax1.0E4, optimal matching hydrophobicity, normalized frequency of alpha-helix, normalized frequency of isolated helix, normalized frequency of extended structure, normalized frequency of chain reversal R, normalized frequency of chain reversal S, normalized frequency of chain reversal D, normalized frequency of left-handed helix, normalized frequency of zeta R, normalized frequency of coil, normalized frequency of chain reversal, relative population of conformational state A, relative population of conformational state C, relative population of conformational state E, electron-ion interaction potential, bitterness, transfer free energy to lipophilic phase, average interactions per side chain atom, RF value in high salt chromatography, propensity to be buried inside, free energy change of epsilon(i) to epsilon(ex), free energy change of alpha(Ri) to alpha(Rh), free energy change of epsilon(i) to alpha(Rh), polar requirement, hydration potential, principal property value z1, principal property value z2, principal property value z3, unfolding Gibbs energy in water (pH7.0), unfolding Gibbs energy in water (pH9.0), activation Gibbs energy of unfolding (pH7.0), activation Gibbs energy of unfolding (pH9.0), dependence of partition coefficient on ionic strength, hydrophobicity (3), bulkiness, polarity, isoelectric point, RF rank, normalized positional residue frequency at helix termini N4', normalized positional residue frequency at helix termini N''', normalized positional residue frequency at helix termini N", normalized positional residue frequency at helix termini N', normalized positional residue frequency at helix termini Nc, normalized positional residue frequency at helix termini N1, normalized positional residue frequency at helix termini N2, normalized positional residue frequency at helix termini N3, normalized positional residue frequency at helix termini N4, normalized positional residue frequency at helix termini N5, normalized positional residue frequency at helix termini C5, normalized positional residue frequency at helix termini C4, normalized positional residue frequency at helix termini C3, normalized positional residue frequency at helix termini C2, normalized positional residue frequency at helix termini C1, normalized positional residue frequency at helix termini Cc, normalized positional residue frequency at helix termini C', normalized positional residue frequency at helix termini C", normalized positional residue frequency at helix termini C''', normalized positional residue frequency at helix termini C4', Delta G values for the peptides extrapolated to 0 M urea, helix formation parameters (delta G), normalized flexibility parameters (B-values)—average, normalized flexibility parameters (B-values) for each residue surrounded by none rigid neighbors, normalized flexibility parameters (B-values) for each residue surrounded by one rigid neighbors, normalized flexibility parameters, Free energy in alpha-helical conformation, free energy in alpha-helical region, Free energy in beta-strand conformation, free energy in beta-strand region, free energy in beta-strand region, free energies of transfer of AcWl-X-LL peptides from bilayer interface to water, thermodynamic beta sheet propensity, turn propensity scale for transmembrane helices, alpha helix propensity of position 44 in T4 lysozyme, p-Values of mesophilic proteins based on the distributions of B values, p-Values of thermophilic proteins based on the distributions of B values, distribution of amino acid residues in the 18 non-redundant families of thermophilic proteins, distribution of amino acid residues in the 18 non-redundant families of mesophilic proteins, distribution of amino acid residues in the alpha-helices in thermophilic proteins, distribution of amino acid residues in the alpha-helices in mesophilic proteins, side-chain contribution to protein stability (kJ/mol), propensity of amino acids within pi-helices, hydropathy scale based on self-information values in the two-state model (5% accessibility), hydropathy scale based on self-information values in the two-state model (9% accessibility), hydropathy scale based on self-information values in the two-state model (16% accessibility), hydropathy scale based on self-information values in the two-state model (20% accessibility), hydropathy scale based on self-information values in the two-state model (25% accessibility), hydropathy scale based on self-information values in the two-state model (36% accessibility), hydropathy scale based on self-information values in the two-state model (50% accessibility), averaged turn propensities in a transmembrane helix, alpha-helix propensity derived from designed sequences, beta-sheet propensity derived from designed sequences, composition of amino acids in extracellular proteins (percent), composition of amino acids in anchored proteins (percent), composition of amino acids in membrane proteins (percent), composition of amino acids in intracellular proteins (percent), composition of amino acids in nuclear proteins (percent), surface composition of amino acids in intracellular proteins of thermophiles (percent), surface composition of amino acids in intracellular proteins of mesophiles (percent), surface composition of amino acids in extracellular proteins of mesophiles (percent), surface composition of amino acids in nuclear proteins (percent), interior composition of amino acids in intracellular proteins of thermophiles (percent), interior composition of amino acids in intracellular proteins of mesophiles (percent), interior composition of amino acids in extracellular proteins of mesophiles (percent), interior composition of amino acids in nuclear proteins (percent), entire chain composition of amino acids in intracellular proteins of thermophiles (percent), entire chain composition of amino acids in intracellular proteins of mesophiles (percent), entire chain composition of amino acids in extracellular proteins of mesophiles (percent), entire chain composition of amino acids in nuclear proteins (percent), screening coefficients gamma (local), screening coefficients gamma (non-local), slopes tripeptide—FDPB VFF neutral, slopes tripeptides—LD VFF neutral, slopes tripeptide—FDPB VFF noside, slopes tripeptide FDPB VFF all, slopes tripeptide FDPB PARSE neutral, slopes dekapeptide—FDPB VFF neutral, slopes proteins—FDPB VFF neutral, side-chain conformation by gaussian evolutionary method, amphiphilicity index, volumes including the crystallographic waters using the ProtOr, volumes not including the crystallographic waters using the ProtOr, electron-ion interaction potential values, hydrophobicity scales, hydrophobicity coefficient in RP-HPLC-C18 with 0.1% TFA/MeCN/H2O, hydrophobicity coefficient in RP-HPLC-C8 with 0.1% TFA/MeCN/H2O, hydrophobicity coefficient in RP-HPLC-C4 with 0.1% TFA/MeCN/H2O, hydrophobicity coefficient in RP-HPLC-C18 with 0.1% TFA/2-PrOH/MeCN/H2O, hydrophilicity scale, retention coefficient at pH 2, modified Kyte-Doolittle hydrophobicity scale, interactivity scale obtained from the contact matrix, interactivity scale obtained by maximizing the mean of correlation coefficient over single-domain globular proteins, interactivity scale obtained by maximizing the mean of correlation coefficient over pairs of sequences sharing the TIM barrel fold, linker propensity index, knowledge-based membrane-propensity scale from 1D_Helix in MPtopo databases, knowledge-based membrane-propensity scale from 3D_Helix in MPtopo databases, linker propensity from all dataset, linker propensity from 1-linker dataset, linker propensity from 2-linker dataset, linker propensity from 3-linker dataset, linker propensity from small dataset, linker propensity from medium dataset, linker propensity from long dataset, linker propensity from helical, linker propensity from non-helical (annotated by DSSP) dataset, stability scale from the knowledge-based atom-atom potential, relative stability scale extracted from mutation experiments, buriability, linker index, mean volumes of residues buried in protein interiors, average volumes of residues, hydrostatic pressure asymmetry index—PAI, hydrophobicity index (2), average internal preferences, hydrophobicity-related index, apparent partition energies calculated from Wertz-Scheraga index, apparent partition energies calculated from Robson-Osguthorpe index, apparent partition energies calculated from Janin index, apparent partition energies calculated from Chothia index, hydropathies of amino acid side chains—neutral form, hydropathies of amino acid side chains—pi-values in pH 7.0, weights from the IFH scale, hydrophobicity index 3.0 pH, scaled side chain hydrophobicity values, hydrophobicity scale from native protein structures, NNEIG index, SWEIG index, PRIFT index, PRILS index, ALTFT index, ALTLS index, TOTFT index, TOTLS index, relative partition energies derived by the Bethe approximation, optimized relative partition energies—method A, optimized relative partition energies—method B, optimized relative partition energies—method C, optimized relative partition energies—method D, hydrophobicity index (3) and hydrophobicity index (4) and combinations thereof.

In a preferred embodiment, pre-defined features comprise any one or more of polar, non-polar, hydrophobic, helix/turn motif, β-sheet structure motif, charge of main chain, charge of side chain, solvent accessibility of an amino acid, spatial flexibility of the main chain and spatial flexibility of side chain of an amino acid.

In one preferred embodiment of the invention, the peptide variant(s) with a pre-defined length is 9 amino acid long and pre-defined features comprise any one or more of polar, non-polar, hydrophobic, helix/turn motif, β-sheet structure motif, charge of main chain, charge of side chain, solvent accessibility of an amino acid, spatial flexibility of the main chain and spatial flexibility of side chain of an amino acid. In one embodiment of the invention, the pre-defined features comprise hydrophobic and helix/turn motif.

In another preferred embodiment of the invention, the peptide variant(s) with a pre-defined length and pre-defined features comprise at least hydrophobic and helix/turn motif. For example, the peptide variant(s) with a pre-defined length may be 9 amino acids long and pre-defined features comprise hydrophobic and helix/turn motif.

In accordance with the practice of one aspect of the invention, the predictive ability of the peptide variant(s) to interact with the TCR comprises a numerical value or set of numerical values in which the value or set of numerical values is reflective of the degree of matching of the features associated with the amino acids of the peptide variant(s) to the pre-defined features for each position of the peptides recognized by TCR-associated with either CD8+ T-cell or CD4+ T-cell.

Further, obtaining the pre-defined features for each position of peptides recognized by TCR-associated with either CD8+ T-cell or CD4+ T-cell comprises a) aligning end-to-end peptides of same size with pre-defined length known to be bound by TCR-associated with either CD8+ T-cell or CD4+ T-cell; b) optionally, aligning end-to-end peptides of same size as in (a) known not to be bound by TCR-associated with either CD8+ T-cell or CD4+ T-cell but known to be bound by either MHC class I protein(s) or MHC class II protein(s); and c) determining amino acid features most prevalent or avoided at each amino acid position from the aligned sequences in (a) and/or (b); thereby, obtaining the pre-defined features for each position of peptides recognized by TCR-associated with either CD8+ T-cell or CD4+ T-cell.

In one embodiment of the invention, the selected peptide variant(s) with a predicted ability to interact with the TCR and may or can serve as a mammalian tumor vaccine(s) may be any of the peptides provided in Table 1.

In accordance with the practice of the invention, the methods of the invention may further comprise predicting a rank ordered list of the immunogenic peptides derived from mammalian tumor cell or mammalian tumor tissue so selected. The peptide may be a peptide variant. Moreover, rank ordering peptides may be based on a combination of the following parameters: a) expression of variant gene from which variant peptide is derived; b) predicted ability to bind TCR of CD8+ T-cell; c) binding affinity of the peptide to MHC class-I protein(s); d) peptide processing by proteases; and/or e) peptide transporter binding. Further, each parameter may be subdivided to reflect quality of the parameter through numerical value(s) or range(s) of values, and further, the numerical value(s) or range(s) of values from the parameters assessed or combined so as to produce output(s) permissive of sorting by ascending or descending order, thereby predicting a rank ordered list of the immunogenic peptides derived from mammalian tumor cell or mammalian tumor tissue so selected.

In another embodiment, the methods of the invention may further comprise predicting a rank ordered list of immunogenic peptides derived from mammalian tumor cell or mammalian tumor tissue, wherein the peptide is a peptide variant and wherein rank ordering peptides is based on a combination of the following parameters: a) expression of variant gene from which variant peptide is derived; b) predicted ability to bind TCR of CD4+ T-cell; c) binding affinity of the peptide to MHC class-II protein(s); d) peptide processing by lysosome and/or endosome; and/or e) fusion of the endosomal and/or lysosomal vesicles with Golgi-derived vesicles to permit loading of the immunogenic peptide onto MHC class II proteins.

In one embodiment of the invention, the immunogenic peptide so selected may be further selected by its ability to bind MHC class-I or class-II protein(s) or for its ability to bind a specific MHC class-I protein derived from a particular allele of MHC class I gene or specific MHC class-II proteins derived from two particular MHC class II genes. For example, the MHC class-I or class-II protein(s) may be encoded by the human leukocyte antigen gene complex (HLA). As a further example, the particular allele of MHC class I gene may be encoded by HLA-A locus, HLA-B locus, HLA-C locus, HLA-E locus, HLA-F locus or HLA-G locus. Further examples of the particular allele of MHC class I gene may be selected from the set as shown in Table 2.

Additionally, in one embodiment, the specific MHC class-II proteins may be derived from two particular MHC class II genes to form a heterodimer of an alpha chain and a beta chain. For example, the heterodimer may be any or HLA-DM, HLA-DO, HLA-DP, HLA-DQ and HLA-DR. IN another example, the alpha chain of HLA-DM heterodimer may be encoded by HLA-DMA locus, alpha chain of HLA-DO heterodimer is encoded by HLA-DOA locus, alpha chain of HLA-DP heterodimer is encoded by HLA-DPA1 locus, alpha chain of HLA-DQ heterodimer is encoded by HLA-DQA1 locus or HLA-DQA2 locus, and alpha chain of HLA-DR is encoded by HLA-DR locus. In a further example, the beta chain of HLA-DM heterodimer may be encoded by any of HLA-DMB locus, beta chain of HLA-DO heterodimer is encoded by HLA-DOB locus, beta chain of HLA-DP heterodimer is encoded by HLA-DPB1 locus, beta chain of HLA-DQ heterodimer is encoded by HLA-DQB1 locus or HLA-DQB2 locus, and beta chain of HLA-DR is encoded by HLA-DRB1 locus, HLA-DRB3 locus, HLA-DRB4 or HLA-DRB5 locus. Further examples of the particular allele of MHC class II gene may be selected from the set as shown in Table 3.

In accordance with the invention the allele may be described by a classification system comprising HLA prefix, separated by hyphen, followed by HLA gene, field separator, serotype, protein coded by allele in order of discovery, one or more numbers designated by gene sequencing and expression, or a combination thereof. Currently, there are more than 7,670 MHC class I alleles and more than 2,260 MHC class II alleles. In addition, each locus may comprise multiple genes or alleles of MHC class-I or class-II protein(s).

In accordance with the invention, the methods of the invention may further comprise MHC-typing of the tumor cell or tumor tissue in selection of immunogenic peptide(s), so as to select immunogenic peptide(s) which may be displayed by the tumor cell or tumor tissue, by cells of individual or subject from which tumor cell or tumor tissue is derived, or by immune cells of individual or subject from which tumor cell or tumor tissue is derived.

In accordance with the invention, the methods of the invention may further comprise HLA-typing of the tumor cell or tumor tissue in selection of immunogenic peptide(s), so as to select immunogenic peptide(s) which may be displayed by the tumor cell or tumor tissue, by cells of individual or subject from which tumor cell or tumor tissue is derived, or by immune cells of individual or subject from which tumor cell or tumor tissue is derived.

In one embodiment of the invention, the prediction of immunogenic peptide(s) may further comprise MHC-typing analysis comprising the steps of: a) determining serotype or expressed isotype or supertype of MHC class-I or class-II protein(s) expressed by MHC class-I or class-II genes of the mammalian tumor cell or tumor tissue, or alternatively of the cell or immune cell of an individual or subject to be administered with mammalian tumor vaccine(s) comprising the predicted immunogenic peptide(s); b) calculating probability of MHC class-I or class-II protein(s) of (a) binding mammalian tumor peptide variant(s) with optimal processing sites from a library of tumor peptide variants; c) calculating probability of TCR binding to generate a T-cell response; d) selecting tumor peptide variant(s) having highest probability from steps (b) that can modulate the immune response of a mammal when challenged with the tumor peptide variant(s), thereby further selecting mammalian tumor vaccine(s) dependent on MHC class-I or class-II expression of the mammalian tumor cell or tumor tissue, or alternatively of the cell or immune cell of an individual or subject to be administered with mammalian tumor vaccine(s) comprising the predicted immunogenic peptide(s).

In another embodiment, the prediction of immunogenic peptide(s) may further comprise the steps of HLA-typing analysis comprising: a) determining serotype or expressed isotype or supertype of HLA protein(s) expressed by HLA genes of the mammalian tumor cell or tumor tissue, or alternatively of the cell or immune cell of an individual or subject to be administered with mammalian tumor vaccine(s) comprising the predicted immunogenic peptide(s); b) calculating probability of HLA protein(s) of (a) binding mammalian tumor peptide variant(s) with optimal processing sites from a library of tumor peptide variants; c) calculating probability of TCR binding to generate a T-cell response; d) selecting tumor peptide variant(s) having highest probability from steps (b) that can modulate the immune response of a mammal when challenged with the tumor peptide variant(s), thereby further selecting mammalian tumor vaccine(s) dependent on HLA expression of the mammalian tumor cell or tumor tissue, or alternatively of the cell or immune cell of an individual or subject to be administered with mammalian tumor vaccine(s) comprising the predicted immunogenic peptide(s).

In accordance with the invention, the mammalian tumor vaccine(s) may comprise the selected immunogenic peptide so identified by computation method.

Further, in accordance with the invention, selected immunogenic peptide in the mammalian tumor vaccine(s) may have amino-terminal and carboxyl-terminal extensions. For example, the amino-terminal and carboxyl-terminal extensions may be amino acids. The amino acids in the amino-terminal and carboxyl-terminal extensions may permit processing of the selected immunogenic peptide of claim 1 or 3 so as to be displayed by the MHC class I protein(s) and/or the MHC class II protein(s). For example, the MHC class I protein(s) and/or the MHC class II proteins(s) may be associated with a human. Further, the MHC class I protein(s) and/or the MHC class II protein(s) associated with a human may be an HLA protein(s).

Additionally, the invention provides methods of preparing a subject-specific immunogenic peptide composition comprising selecting cancer vaccines from genetically altered proteins expressed by mammalian cancer cells and tissues by any of the methods of the invention. Merely by way of example, said subject-specific peptides, may comprise: (a) a peptide that has a non-synonymous mutation leading to different amino acids in comparison with a protein of the non-tumor sample; (b) a peptide having a read-through mutation in which a stop codon is modified or deleted, leading to translation of a longer protein in comparison with a protein of the non-tumor sample with a novel tumor-specific sequence at the C-terminus; (c) a peptide that has a splice site mutation that leads to the inclusion of an intron or part of an intron, or alternatively exclusion of an exon or part of an exon, in the mature mRNA and thus has a unique tumor-specific protein sequence; (d) a peptide representing a chromosomal rearrangement that has given rise to a chimeric protein with tumor-specific sequences at the junction of two proteins of the non-tumor sample and thus represents a gene fusion; or (e) a peptide representing in comparison with a protein of the non-tumor sample a frameshift mutation or deletion that leads to a new open reading frame and a novel tumor-specific protein sequence. The subject-specific immunogenic composition may comprise a subject-specific peptide that binds to the HLA protein of the subject with an IC50 less than about 500 nM.

The invention additionally provides methods of treating a subject having cancer. In one embodiment, the method comprises administering in the subject an immunogenic peptide, composition of the invention or cancer vaccines so selected by any of the methods of the invention in a sufficient amount so as to treat the cancer.

In another embodiment, the method comprises a) obtaining a sample from the subject; b) identifying the genetically altered protein(s) expressed by the mammalian tumor cell or the mammalian tumor tissue in the sample through nucleic acid sequence(s) encoding the altered protein(s); b) producing peptide fragment(s) comprising at least one amino acid mutation from the genetically altered protein(s) so identified in step (a), so as to obtain peptide variant(s) associated with the mammalian tumor cell or the mammalian tumor tissue. Then the method further comprises selecting the peptide variant(s) from step b, which binds a T-cell receptor (TCR). This step comprises: i) selecting the peptide variant(s) with a pre-defined length; ii) characterizing the peptide variant(s) (e.g. in silico) by selecting and matching features associated with an amino acid at each position of the peptide with selected pre-defined features for each position of peptides recognized by TCR associated with either CD8+ T-cell or CD4+ T-cell, so as to obtain predictive ability of the peptide variant(s) to interact with the TCR; iii) selecting the peptide variant(s) above based on predicted ability of the peptide variant(s) to interact with the TCR, so as to be an immunogenic peptide that may or can serve as a mammalian tumor vaccine(s) after lengthening the selected immunogenic peptide variant(s) such that following vaccination the lengthened selected peptide variant(s) is taken up by antigen-presenting cells, processed to the size of the selected peptide variant(s) and displayed by antigen-presenting cells. The method further comprises forming a vaccine comprising the at least one immunogenic peptide so selected and administering the vaccine in an effective amount to the subject so as to treat the cancer in the subject.

For example, the cancer may be a stomach cancer, a colon cancer, a breast cancer, an ovarian cancer, a prostate cancer, a lung cancer, a kidney cancer, a gastric cancer, a testicular cancer, a head and neck cancer, a pancreatic cancer, a brain cancer, a melanoma, a lymphoma or a leukemia.

Immunogenic Peptides from Mutated or Altered Proteins in Mammalian Cancers

The invention further provides an immunogenic peptide composition prepared by this method of the invention. In one embodiment, the immunogenic peptide composition may further comprise at least one adjuvant.

The invention further provides a mammalian tumor vaccine selected by any of the methods of the invention.

The methods described herein in various embodiments comprise identifying immunogenic peptides of nine amino acids (9-mer) derived from mutations present in mammalian cancer tissues and cancer cell lines. In the context of this disclosure, immunogenic peptides are selected on the basis of: i) TCR binding; ii) HLA binding; iii) expression; iv) proteolytic processing; and v) peptide transporter binding. The method described in various embodiments was applied to 2.3 million unique cancer mutations captured from MedGenome's proprietary cancer mutation database OncoMD™ and a list of peptides restricted to class I HLA molecules consisting of HLA-A01:01, HLA-A02:0, HLA-A11:01, HLA-A24:02, HLA-B35:03, HLA-B40:06, HLA-B44:03, HLA-B51:01, HLA-B57:01, HLA-C06:02, HLA-C07:02, HLA-C12:03, HLA-C15:02 are identified (Table 1). In some embodiments, one or more of the 9-mer immunogenic peptide identified by the methods of the invention can be used following amino acid extension (addition) on amino-terminus and carboxyl-terminus, as a cancer vaccine and administered to cancer patients. In an embodiment, equal number of amino acids are added at each end of the 9-mer peptide identified by the methods of the invention, so as to permit cross presentation of the desired 9-mer immunogenic peptide. In some embodiments, the composition of a cancer vaccine may comprise of two or more immunogenic peptides. In some embodiments, cancer vaccines comprising of one, two or more immunogenic peptides may activate a cytotoxic T cell (CTL) response and a CD4 T cell response against one or two or more immunogenic peptides.

In some embodiments, the cancer vaccine composition may comprise of a 9-mer immunogenic peptide that may be part of a precursor protein, or part of longer peptides about >9 amino acids up to about 50 amino acids. In some embodiments, the cancer vaccine composition may comprise of two or more immunogenic peptides that may be part of one, two or more precursor proteins or part of one, two or more longer peptides about >9 amino acids up to about 50 amino acids. In some embodiments, the composition of the cancer vaccine may contain an adjuvant to help boost the immune response. In some embodiments, the composition of the cancer vaccine containing an adjuvant to help boost the immune response may be pharmaceutically acceptable.

In some embodiments, the cancer vaccine, or a precursor protein containing the cancer vaccine, or a longer peptide about >9 amino acids up to about 50 amino acids containing the cancer vaccine may be encoded by a nucleic acid sequence. In some embodiments, the nucleic acid sequence may be a DNA. In other embodiments, the nucleic acid sequence may be RNA. In some embodiments, the nucleic acid sequence may contain an adjuvant. In some embodiments, the nucleic acid sequence with the adjuvant may be used for treating the cancer patients.

In some embodiments, the nucleic acid sequence may be injected into mammalian cells to express the cancer vaccine in the form of a peptide, or as part of a protein precursor or as part of a longer peptide >9 amino acid up to about 50 amino acids to generate stable cells. In some embodiments, the stable cells may be primary cells, or cell lines derived from primary cells. In some embodiments, the primary cell may be derived from normal tissues or from cancer tissues.

In some embodiments, the stable cells may be used for screening antibodies by phage display technology. In some embodiments, the stable cells may be used in T cell activation screening assays.

Combination Therapy

In another embodiment, the peptides of the invention (e.g., single or multiple peptides of the invention) so obtained by the methods of selection of the invention may be administered in combination, or sequentially, with another therapeutic agent. Such other therapeutic agents include those known for treatment, prevention, or amelioration of one or more symptoms of cancer diseases and disorders. Such therapeutic agents include, but are not limited to, ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin, mitogellin, retstrictocin, phenomycin, enomycin, curicin, crotin, calicheamicin, *sapaonaria officinalis* inhibitor, maytansinoids, and glucocorticoid and other chemotherapeutic agents, as well as radioisotopes such as $^{212}$Bi, $^{131}$I, $^{131}$In, $^{90}$Y, and $^{186}$Re.

The peptides of the invention formulated into tumor or cancer vaccine(s) may also be used in combination, or sequentially, with one or more immune checkpoint inhibitors. Immune checkpoint inhibitors include inhibitors for PD-1, PD-L1, PD-L2, 4-1BB, 4-1BBL, HVEM, BTLA, CD160, CD226, LAG3, CTLA-4, B7-1, B7-2, CD40, CD40L, Galectin-9, TIM-3, GITR, GITRL, SIRP alpha, B7-H3, B7-H4, VISTA, OX40, OX-40L, CEACAM1, CD47, ICOS, ICOSL, TIGIT, IDO, CD28, LIGHT, TIGIT, CD155, CD70 and adenosine A2a receptor. Immune checkpoint inhibitor may be an antibody or an antibody fragment. The antibody or antibody fragment may be derived from a monoclonal antibody. In one embodiment, the monoclonal antibody or its fragment is human or humanized. Immune checkpoint inhibitor for PD-1 may be selected from any of MEDI0680 (also known as AMP-614; MedImmune/AstraZeneca), nivolumab (also known as Opdivo, BMS-936558, MDX-1106 and ONO-4538; Bristol-Myers Squibb and Ono Pharmaceuticals), pembrolizumab (also known as Keytruda, MK-3475 and lambrolizumab; Merck) and pidilizumab (also known as CT-011; CureTech). Immune checkpoint inhibitor for PD-L1 may be selected from any of BMS-936559 (also known as CT-011; Bristol-Myers Squibb), MEDI4736 (MedImmune/AstraZeneca), MPDL3280A (also known as RG7446; Genetech/Roche) and MSB0010718C (EMD Serono).

Kits

According to another aspect of the invention, kits are provided. Kits according to the invention include package(s) comprising antibodies or compositions of the invention.

The phrase "package" means any vessel containing peptides or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering peptides or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include antibodies in a solid phase or in a liquid phase (such as buffers provided) in a package. The kits also can include buffers for preparing solutions for conducting the methods, and pipettes for transferring liquids from one container to another.

The kit may optionally also contain one or more other agents for use in combination therapies as described herein. In certain embodiments, the package(s) is a container for intravenous administration. In other embodiments antibodies are provided in the form of a liposome.

The following examples serve to illustrate the present invention. These examples are in no way intended to limit the scope of the invention.

EXAMPLES

Example 1

Selecting Immunogenic Peptide from Variant Coding Sequence

This application provides a method to combine protein sequence-altering variant identification with methods to predict immunogenic peptides from mutated proteins. For example, in some embodiments the method provides immunogenic peptides from cancer tissues of an individual, where the individual can be mice or human.

Selection of immunogenic peptides comprises: a) selecting a set of cancer variants from mouse and human cancer cell lines and mouse and human cancer tissues where each variant in the genomic sequence correspond to both protein coding and protein non-coding sequences; b) variants of mouse cell lines and cancer tissues are identified by mouse whole exome and/or whole genome sequencing and variants from human cancer cell lines and human cancer tissues are identified by whole exome and/or whole genome sequencing; c) variants in mouse tissues and cell lines are identified by comparing with the reference sequence of mouse, and variants in human tissues and cell lines are identified by comparing with the reference sequence of human; d) variants are identified by comparing with the reference sequence, where the reference sequence is mouse reference sequence available in the public domain, or human reference sequence available in the public domain (e.g. current mouse reference sequence is (GRCm38/mm10) and current human reference sequence is (hg19)); e) variants from mouse tissues and cell lines include all genomic variants that alter the sequence of the RNA and the sequence of the protein translated from the RNA; f) variants from human tissues and cell lines include all genomic variants that alter the sequence of the proteins translated from the messenger RNA—protein variants; g) selecting the variants based on their expression in the mouse or human cell lines and tissues from the transcriptomic analysis; h) generating 8-11 amino acid peptides from the altered protein variants; and/or i) selecting a set of 8-11 amino acid immunogenic peptides from the previous step by predicting immunogenicity of the variant peptide comprising the altered amino acids encoded by the variant coding sequence; thereby selecting immunogenic peptides from altered or mutated proteins unique to cancer or tumor cells or tissues.

In some embodiments, cancer-specific mutant proteins are detected by sequencing DNA and RNA of all protein-coding genes encoded in mouse or human genome. In one embodiment, all protein coding genes are identified by whole exome sequencing (WES) or whole genome sequencing (WGS) The sequences are analyzed and taken through a series of steps shown in FIG. 1.

Brief description of the steps shown in FIG. 1 include the following.

Step 1 & 2 involve the use of MedGenome's next generation sequencing pipeline to identify genetic alterations at the DNA and RNA level.

Step 3 involves standard bioinformatic processing of next generation sequencing data to identify cancer-specific genetic alterations at the DNA and RNA level Steps 4-6 use MedGenome's variant calling pipeline to identify all variants and select those that pass the quality control metrics (Passed variants). Passed variant is identified based on:
1. Alignment
2. Read depth
3. Allele depth,
4. Overall quality of the variant.

Sequence variants can generate different classes of altered proteins: i. proteins altered in amino acid sequence in which one or more amino acids are altered, which may be arranged in a sequence or distributed randomly across the length of the protein; ii. proteins translated from fusion genes; iii. proteins produced from splice variants and from mutations in splicing sites, which results in the introduction of intronic region, or part of an intronic region, or alternatively, exclusion of an exon or part of an exon, in frame with the protein coding sequence; iv. Proteins produced from insertions and deletions of nucleotides that cause frameshift in the protein coding sequence resulting in the introduction of one or more amino acids absent in the normal protein; v. Protein arising from loss of stop codons (stop loss) that adds additional amino acids at the end of the protein. In some embodiments, tumor or cancer tissues from individuals comprise more than 1, 100, 1000, 2,000, or 6,000 different variant coding sequences resulting in changes in amino acid(s) in the protein as compared to the reference sample.

Step 7 applies further selection by considering variants that are expressed in the cancer tissue using the transcript data from RNA sequencing. The RNA sequence data is analyzed using MedGenome's RNA analysis pipeline to identify expressed variants, identify splice variants, frameshift variants and fusion genes. The pipeline defines expression as ≥1 FPKM (1 fragment per kilobase per million).

Step 8 compiles a list of all the expressed variants that will result in the generation of altered proteins. These altered proteins are likely to be absent in normal tissues and are cancer specific. A variant is considered expressed if it has a value ≥1 FPKM. Fusion genes are identified when regions from two different genes are fused to each other, and are present as part of a transcript. The fusion gene is considered expressed if the fusion region has a value ≥1 FPKM Step 9 generates peptides used in in silico TCR-binding analysis. Binding of TCRs to peptides occur when peptides are in complex with class-I or class-II HLA molecules. Class I HLA binds 8-11-mer peptides and Class II HLA binds 13-21 mer peptides. Our algorithm generates two sets of peptides for each mutation, one containing the non-mutated (wild-type) amino acid and the other corresponding to the mutant amino acid. The length of the peptide can vary from 8-mer to 21-mer. The algorithm automatically generates two sets of peptide libraries in which the wild-type or the mutant amino acid occupy each of the positions across the length of the peptide. For example, if a peptide is 9-mer long, the algorithm generates 9 wild-type peptides and 9 mutant peptides for in silico binding analysis by moving the mutant amino acid to each of the 9 positions in the peptide by a sliding window method.

Step 10 uses a novel algorithm that we have developed to identify immunogenic peptides that have a higher likelihood of eliciting a T-cell response. Peptides interact with TCR only if they are bound to the HLA molecule. The TCR interaction depends on the conformation of the peptide, the availability of amino acids that make contacts with the residues on the TCR, and the type of interactions that are made between residues on the peptide and the residues on the TCR. Our new method integrates information from sequence and structure of the peptides to model the TCR interaction and has been tested on gold standard datasets. The method may be computational or in silico.

Step 11 determines the binding affinity of both the wild-type and the mutant peptides with Class I or Class II HLA molecules. Mutant peptides with lower binding score are generally consider as strong binder to HLA molecule. After binding prediction, three groups of peptides are selected:
1. High affinity binding peptides—≤500 nM
2. Medium affinity binding peptides—>500 nM-≤1000 nM
3. Low affinity binding peptides—>1000 nM peptides Step 12 screens peptides for optimal processing to identify proteasomal and/or immunoproteasomal processing sites around the peptide, with the objective of prioritizing peptides in which the processing sites are optimally located, such that upon processing, the correct size peptide is produced. This step is important because the class I and class II HLA molecules bind peptides of a particular length. Class I HLA binds peptides from 8-11 mer and Class II HLA binds peptides that are 13-21 mer. We have devised our own scoring method that takes into account the presence of processing sites at the N and C-terminal ends of the peptide. When both sites are optimally located a maximum score of 20 is given. The score decreases as the processing sites are shifted away from the optimal location. A score >10 is used to select peptides for the next step. Peptides that are scored higher than 10 either by the proteasomal or by the immunoproteasomal cleavage are selected.

Step 14 calculates the transporter (TAP) binding affinity of the peptides. In order for the peptide to bind HLA molecule, the peptide needs to be transported from cytosol to endoplasmic reticulum. In this step, we perform the analysis to identify whether the peptide is delivered to HLA molecule by TAP. Any peptide exhibiting a TAP-binding score of <0.5 are selected for the final step of prioritization.

Predicting Immunogenic Peptides by their Ability to Bind TCRs

Figure 2:
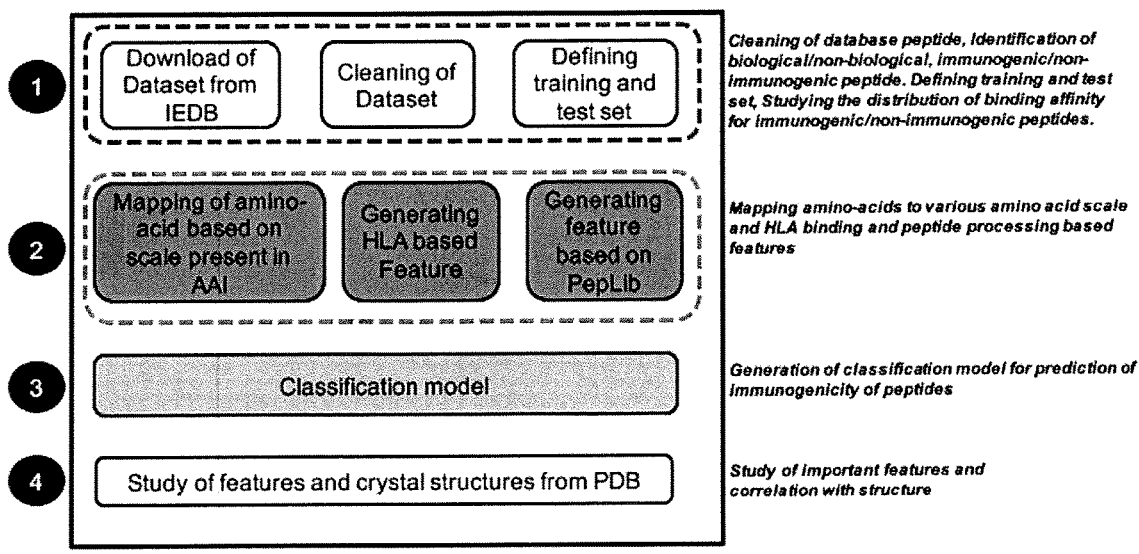
FIG. 2. Steps for the creation of classification models for predicting TCR-binding peptides derived from normal and cancer tissues.

The prediction of TCR-binding peptide prediction involves four different steps: 1. Data set creation; 2. Feature creation; 3. Classification model; 4. Study of features. The steps are shown in FIG. 2. A brief description of each step:
1. Dataset creation: In this step, we have first collected peptide and its immunogenicity status from IEDB database. After this we then performed processing of the peptides to have a clean dataset for the model building exercise. Further, we have generated several training and test instances for model building and performance evaluation.

2. Feature creation: In this step, various amino acid features, HLA binding and peptide processing related feature is generated for the peptides.
3. Classification model: In this step, classification model is generated using feature matrix. This step involves: feature selection, identification of classification method, scoring of the peptides.
4. Study of features: The important features are studied in detail and its correlation with peptide structure/interactions in crystal structure is also studied in this step.

Data Preparation

The sequence, assay, HLA type, publication id (PMID), and immunogenicity information of the peptide was downloaded from IEDB database (Release 24 Nov. 2016). The database contains immunogenicity status for 2,521 unique 9-mer peptides for human. The peptide is first categorized into self and foreign peptide. The peptides generated by human body are known as self, while those that do not originate in human body are called non-self or foreign peptides. Of the total peptides, ~85% of them belong to foreign peptide category. The peptides are also classified based on assay that was performed to check its immunogenicity. Although there are several assay types, we have broadly grouped them into biological and non-biological type. Majority of the peptides (~90%) are assayed by biological type. Before using these peptides, we apply the following filters to focus on unambiguous assay prediction and for which the information as per our requirement is complete.

Biological assay filter: The peptides predicted as immunogenic/non-immunogenic using one of the biological assay is taken further for the analysis.

Prediction by assays: There are many peptides which are predicted as both immunogenic and non-immunogenic using one or more different assays. These peptides were removed from our analysis.

4-digit HLA information: The peptides for which 4-digit information is available for the HLA type is considered for further analysis. Of the total peptides, for 1075 peptides 4-digit HLA information was available Overall, we obtain 1,075 peptides for which unambiguous immunogenicity and HLA 4-digit information is complete. The classification model was built using 307 immunogenic peptides (Table 8) and 167 non-immunogenic peptides (Table 9). These peptides bind HLA-A02:01.

Figure 3:
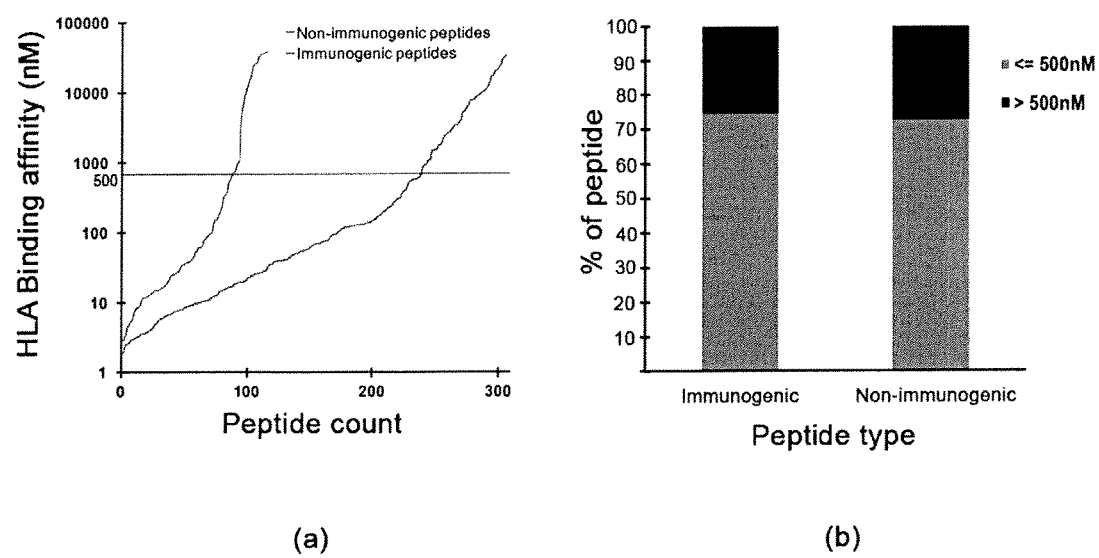
FIG. 3a-b. (a) Binding affinity distribution of immunogenic and non-immunogenic peptides, (b) Distribution of peptide with >=500 nM and <500 nM.

Currently the binding affinity of the peptide is considered as the main criteria to select immunogenic peptides. In general, binding affinity by standard programs such as NetMHCcons [24] with <=500 nM is taken as cutoff to define immunogenic peptides. The distribution of binding affinity for the HLA-A*02:01 peptides is shown in FIG. 3. If we consider <=500 nM as cutoff to define immunogenic peptides then the sensitivity is 74.5% whereas the specificity is only 27.6%. FIG. 3B demonstrates that HLA binding does not predict immunogenic peptides because both non-immunogenic and immunogenic peptides can bind HLA with high affinity (FIG. 3B).

Feature Construction and Selection

In order to generate features that will discriminate the TCR-binding peptides from the non-binders, we analyzed the physico-chemical composition of the amino acids and their positional biases in the 9-mer peptides that interact with TCR when bound to the HLA molecule. We analyzed 58 crystal structure data of TCR-HLA-peptide complex to identify binding interactions that existed at each position of the 9-mer peptide and the HLA at one hand and the TCR on the other. A summary of the feature types is provided below:

I. Physicochemical Features:

An amino acid is an organic molecule with an amino group (—NH2) and a carboxyl group (—COOH). We obtained the physicochemical features from following two different sources.

AAindex: AAindex is a database that contains numerical representation for various physicochemical and biochemical properties of amino acids and pairs of amino acids. We used AAindex1 for our feature creation. Most of the defined indices belong to 4 major cluster—(i) α-helix and turn propensities, (ii) β-strand propensity, (iii) hydrophobicity and (v) physicochemical properties. A total of 566 different AAindex1 scale was obtained from this database (May 18, 2017). We use the following strategy to generate features.

$AAIF_1$: The value of AAindex1 scale for peptide position #1.

$AAIF_2$: The value of AAindex1 scale for peptide position #2.

$AAIF_3$: The value of AAindex1 scale for peptide position #3.

$AAIF_4$: The value of AAindex1 scale for peptide position #4.

$AAIF_5$: The value of AAindex1 scale for peptide position #5.

$AAIF_6$: The value of AAindex1 scale for peptide position #6.

$AAIF_7$: The value of AAindex1 scale for peptide position #7.

$AAIF_8$: The value of AAindex1 scale for peptide position #8.

$AAIF_9$: The value of AAindex1 scale for peptide position #9.

$AAIF_{1-2}$: The average value of AAindex1 scale for peptide position #1 and #2.

$AAIF_{2-3}$: The average value of AAindex1 scale for peptide position #2 and #3.

$AAIF_{3-4}$: The average value of AAindex1 scale for peptide position #3 and #4.

$AAIF_{4-5}$: The average value of AAindex1 scale for peptide position #4 and #5.

$AAIF_{5-6}$: The average value of AAindex1 scale for peptide position #5 and #6.

$AAIF_{6-7}$: The average value of AAindex1 scale for peptide position #6 and #7.

$AAIF_{7-8}$: The average value of AAindex1 scale for peptide position #7 and #8.

$AAIF_{8-9}$: The average value of AAindex1 scale for peptide position #8 and #9.

$AAIF_{3-8}$: The average value of AAindex1 scale from peptide position #3 to position #8.

$AAIF_{1-9}$: The average value of AAindex1 scale from peptide position #1 to position #9.

Overall, we generated 11,300 features from AAindex.

PepLib: Peplib is a R package that can be used to calculate the descriptors for each amino acid of given peptide sequence. These descriptors include counts of groups (polar, acidic, basic, aromatic etc.), molecular weight, number of rotatable bonds and charged based partial surface area descriptors. There are 53 variables to be calculated for each amino acid in the peptide sequence. Some of these descriptors are based on permutation of descriptors calculated on single amino acid. Along with the descriptors calculated for each amino acid, Peplib provides the values at sequence level also. Sequence level calculation involves three types of the descriptors—1. mean 2. variance and 3. autocorrelation function of the descriptors for each sequence.

II. HLA Binding Feature:

Prediction of HLA binding affinity score is the most important feature of the peptide that is being currently used by community to identify candidate T cell epitopes. Binding affinity of <=500 nM is routinely used as a threshold for peptide selection. We have generated NetMHCcons binding affinity score as one of the feature for each peptide. NetMHCcons is a consensus based method of three different state-of-the-art MHC-peptide binding prediction methods (NetMHC, NetMHCpan and PickPocket) with peptides. NetMHCcons uses artificial neural network-based method give result as IC50 values trained on data from various MHC alleles and positional specific scoring matrices [24].

III. Peptide Processing Features:

NetChop: Peptide cleavage is an important step for making sure that the peptide is generated for the transportation and then presentation by HLA molecule. We have used the IEDB NetChop 3.1 program [25] to identify the cleavage sites. NetChop is a neural network prediction based method for prediction of cleavage sires of the human proteasome. We generate two different features for each peptide—(a) C-term which is trained with the database consisting of publicly available MHC class I ligands using C-terminal cleavage sites of ligand into consideration, (b) 20S which is trained with the in vitro degradation data.

TAP processing: The TAP processing includes the neural network based estimation of ability of transportation of cleaved peptides by TAP transporter proteins to the endoplasmic reticulum. The neural network is trained on the in vitro experiments characterizing the sequence specificity of TAP transport. In total, six features based on TAP were generated for each of the peptides.

Overall, from the total peptides 307 immunogenic and 116 non-immunogenic peptides that bind HLA-A*02:01, we generated 12,094 total features.

Classification Model

Figure 4:
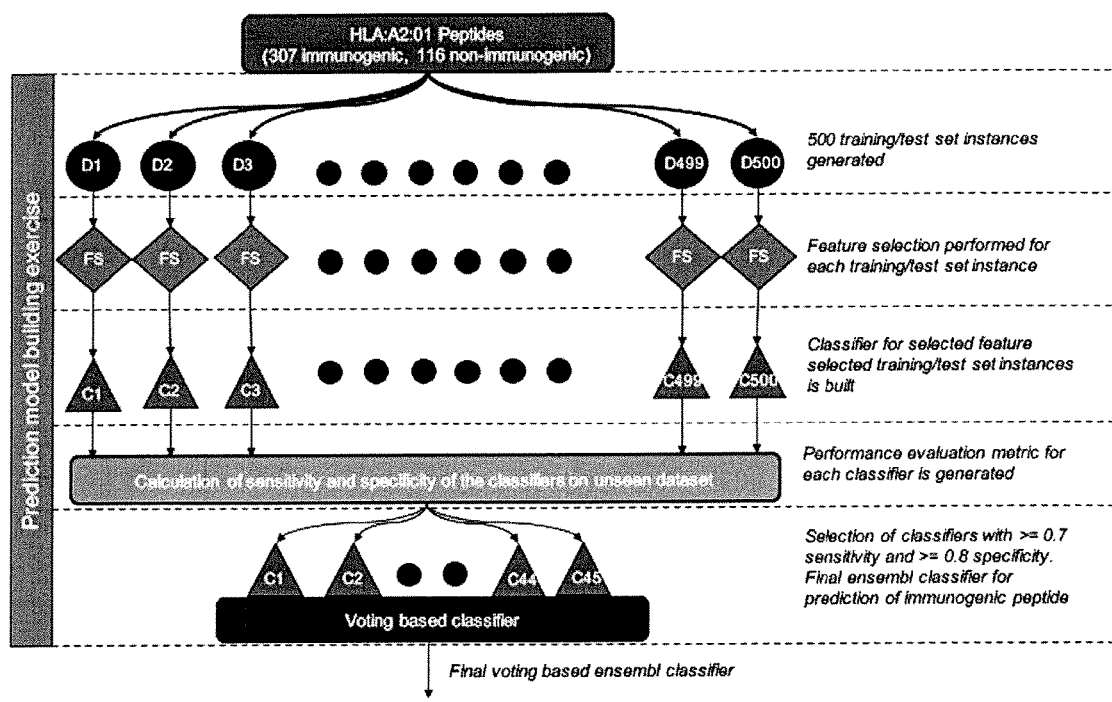
FIG. 4. A schematic of the steps used for creating the classification models to separate TCR-binding peptides (immunogenic) from those that did not bind TCR (non-immunogenic).

We performed the following steps to generate the classification model for predicting immunogenicity of the peptides as shown in FIG. 4.

Creation of training and test set instances: Due to unbalanced dataset of immunogenic and non-immunogenic peptides (3:1) in our study, we first generated 500 different instances of the complete dataset which had balanced number of immunogenic and non-immunogenic peptides. Each balanced dataset consists of ~100 immunogenic and non-immunogenic peptides. The balance dataset is generated to avoid overfitting of classification model to either immunogenic or non-immunogenic peptide class.

Figure 5:
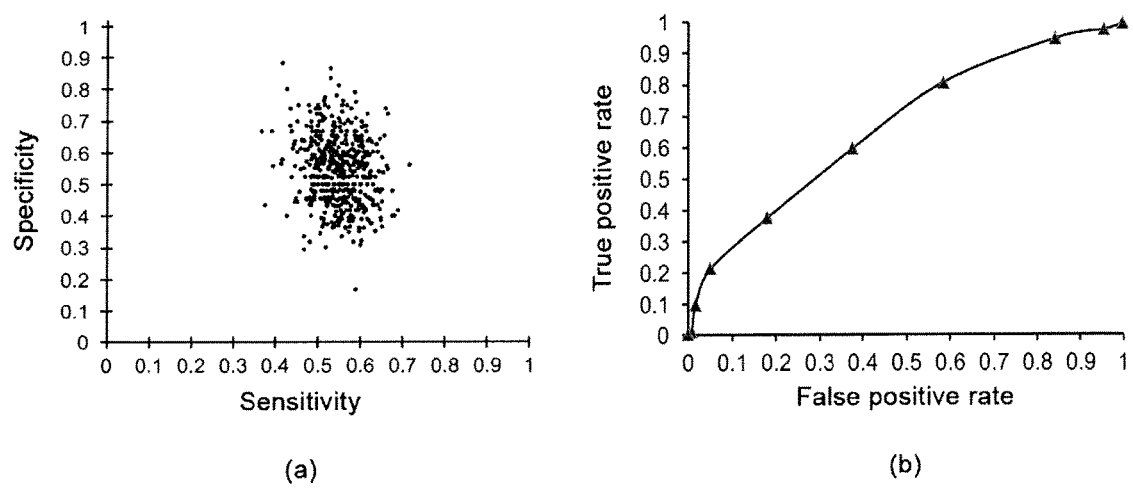
FIG. 5a-b. (a) Sensitivity and specificity of the 500 training/test instances using J4.8 classification approach, (b) ROC curve from the ensemble classifier.

Feature selection: We generated classification model using all 12,094 features for 500 training/test instances. Ensemble classifier is generated by combining the results from all classifier instances. Equal weight is given to each of the classifier instance. If >50% of classifier predict a peptide as immunogenic then the prediction of the ensemble classifier is taken as immunogenic otherwise prediction is taken as non-immunogenic. The sensitivity and specificity of J4.8 classifier for the 500 instances is shown in FIG. 5A. The ROC curve of the ensemble classifier is shown in FIG. 5B. The ROC curve is generated by changing the cutoff/threshold of ensemble classifier for predicting a peptide as immunogenic or non-immunogenic.

Feature reduction: As a next step, we performed feature reduction for each 500 instances using CfsSubsetEval method available in Weka machine learning toolkit [26]. This method evaluates the worth of a subset of attributes by considering the individual predictive ability of each feature along with the degree of redundancy between them. During feature selection, some of the training instance failed to converge, hence, we were left with 433 training instances. A median of 45 features were selected for each training instance. Overall, 3680 features were selected when all 433 training instances were included. Of these 60% (2219) of the features were part of 2 or more training instances. Using the reduced 433 training instances a new classification model was built.

Figure 6:
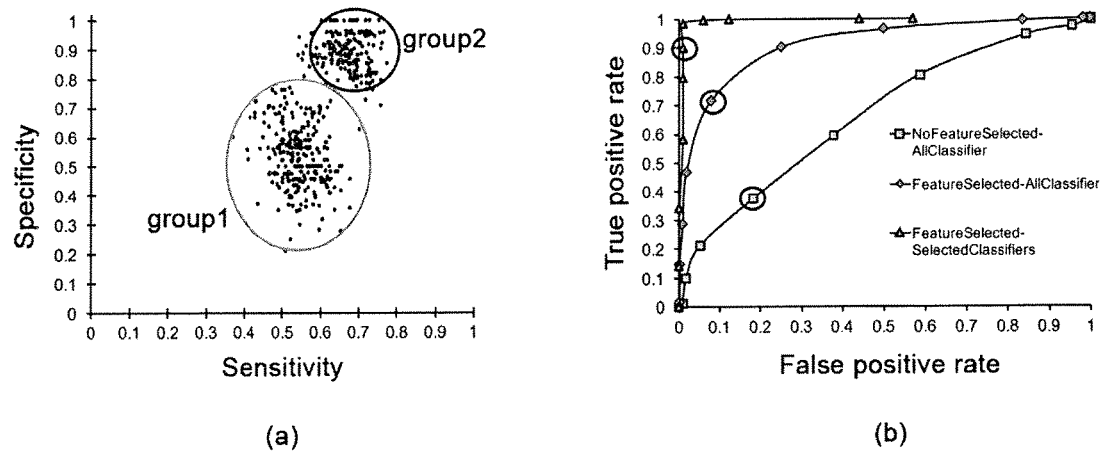
FIG. 6a-b. (a) Sensitivity and specificity of the 433 classifier instances using J4.8 classification approach, (b) The ROC curve for the 433 classifiers (colored in RED), 45 classifiers (colored in Blue).

Performance evaluation of classifier instances: The reduced features for each training instances was trained using J4.8 classification system. We first created an ensemble classifier by combining the prediction from all 433 classifier instances. A sensitivity/specificity plot using 3680 features clearly separates the classifier instances into two groups (FIG. 6A). The Group-2 classifier instances have higher sensitivity and specificity as compared to Group-1 classifier instances (FIG. 6A). We used voting based approach to classify the peptide sequence into immunogenic and non-immunogenic class. For an input peptide if >50% of the classifiers predicts it as immunogenic then the peptide is classified as immunogenic otherwise the peptide is defined as non-immunogenic peptide. ROC curve of 433 classifier instances (Ensemble classifier2) performs better than using 500 classifier instances (Ensemble classifier1) (FIG. 6B).

In the next step, we selected classifier instances for which >=75% sensitivity and >=80% specificity on unseen dataset was observed. We found 45 such classifier instances. An ensemble classifier was created using the 45 classifiers. ROC curve of 45 classifier instances (Ensemble classifier3) is shown in FIG. 6B.

Performance evaluation of the three ensemble classifiers on unseen dataset is shown in Table 10. Ensemble3 classifier provides sensitivity and specificity of 90.23% and 99.14% respectively, which is significantly higher than the HLA binding affinity of the peptides. Table 10 demonstrates that the HLA binding affinity, which is currently used as an important criterion for selecting immunogenic peptides carry a high false positive rate.

Figure 7:
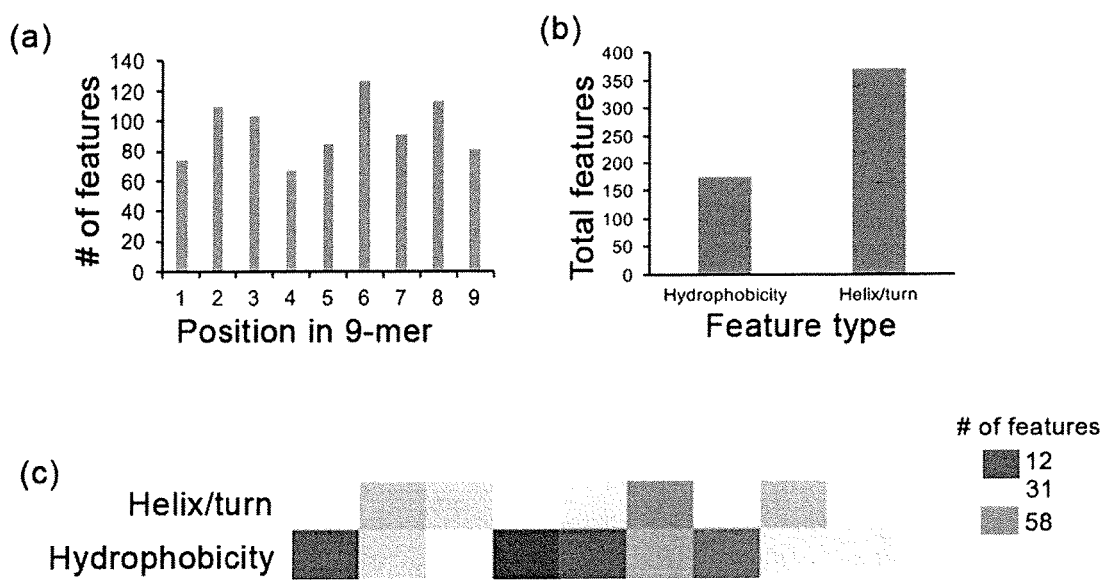
FIG. 7a-c. Features to identify selected peptides. (a) Number of features that define occupancy of amino acids at each position of the 9-mer peptide. (b) Number of features that define hydrophobicity and helix/turn properties of amino acids. (c) Enrichment of amino acids with helix-turn and hydrophobicity properties at each position of the 9-mer peptides.
Figure 8:
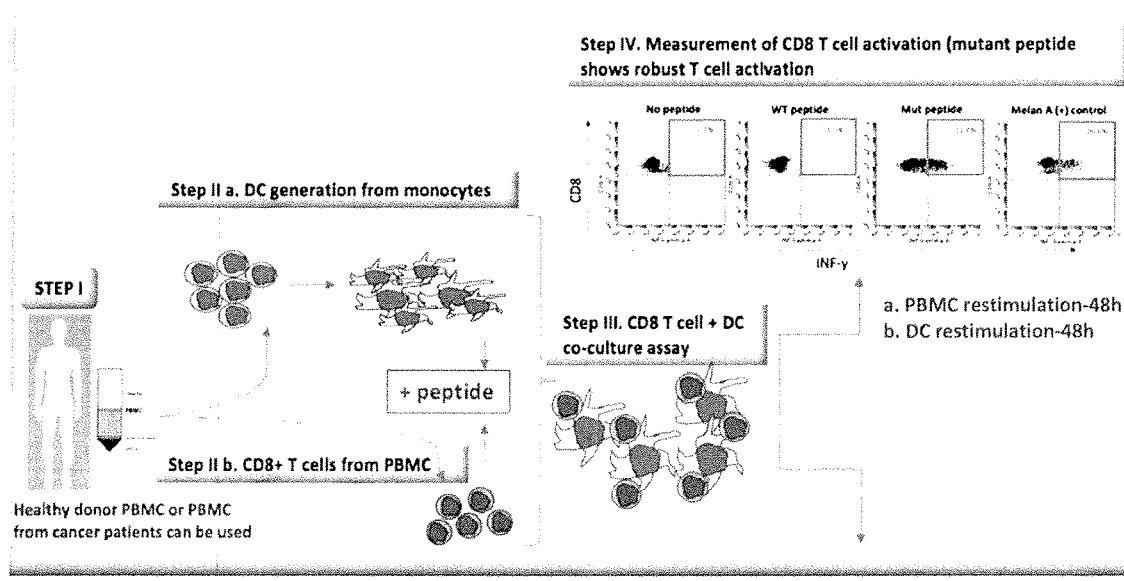
FIG. 8. Shows a schematic representation of the assay.
Figure 9:
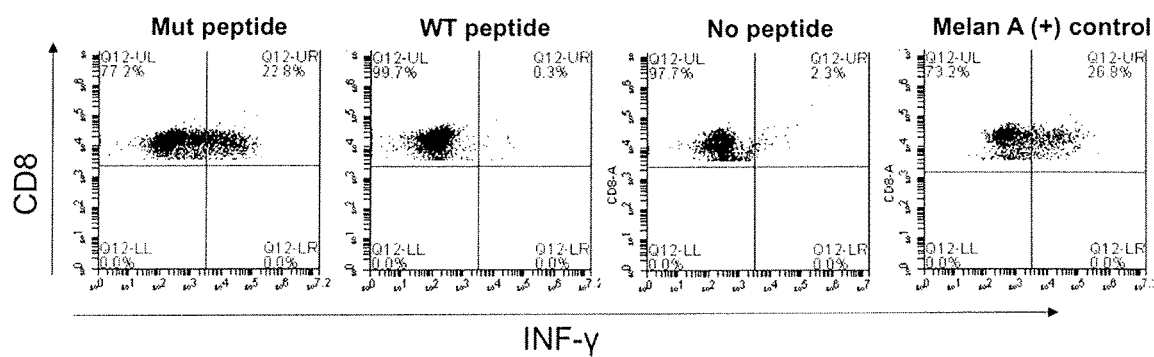
FIG. 9. The data presented here shows a validated neoantigen restricted to HLA-A*02.01 as evidenced by elevated levels of CD8 T cell activation markers, INF-γ and CD69 in flow cytometric based assays. Naïve human CD8 T cells specific for the HLA-A*02.01-restricted epitopes showed a positive response to a colorectal cancer derived mutant peptide over a wild-type (control) peptide when stimulated with peptide-pulsed allogeneic DCs. Melan-A (26-35 L, positive control) is used as a positive control.

Frequently occurring features at each position of the 9-mer peptide was computed from Ensemble3 classifier and shown in FIG. 7. Names of features defining hydrophobic and helix/turn properties of amino acids are shown in Table 11.

TABLE 1

Cancer vaccines from recurrently occurring mutations across human cancers

| | | | | |
|---|---|---|---|---|
| LQVDQLWDV (SEQ ID NO.: 1) | SDAYPSAFP (SEQ ID NO.: 19) | YPVQRLPFS (SEQ ID NO.: 37) | GSVSFGTVY (SEQ ID NO.: 55) | TGQATPLPV (SEQ ID NO.: 73) |
| RTFCLLVVV (SEQ ID NO.: 2) | RQGRQRRVR (SEQ ID NO.: 20) | RWLLVSSPP (SEQ ID NO.: 38) | VQGRVPTLE (SEQ ID NO.: 56) | AFWRSLLAC (SEQ ID NO.: 74) |
| QLREASPWV (SEQ ID NO.: 3) | LLRQGRQRR (SEQ ID NO.: 21) | FWRSLLACC (SEQ ID NO.: 39) | PQARAVHLP (SEQ ID NO.: 57) | YSTMVFLPW (SEQ ID NO.: 75) |
| CLLVVVVV (SEQ ID NO.: 4) | VGQRIGSVS (SEQ ID NO.: 22) | VVVVFAVCW (SEQ ID NO.: 40) | LSRPGLLRQ (SEQ ID NO.: 58) | VDQLWDVLL (SEQ ID NO.: 76) |
| FCLLVVVV (SEQ ID NO.: 5) | VGRSVAIGP (SEQ ID NO.: 23) | TCNSRQAAL (SEQ ID NO.: 41) | LREASPWVR (SEQ ID NO.: 59) | RPQLRRWLL (SEQ ID NO.: 77) |
| PIYMYSTMV (SEQ ID NO.: 6) | ELHSLWTCD (SEQ ID NO.: 24) | PVQRLPFST (SEQ ID NO.: 42) | RPEVRKTAS (SEQ ID NO.: 60) | LQLREASPW (SEQ ID NO.: 78) |
| LVVVVVFA (SEQ ID NO.: 7) | SPWVRPRRR (SEQ ID NO.: 25) | ALSRPGLLR (SEQ ID NO.: 43) | LHGRADLIR (SEQ ID NO.: 61) | HSLWTCDCE (SEQ ID NO.: 79) |
| TAFWRSLLA (SEQ ID NO.: 8) | PLPGRIEVR (SEQ ID NO.: 26) | EPIYMYSTM (SEQ ID NO.: 44) | QGRVPTLER (SEQ ID NO.: 62) | LPGRIEVRT (SEQ ID NO.: 80) |
| QLWDVLLSR (SEQ ID NO.: 9) | TPEVQGRVP (SEQ ID NO.: 27) | VVGRSVAIG (SEQ ID NO.: 45) | HDPQARAVH (SEQ ID NO.: 63) | LWDVLLSRE (SEQ ID NO.: 81) |
| VQRLPFSTV (SEQ ID NO.: 10) | PWVRPRRRL (SEQ ID NO.: 28) | HGRADLIRL (SEQ ID NO.: 46) | PGLLRQGRQ (SEQ ID NO.: 64) | EVQGRVPTL (SEQ ID NO.: 82) |
| PQLR.RWLLV (SEQ ID NO.: 11) | VVVVVVFAV (SEQ ID NO.: 29) | SGVGKSALT (SEQ ID NO.: 47) | IGSVSFGTV (SEQ ID NO.: 65) | ATVTAFWRS (SEQ ID NO.: 83) |
| LLVVVVVF (SEQ ID NO.: 12) | WLLVSSPPS (SEQ ID NO.: 30) | RYPVQRLPF (SEQ ID NO.: 48) | VVVVVFAVC (SEQ ID NO.: 66) | QVDQLWDVL (SEQ ID NO.: 84) |
| TFCLLVVVV (SEQ ID NO.: 13) | LVVGRSVAI (SEQ ID NO.: 31) | DLIRLLLKH (SEQ ID NO.: 49) | VHLPELLSL (SEQ ID NO.: 67) | ASDAYPSAF (SEQ ID NO.: 85) |
| GQATPLPVT (SEQ ID NO.: 14) | RIGSVSFGT (SEQ ID NO.: 32) | ADLIRLLLK (SEQ ID NO.: 50) | QLRRWLLVS (SEQ ID NO.: 68) | DGLVVGRSV (SEQ ID NO.: 86) |
| TMRPLPGRI (SEQ ID NO.: 15) | RADLIRLLL (SEQ ID NO.: 33) | LHSLWTCDC (SEQ ID NO.: 51) | GQRIGSVSF (SEQ ID NO.: 69) | SGELHSLWT (SEQ ID NO.: 87) |
| VLLSRELFR (SEQ ID NO.: 16) | TVGQRIGSV (SEQ ID NO.: 34) | VAIGPREQW (SEQ ID NO.: 52) | GELHSLWTC (SEQ ID NO.: 70) | DQLWDVLLS (SEQ ID NO.: 88) |
| QATPLPVTI (17) | RTPEVQGRV (SEQ ID NO.: 35) | LIRLLLKHG (SEQ ID NO.: 53) | RTMRPLPGR (SEQ ID NO.: 71) | FQDHKPKIS (SEQ ID NO.: 89) |
| IYMYSTMVF (SEQ ID NO.: 18) | RSLLACCQL (SEQ ID NO.: 36) | SATVTAFWR (SEQ ID NO.: 54) | MYSTMVFLP (SEQ ID NO.: 72) | |

TABLE 2

HLA Class I: List of HLA class I alleles

| HLA A | #of subtypes | HLA B | #of subtypes | HLA C | #of subtypes |
|---|---|---|---|---|---|
| HLA-A01 | 52 | HLA-B07 | 111 | HLA-C01 | 38 |
| HLA-A02 | 247 | HLA-B08 | 58 | HLA-C02 | 37 |
| HLA-A03 | 76 | HLA-B13 | 35 | HLA-C03 | 92 |
| HLA-A11 | 60 | HLA-B14 | 17 | HLA-C04 | 65 |
| HLA-A23 | 22 | HLA-B15 | 189 | HLA-C05 | 43 |
| HLA-A24 | 128 | HLA-B18 | 47 | HLA-C06 | 43 |
| HLA-A25 | 12 | HLA-B27 | 64 | HLA-C07 | 141 |
| HLA-A26 | 47 | HLA-B35 | 137 | HLA-C08 | 34 |
| HLA-A29 | 21 | HLA-B37 | 21 | HLA-C12 | 41 |
| HLA-A30 | 37 | HLA-B38 | 23 | HLA-C14 | 18 |
| HLA-A31 | 36 | HLA-B39 | 56 | HLA-C15 | 32 |
| HLA-A32 | 23 | HLA-B40 | 128 | HLA-C16 | 23 |
| HLA-A33 | 30 | | | HLA-C17 | 7 |
| HLA-A34 | 8 | | | HLA-C18 | 3 |
| HLA-A36 | 5 | | | | |
| HLA-A43 | 1 | | | | |
| HLA-A66 | 15 | | | | |
| HLA-A68 | 51 | | | | |
| HLA-A69 | 1 | | | | |
| HLA-A74 | 12 | | | | |
| HLA-A80 | 2 | | | | |

TABLE 3

HLA Class II: List of HLA class II alleles available in netMHCcons tool for analysis

| HLA DR | HLA DQ | HLA DP |
|---|---|---|
| HLA-DRB1*01:01 | HLA-DQA1*05:01/DQB1*02:01 | HLA-DPA1*02:01/DPB1*01:01 |
| HLA-DRB1*03:01 | HLA-DQA1*05:01/DQB1*03:01 | HLA-DPA1*01:03/DPB1*02:01 |
| HLA-DRB1*04:01 | HLA-DQA1*03:01/DQB1*03:02 | HLA-DPA1*01/DPB1*04:01 |
| HLA-DRB1*04:05 | HLA-DQA1*04:01/DQB1*04:02 | HLA-DPA1*03:01/DPB1*04:02 |
| HLA-DRB1*07:01 | HLA-DQA1*01:01/DQB1*05:01 | HLA-DPA1*02:01/DPB1*05:01 |
| HLA-DRB1*08:02 | HLA-DQA1*01:02/DQB1*06:02 | HLA-DPA1*02:01/DPB1*14:01 |
| HLA-DRB1*09:01 | | |
| HLA-DRB1*11:01 | | |
| HLA-DRB1*12:01 | | |
| HLA-DRB1*13:02 | | |
| HLA-DRB1*15:01 | | |
| HLA-DRB3*01:01 | | |
| HLA-DRB3*02:02 | | |
| HLA-DRB4*01:01 | | |
| HLA-DRB5*01:01 | | |

**In the case of class I molecules, beta-chain (i.e. beta-2 microglobulin) is fixed while alpha-chain is variable. Hence, class I molecules are named based on their alpha-chains. In contrast, both alpha and beta-chains of class II molecules can vary. Thus, names of the two chains are needed to specify a class II molecules (e.g. HLA-DPA1*01:03/HLA-DPB1*02:01). For DR locus however, alpha chains are not variable. Hence, names for DR molecules use only those of the beta-chain (e.g. HLA-DRB1*01:01).

TABLE 4

List of HLA-A subtypes against which binding affinity of peptides can be calculated

| | | | | | | | | |
|---|---|---|---|---|---|---|---|---|
| HLA-A01:01 | HLA-A02:54 | HLA-A02:162 | HLA-A03:02 | HLA-A11:27 | HLA-A24:53 | HLA-A26:04 | HLA-A30:40 | HLA-A36:02 |
| HLA-A01:02 | HLA-A02:55 | HLA-A02:163 | HLA-A03:04 | HLA-A11:29 | HLA-A24:54 | HLA-A26:05 | HLA-A30:41 | HLA-A36:03 |
| HLA-A01:03 | HLA-A02:56 | HLA-A02:164 | HLA-A03:05 | HLA-A11:30 | HLA-A24:55 | HLA-A26:06 | HLA-A31:01 | HLA-A36:04 |
| HLA-A01:06 | HLA-A02:57 | HLA-A02:165 | HLA-A03:06 | HLA-A11:31 | HLA-A24:56 | HLA-A26:07 | HLA-A31:02 | HLA-A36:05 |
| HLA-A01:07 | HLA-A02:58 | HLA-A02:166 | HLA-A03:07 | HLA-A11:32 | HLA-A24:57 | HLA-A26:08 | HLA-A31:03 | HLA-A43:01 |
| HLA-A01:08 | HLA-A02:59 | HLA-A02:167 | HLA-A03:08 | HLA-A11:33 | HLA-A24:58 | HLA-A26:09 | HLA-A31:04 | HLA-A66:01 |
| HLA-A01:09 | HLA-A02:60 | HLA-A02:168 | HLA-A03:09 | HLA-A11:34 | HLA-A24:59 | HLA-A26:10 | HLA-A31:05 | HLA-A66:02 |
| HLA-A01:10 | HLA-A02:61 | HLA-A02:169 | HLA-A03:10 | HLA-A11:35 | HLA-A24:61 | HLA-A26:12 | HLA-A31:06 | HLA-A66:03 |
| HLA-A01:12 | HLA-A02:62 | HLA-A02:170 | HLA-A03:12 | HLA-A11:36 | HLA-A24:62 | HLA-A26:13 | HLA-A31:07 | HLA-A66:04 |
| HLA-A01:13 | HLA-A02:63 | HLA-A02:171 | HLA-A03:13 | HLA-A11:37 | HLA-A24:63 | HLA-A26:14 | HLA-A31:08 | HLA-A66:05 |
| HLA-A01:14 | HLA-A02:64 | HLA-A02:172 | HLA-A03:14 | HLA-A11:38 | HLA-A24:64 | HLA-A26:15 | HLA-A31:09 | HLA-A66:06 |
| HLA-A01:17 | HLA-A02:65 | HLA-A02:173 | HLA-A03:15 | HLA-A11:39 | HLA-A24:66 | HLA-A26:16 | HLA-A31:10 | HLA-A66:07 |
| HLA-A01:19 | HLA-A02:66 | HLA-A02:174 | HLA-A03:16 | HLA-A11:40 | HLA-A24:67 | HLA-A26:17 | HLA-A31:11 | HLA-A66:08 |
| HLA-A01:20 | HLA-A02:67 | HLA-A02:175 | HLA-A03:17 | HLA-A11:41 | HLA-A24:68 | HLA-A26:18 | HLA-A31:12 | HLA-A66:09 |

TABLE 4-continued

List of HLA-A subtypes against which binding affinity of peptides can be calculated

| | | | | | | | | |
|---|---|---|---|---|---|---|---|---|
| HLA-A01:21 | HLA-A02:68 | HLA-A02:176 | HLA-A03:18 | HLA-A11:42 | HLA-A24:69 | HLA-A26:19 | HLA-A31:13 | HLA-A66:10 |
| HLA-A01:23 | HLA-A02:69 | HLA-A02:177 | HLA-A03:19 | HLA-A1 1:43 | HLA-A24:70 | HLA-A26:20 | HLA-A31:15 | HLA-A66:11 |
| HLA-A01:24 | HLA-A02:70 | HLA-A02:178 | HLA-A03:20 | HLA-A11:44 | HLA-A24:71 | HLA-A26:21 | HLA-A31:16 | HLA-A66:12 |
| HLA-A01:25 | HLA-A02:71 | HLA-A02:179 | HLA-A03:22 | HLA-A11:45 | HLA-A24:72 | HLA-A26:22 | HLA-A31:17 | HLA-A66:13 |
| HLA-A01:26 | HLA-A02:72 | HLA-A02:180 | HLA-A03:23 | HLA-A11:46 | HLA-A24:73 | HLA-A26:23 | HLA-A31:18 | HLA-A66:14 |
| HLA-A01:28 | HLA-A02:73 | HLA-A02:181 | HLA-A03:24 | HLA-A11:47 | HLA-A24:74 | HLA-A26:24 | HLA-A31:19 | HLA-A66:15 |
| HLA-A01:29 | HLA-A02:74 | HLA-A02:182 | HLA-A03:25 | HLA-A11:48 | HLA-A24:75 | HLA-A26:26 | HLA-A31:20 | HLA-A68:01 |
| HLA-A01:30 | HLA-A02:75 | HLA-A02:183 | HLA-A03:26 | HLA-A11:49 | HLA-A24:76 | HLA-A26:27 | HLA-A31:21 | HLA-A68:02 |
| HLA-A01:32 | HLA-A02:76 | HLA-A02:184 | HLA-A03:27 | HLA-A11:51 | HLA-A24:77 | HLA-A26:28 | HLA-A31:22 | HLA-A68:03 |
| HLA-A01:33 | HLA-A02:77 | HLA-A02:185 | HLA-A03:28 | HLA-A11:53 | HLA-A24:78 | HLA-A26:29 | HLA-A31:23 | HLA-A68:04 |
| HLA-A01:35 | HLA-A02:78 | HLA-A02:186 | HLA-A03:29 | HLA-A11:54 | HLA-A24:79 | HLA-A26:30 | HLA-A31:24 | HLA-A68:05 |
| HLA-A01:36 | HLA-A02:79 | HLA-A02:187 | HLA-A03:30 | HLA-A11:55 | HLA-A24:80 | HLA-A26:31 | HLA-A31:25 | HLA-A68:06 |
| HLA-A01:37 | HLA-A02:80 | HLA-A02:188 | HLA-A03:31 | HLA-A11:56 | HLA-A24:81 | HLA-A26:32 | HLA-A31:26 | HLA-A68:07 |
| HLA-A01:38 | HLA-A02:81 | HLA-A02:189 | HLA-A03:32 | HLA-A11:57 | HLA-A24:82 | HLA-A26:33 | HLA-A31:27 | HLA-A68:08 |
| HLA-A01:39 | HLA-A02:84 | HLA-A02:190 | HLA-A03:33 | HLA-A11:58 | HLA-A24:85 | HLA-A26:34 | HLA-A31:28 | HLA-A68:09 |
| HLA-A01:40 | HLA-A02:85 | HLA-A02:191 | HLA-A03:34 | HLA-A11:59 | HLA-A24:87 | HLA-A26:35 | HLA-A31:29 | HLA-A68:10 |
| HLA-A01:41 | HLA-A02:86 | HLA-A02:192 | HLA-A03:35 | HLA-A11:60 | HLA-A24:88 | HLA-A26:36 | HLA-A31:30 | HLA-A68:12 |
| HLA-A01:42 | HLA-A02:87 | HLA-A02:193 | HLA-A03:37 | HLA-A11:61 | HLA-A24:89 | HLA-A26:37 | HLA-A31:31 | HLA-A68:13 |
| HLA-A01:43 | HLA-A02:89 | HLA-A02:194 | HLA-A03:38 | HLA-A11:62 | HLA-A24:91 | HLA-A26:38 | HLA-A31:32 | HLA-A68:14 |
| HLA-A01:44 | HLA-A02:90 | HLA-A02:195 | HLA-A03:39 | HLA-A11:63 | HLA-A24:92 | HLA-A26:39 | HLA-A31:33 | HLA-A68:15 |
| HLA-A01:45 | HLA-A02:91 | HLA-A02:196 | HLA-A03:40 | HLA-A11:64 | HLA-A24:93 | HLA-A26:40 | HLA-A31:34 | HLA-A68:16 |
| HLA-A01:46 | HLA-A02:92 | HLA-A02:197 | HLA-A03:41 | HLA-A23:01 | HLA-A24:94 | HLA-A26:41 | HLA-A31:35 | HLA-A68:17 |
| HLA-A01:47 | HLA-A02:93 | HLA-A02:198 | HLA-A03:42 | HLA-A23:02 | HLA-A24:95 | HLA-A26:42 | HLA-A31:36 | HLA-A68:19 |
| HLA-A01:48 | HLA-A02:95 | HLA-A02:199 | HLA-A03:43 | HLA-A23:03 | HLA-A24:96 | HLA-A26:43 | HLA-A31:37 | HLA-A68:20 |
| HLA-A01:49 | HLA-A02:96 | HLA-A02:200 | HLA-A03:44 | HLA-A23:04 | HLA-A24:97 | HLA-A26:45 | HLA-A32:01 | HLA-A68:21 |
| HLA-A01:50 | HLA-A02:97 | HLA-A02:201 | HLA-A03:45 | HLA-A23:05 | HLA-A24:98 | HLA-A26:46 | HLA-A32:02 | HLA-A68:22 |
| HLA-A01:51 | HLA-A02:99 | HLA-A02:202 | HLA-A03:46 | HLA-A23:06 | HLA-A24:99 | HLA-A26:47 | HLA-A32:03 | HLA-A68:23 |
| HLA-A01:54 | HLA-A02:101 | HLA-A02:203 | HLA-A03:47 | HLA-A23:09 | HLA-A24:100 | HLA-A26:48 | HLA-A32:04 | HLA-A68:24 |
| HLA-A01:55 | HLA-A02:102 | HLA-A02:204 | HLA-A03:48 | HLA-A23:10 | HLA-A24:101 | HLA-A26:49 | HLA-A32:05 | HLA-A68:25 |
| HLA-A01:58 | HLA-A02:103 | HLA-A02:205 | HLA-A03:49 | HLA-A23:12 | HLA-A24:102 | HLA-A26:50 | HLA-A32:06 | HLA-A68:26 |
| HLA-A01:59 | HLA-A02:104 | HLA-A02:206 | HLA-A03:50 | HLA-A23:13 | HLA-A24:103 | HLA-A29:01 | HLA-A32:07 | HLA-A68:27 |
| HLA-A01:60 | HLA-A02:105 | HLA-A02:207 | HLA-A03:51 | HLA-A23:14 | HLA-A24:104 | HLA-A29:02 | HLA-A32:08 | HLA-A68:28 |
| HLA-A01:61 | HLA-A02:106 | HLA-A02:208 | HLA-A03:52 | HLA-A23:15 | HLA-A24:105 | HLA-A29:03 | HLA-A32:09 | HLA-A68:29 |
| HLA-A01:62 | HLA-A02:107 | HLA-A02:209 | HLA-A03:53 | HLA-A23:16 | HLA-A24:106 | HLA-A29:04 | HLA-A32:10 | HLA-A68:30 |
| HLA-A01:63 | HLA-A02:108 | HLA-A02:210 | HLA-A03:54 | HLA-A23:17 | HLA-A24:107 | HLA-A29:05 | HLA-A32:12 | HLA-A68:31 |
| HLA-A01:64 | HLA-A02:109 | HLA-A02:211 | HLA-A03:55 | HLA-A23:18 | HLA-A24:108 | HLA-A29:06 | HLA-A32:13 | HLA-A68:32 |
| HLA-A01:65 | HLA-A02:110 | HLA-A02:212 | HLA-A03:56 | HLA-A23:20 | HLA-A24:109 | HLA-A29:07 | HLA-A32:14 | HLA-A68:33 |
| HLA-A01:66 | HLA-A02:111 | HLA-A02:213 | HLA-A03:57 | HLA-A23:21 | HLA-A24:110 | HLA-A29:09 | HLA-A32:15 | HLA-A68:34 |
| HLA- | HLA- | HLA- | HLA- | HLA- | HLA- | HLA- | HLA- | HLA- |

TABLE 4-continued

List of HLA-A subtypes against which binding affinity of peptides can be calculated

| | | | | | | | | |
|---|---|---|---|---|---|---|---|---|
| A02:01 | A02:112 | A02:214 | A03:58 | A23:22 | A24:111 | A29:10 | A32:16 | A68:35 |
| HLA- | HLA- | HLA- | HLA- | HLA- | HLA- | HLA- | HLA- | HLA- |
| A02:02 | A02:114 | A02:215 | A03:59 | A23:23 | A24:112 | A29:11 | A32:17 | A68:36 |
| HLA- | HLA- | HLA- | HLA- | HLA- | HLA- | HLA- | HLA- | HLA- |
| A02:03 | A02:115 | A02:216 | A03:60 | A23:24 | A24:113 | A29:12 | A32:18 | A68:37 |
| HLA- | HLA- | HLA- | HLA- | HLA- | HLA- | HLA- | HLA- | HLA- |
| A02:04 | A02:116 | A02:217 | A03:61 | A23:25 | A24:114 | A29:13 | A32:20 | A68:38 |
| HLA- | HLA- | HLA- | HLA- | HLA- | HLA- | HLA- | HLA- | HLA- |
| A02:05 | A02:117 | A02:218 | A03:62 | A23:26 | A24:115 | A29:14 | A32:21 | A68:39 |
| HLA- | HLA- | HLA- | HLA- | HLA- | HLA- | HLA- | HLA- | HLA- |
| A02:06 | A02:118 | A02:219 | A03:63 | A24:02 | A24:116 | A29:15 | A32:22 | A68:40 |
| HLA- | HLA- | HLA- | HLA- | HLA- | HLA- | HLA- | HLA- | HLA- |
| A02:07 | A02:119 | A02:220 | A03:64 | A24:03 | A24:117 | A29:16 | A32:23 | A68:41 |
| HLA- | HLA- | HLA- | HLA- | HLA- | HLA- | HLA- | HLA- | HLA- |
| A02:08 | A02:120 | A02:221 | A03:65 | A24:04 | A24:118 | A29:17 | A32:24 | A68:42 |
| HLA- | HLA- | HLA- | HLA- | HLA- | HLA- | HLA- | HLA- | HLA- |
| A02:09 | A02:121 | A02:224 | A03:66 | A24:05 | A24:119 | A29:18 | A32:25 | A68:43 |
| HLA- | HLA- | HLA- | HLA- | HLA- | HLA- | HLA- | HLA- | HLA- |
| A02:10 | A02:122 | A02:228 | A03:67 | A24:06 | A24:120 | A29:19 | A33:01 | A68:44 |
| HLA- | HLA- | HLA- | HLA- | HLA- | HLA- | HLA- | HLA- | HLA- |
| A02:11 | A02:123 | A02:229 | A03:70 | A24:07 | A24:121 | A29:20 | A33:03 | A68:45 |
| HLA- | HLA- | HLA- | HLA- | HLA- | HLA- | HLA- | HLA- | HLA- |
| A02:12 | A02:124 | A02:230 | A03:71 | A24:08 | A24:122 | A29:21 | A33:04 | A68:46 |
| HLA- | HLA- | HLA- | HLA- | HLA- | HLA- | HLA- | HLA- | HLA- |
| A02:13 | A02:126 | A02:231 | A03:72 | A24:10 | A24:123 | A29:22 | A33:05 | A68:47 |
| HLA- | HLA- | HLA- | HLA- | HLA- | HLA- | HLA- | HLA- | HLA- |
| A02:14 | A02:127 | A02:232 | A03:73 | A24:13 | A24:124 | A30:01 | A33:06 | A68:48 |
| HLA- | HLA- | HLA- | HLA- | HLA- | HLA- | HLA- | HLA- | HLA- |
| A02:16 | A02:128 | A02:233 | A03:74 | A24:14 | A24:125 | A30:02 | A33:07 | A68:50 |
| HLA- | HLA- | HLA- | HLA- | HLA- | HLA- | HLA- | HLA- | HLA- |
| A02:17 | A02:129 | A02:234 | A03:75 | A24:15 | A24:126 | A30:03 | A33:08 | A68:51 |
| HLA- | HLA- | HLA- | HLA- | HLA- | HLA- | HLA- | HLA- | HLA- |
| A02:18 | A02:130 | A02:235 | A03:76 | A24:17 | A24:127 | A30:04 | A33:09 | A68:52 |
| HLA- | HLA- | HLA- | HLA- | HLA- | HLA- | HLA- | HLA- | HLA- |
| A02:19 | A02:131 | A02:236 | A03:77 | A24:18 | A24:128 | A30:06 | A33:10 | A68:53 |
| HLA- | HLA- | HLA- | HLA- | HLA- | HLA- | HLA- | HLA- | HLA- |
| A02:20 | A02:132 | A02:237 | A03:78 | A24:19 | A24:129 | A30:07 | A33:11 | A68:54 |
| HLA- | HLA- | HLA- | HLA- | HLA- | HLA- | HLA- | HLA- | HLA- |
| O2:21 | A02:133 | A02:238 | A03:79 | A24:20 | A24:130 | A30:08 | A33:12 | A69:01 |
| HLA- | HLA- | HLA- | HLA- | HLA- | HLA- | HLA- | HLA- | HLA- |
| A02:22 | A02:134 | A02:239 | A03:80 | A24:21 | A24:131 | A30:09 | A33:13 | A74:01 |
| HLA- | HLA- | HLA- | HLA- | HLA- | HLA- | HLA- | HLA- | HLA- |
| A02:24 | A02:135 | A02:240 | A03:81 | A24:22 | A24:133 | A30:10 | A33:14 | A74:02 |
| HLA- | HLA- | HLA- | HLA- | HLA- | HLA- | HLA- | HLA- | HLA- |
| A02:25 | A02:136 | A02:241 | A03:82 | A24:23 | A24:134 | A30:11 | A33:15 | A74:03 |
| HLA- | HLA- | HLA- | HLA- | HLA- | HLA- | HLA- | HLA- | HLA- |
| A02:26 | A02:137 | A02:242 | A11:01 | A24:24 | A24:135 | A30:12 | A33:16 | A74:04 |
| HLA- | HLA- | HLA- | HLA- | HLA- | HLA- | HLA- | HLA- | HLA- |
| A02:27 | A02:138 | A02:243 | A11:02 | A24:25 | A24:136 | A30:13 | A33:17 | A74:05 |
| HLA- | HLA- | HLA- | HLA- | HLA- | HLA- | HLA- | HLA- | HLA- |
| A02:28 | A02:139 | A02:244 | A11:03 | A24:26 | A24:137 | A30:15 | A33:18 | A74:06 |
| HLA- | HLA- | HLA- | HLA- | HLA- | HLA- | HLA- | HLA- | HLA- |
| A02:29 | A02:140 | A02:245 | A11:04 | A24:27 | A24:138 | A30:16 | A33:19 | A74:07 |
| HLA- | HLA- | HLA- | HLA- | HLA- | HLA- | HLA- | HLA- | HLA- |
| A02:30 | A02:141 | A02:246 | A11:05 | A24:28 | A24:139 | A30:17 | A33:20 | A74:08 |
| HLA- | HLA- | HLA- | HLA- | HLA- | HLA- | HLA- | HLA- | HLA- |
| A02:31 | A02:142 | A02:247 | A11:06 | A24:29 | A24:140 | A30:18 | A33:21 | A74:09 |
| HLA- | HLA- | HLA- | HLA- | HLA- | HLA- | HLA- | HLA- | HLA- |
| A02:33 | A02:143 | A02:248 | A11:07 | A24:30 | A24:141 | A30:19 | A33:22 | A74:10 |
| HLA- | HLA- | HLA- | HLA- | HLA- | HLA- | HLA- | HLA- | HLA- |
| A02:34 | A02:144 | A02:249 | A11:08 | A24:31 | A24:142 | A30:20 | A33:23 | A74:11 |
| HLA- | HLA- | HLA- | HLA- | HLA- | HLA- | HLA- | HLA- | HLA- |
| A02:35 | A02:145 | A02:251 | A11:09 | A24:32 | A24:143 | A30:22 | A33:24 | A74:13 |
| HLA- | HLA- | HLA- | HLA- | HLA- | HLA- | HLA- | HLA- | HLA- |
| A02:36 | A02:146 | A02:252 | Al 1:10 | A24:33 | A24:144 | A30:23 | A33:25 | A80:01 |
| HLA- | HLA- | HLA- | HLA- | HLA- | HLA- | HLA- | HLA- | HLA- |
| A02:37 | A02:147 | A02:253 | A11:11 | A24:34 | A25:01 | A30:24 | A33:26 | A80:02 |
| HLA- | HLA- | HLA- | HLA- | HLA- | HLA- | HLA- | HLA- | |
| A02:38 | A02:148 | A02:254 | A11:12 | A24:35 | A25:02 | A30:25 | A33:27 | |
| HLA- | HLA- | HLA- | HLA- | HLA- | HLA- | HLA- | HLA- | |
| A02:39 | A02:149 | A02:255 | A11:13 | A24:37 | A25:03 | A30:26 | A33:28 | |
| HLA- | HLA- | HLA- | HLA- | HLA- | HLA- | HLA- | HLA- | |
| A02:40 | A02:150 | A02:256 | A11:14 | A24:38 | A25:04 | A30:28 | A33:29 | |
| HLA- | HLA- | HLA- | HLA- | HLA- | HLA- | HLA- | HLA- | |
| A02:41 | A02:151 | A02:257 | A11:15 | A24:39 | A25:05 | A30:29 | A33:30 | |
| HLA- | HLA- | HLA- | HLA- | HLA- | HLA- | HLA- | HLA- | |
| A02:42 | A02:152 | A02:258 | A11:16 | A24:41 | A25:06 | A30:30 | A33:31 | |

TABLE 4-continued

List of HLA-A subtypes against which binding affinity of peptides can be calculated

| HLA-A02:44 | HLA-A02:153 | HLA-A02:259 | HLA-A11:17 | HLA-A24:42 | HLA-A25:07 | HLA-A30:31 | HLA-A34:01 |
| HLA-A02:45 | HLA-A02:154 | HLA-A02:260 | HLA-A11:18 | HLA-A24:43 | HLA-A25:08 | HLA-A30:32 | HLA-A34:02 |
| HLA-A02:46 | HLA-A02:155 | HLA-A02:261 | HLA-A11:19 | HLA-A24:44 | HLA-A25:09 | HLA-A30:33 | HLA-A34:03 |
| HLA-A02:47 | HLA-A02:156 | HLA-A02:262 | HLA-A11:20 | HLA-A24:46 | HLA-A25:10 | HLA-A30:34 | HLA-A34:04 |
| HLA-A02:48 | HLA-A02:157 | HLA-A02:263 | HLA-A11:22 | HLA-A24:47 | HLA-A25:11 | HLA-A30:35 | HLA-A34:05 |
| HLA-A02:49 | HLA-A02:158 | HLA-A02:264 | HLA-A11:23 | HLA-A24:49 | HLA-A25:13 | HLA-A30:36 | HLA-A34:06 |
| HLA-A02:50 | HLA-A02:159 | HLA-A02:265 | HLA-A11:24 | HLA-A24:50 | HLA-A26:01 | HLA-A30:37 | HLA-A34:07 |
| HLA-A02:51 | HLA-A02:160 | HLA-A02:266 | HLA-A11:25 | HLA-A24:51 | HLA-A26:02 | HLA-A30:38 | HLA-A34:08 |
| HLA-A02:52 | HLA-A02:161 | HLA-A03:01 | HLA-A11:26 | HLA-A24:52 | HLA-A26:03 | HLA-A30:39 | HLA-A36:01 |

TABLE 5

List of HLA-B subtypes against which binding affinity of peptides are calculated

| HLA-B07:02 | HLA-B07:103 | HLA-B13:35 | HLA-B15:84 | HLA-B15:192 | HLA-B27:44 | HLA-B35:83 | HLA-B38:21 | B40:45 |
| HLA-B07:03 | HLA-B07:104 | HLA-B13:36 | HLA-B15:85 | HLA-B15:193 | HLA-B27:45 | HLA-B35:84 | HLA-B38:22 | HLA-B40:46 |
| HLA-B07:04 | HLA-B07:105 | HLA-B13:37 | HLA-B15:86 | HLA-B15:194 | HLA-B27:46 | HLA-B35:85 | HLA-B38:23 | HLA-B40:47 |
| HLA-B07:05 | HLA-B07:106 | HLA-B13:38 | HLA-B15:87 | HLA-B15:195 | HLA-B27:47 | HLA-B35:86 | HLA-B39:01 | HLA-B40:48 |
| HLA-B07:06 | HLA-B07:107 | HLA-B13:39 | HLA-B15:88 | HLA-B15:196 | HLA-B27:48 | HLA-B35:87 | HLA-B39:02 | HLA-B40:49 |
| HLA-B07:07 | HLA-B07:108 | HLA-B14:01 | HLA-B15:89 | HLA-B15:197 | HLA-B27:49 | HLA-B35:88 | HLA-B39:03 | HLA-B40:50 |
| HLA-B07:08 | HLA-B07:109 | HLA-B14:02 | HLA-B15:90 | HLA-B15:198 | HLA-B27:50 | HLA-B35:89 | HLA-B39:04 | HLA-B40:51 |
| HLA-B07:09 | HLA-B07:110 | HLA-B14:03 | HLA-B15:91 | HLA-B15:199 | HLA-B27:51 | HLA-B35:90 | HLA-B39:05 | HLA-B40:52 |
| HLA-B07:10 | HLA-B07:112 | HLA-B14:04 | HLA-B15:92 | HLA-B15:200 | HLA-B27:52 | HLA-B35:91 | HLA-B39:06 | HLA-B40:53 |
| HLA-B07:11 | HLA-B07:113 | HLA-B14:05 | HLA-B15:93 | HLA-B15:201 | HLA-B27:53 | HLA-B35:92 | HLA-B39:07 | HLA-B40:54 |
| HLA-B07:12 | HLA-B07:114 | HLA-B14:06 | HLA-B15:95 | HLA-B15:202 | HLA-B27:54 | HLA-B35:93 | HLA-B39:08 | HLA-B40:55 |
| HLA-B07:13 | HLA-B07:115 | HLA-B14:08 | HLA-B15:96 | HLA-B18:01 | HLA-B27:55 | HLA-B35:94 | HLA-B39:09 | HLA-B40:56 |
| HLA-B07:14 | HLA-B08:01 | HLA-B14:09 | HLA-B15:97 | HLA-B18:02 | HLA-B27:56 | HLA-B35:95 | HLA-B39:10 | HLA-B40:57 |
| HLA-B07:15 | HLA-B08:02 | HLA-B14:10 | HLA-B15:98 | HLA-B18:03 | HLA-B27:57 | HLA-B35:96 | HLA-B39:11 | HLA-B40:58 |
| HLA-B07:16 | HLA-B08:03 | HLA-B14:11 | HLA-B15:99 | HLA-B18:04 | HLA-B27:58 | HLA-B35:97 | HLA-B39:12 | HLA-B40:59 |
| HLA-B07:17 | HLA-B08:04 | HLA-B14:12 | HLA-B15:101 | HLA-B18:05 | HLA-B27:60 | HLA-B35:98 | HLA-B39:13 | HLA-B40:60 |
| HLA-B07:18 | HLA-B08:06 | HLA-B14:13 | HLA-B15:102 | HLA-B18:06 | HLA-B27:61 | HLA-B35:99 | HLA-B39:14 | HLA-B40:61 |
| HLA-B07:19 | HLA-B08:07 | HLA-B14:14 | HLA-B15:103 | HLA-B18:07 | HLA-B27:62 | HLA-B35:100 | HLA-B39:15 | HLA-B40:62 |
| HLA-B07:20 | HLA-B08:09 | HLA-B14:15 | HLA-B15:104 | HLA-B18:08 | HLA-B27:63 | HLA-B35:101 | HLA-B39:16 | HLA-B40:63 |
| HLA-B07:21 | HLA-B08:10 | HLA-B14:16 | HLA-B15:105 | HLA-B18:09 | HLA-B27:67 | HLA-B35:102 | HLA-B39:17 | HLA-B40:64 |
| HLA-B07:22 | HLA-B08:11 | HLA-B14:17 | HLA-B15:106 | HLA-B18:10 | HLA-B27:68 | HLA-B35:103 | HLA-B39:18 | HLA-B40:65 |
| HLA-B07:23 | HLA-B08:12 | HLA-B14:18 | HLA-B15:107 | HLA-B18:11 | HLA-B27:69 | HLA-B35:104 | HLA-B39:19 | HLA-B40:66 |
| HLA-B07:24 | HLA-B08:13 | HLA-B15:01 | HLA-B15:108 | HLA-B18:12 | HLA-B35:01 | HLA-B35:105 | HLA-B39:20 | HLA-B40:67 |
| HLA-B07:25 | HLA-B08:14 | HLA-B15:02 | HLA-B15:109 | HLA-B18:13 | HLA-B35:02 | HLA-B35:106 | HLA-B39:22 | HLA-B40:68 |
| HLA-B07:26 | HLA-B08:15 | HLA-B15:03 | HLA-B15:110 | HLA-B18:14 | HLA-B35:03 | HLA-B35:107 | HLA-B39:23 | HLA-B40:69 |

TABLE 5-continued

List of HLA-B subtypes against which binding affinity of peptides are calculated

| | | | | | | | | |
|---|---|---|---|---|---|---|---|---|
| HLA-B07:27 | HLA-B08:16 | HLA-B15:04 | HLA-B15:112 | HLA-B18:15 | HLA-B35:04 | HLA-B35:108 | HLA-B39:24 | HLA-B40:70 |
| HLA-B07:28 | HLA-B08:17 | HLA-B15:05 | HLA-B15:113 | HLA-B18:18 | HLA-B35:05 | HLA-B35:109 | HLA-B39:26 | HLA-B40:71 |
| HLA-B07:29 | HLA-B08:18 | HLA-B15:06 | HLA-B15:114 | HLA-B18:19 | HLA-B35:06 | HLA-B35:110 | HLA-B39:27 | HLA-B40:72 |
| HLA-B07:30 | HLA-B08:20 | HLA-B15:07 | HLA-B15:115 | HLA-B18:20 | HLA-B35:07 | HLA-B35:111 | HLA-B39:28 | HLA-B40:73 |
| HLA-B07:31 | HLA-B08:21 | HLA-B15:08 | HLA-B15:116 | HLA-B18:21 | HLA-B35:08 | HLA-B35:112 | HLA-B39:29 | HLA-B40:74 |
| HLA-B07:32 | HLA-B08:22 | HLA-B15:09 | HLA-B15:117 | HLA-B18:22 | HLA-B35:09 | HLA-B35:113 | HLA-B39:30 | HLA-B40:75 |
| HLA-B07:33 | HLA-B08:23 | HLA-B15:10 | HLA-B15:118 | HLA-B18:24 | HLA-B35:10 | HLA-B35:114 | HLA-B39:31 | HLA-B40:76 |
| HLA-B07:34 | HLA-B08:24 | HLA-B15:11 | HLA-B15:119 | HLA-B18:25 | HLA-B35:11 | HLA-B35:115 | HLA-B39:32 | HLA-B40:77 |
| HLA-B07:35 | HLA-B08:25 | HLA-B15:12 | HLA-B15:120 | HLA-B18:26 | HLA-B35:12 | HLA-B35:116 | HLA-B39:33 | HLA-B40:78 |
| HLA-B07:36 | HLA-B08:26 | HLA-B15:13 | HLA-B15:121 | HLA-B18:27 | HLA-B35:13 | HLA-B35:117 | HLA-B39:34 | HLA-B40:79 |
| HLA-B07:37 | HLA-B08:27 | HLA-B15:14 | HLA-B15:122 | HLA-B18:28 | HLA-B35:14 | HLA-B35:118 | HLA-B39:35 | HLA-B40:80 |
| HLA-B07:38 | HLA-B08:28 | HLA-B15:15 | HLA-B15:123 | HLA-B18:29 | HLA-B35:15 | HLA-B35:119 | HLA-B39:36 | HLA-B40:81 |
| HLA-B07:39 | HLA-B08:29 | HLA-B15:16 | HLA-B15:124 | HLA-B18:30 | HLA-B35:16 | HLA-B35:120 | HLA-B39:37 | HLA-B40:82 |
| HLA-B07:40 | HLA-B08:31 | HLA-B15:17 | HLA-B15:125 | HLA-B18:31 | HLA-B35:17 | HLA-B35:121 | HLA-B39:39 | HLA-B40:83 |
| HLA-B07:41 | HLA-B08:32 | HLA-B15:18 | HLA-B15:126 | HLA-B18:32 | HLA-B35:18 | HLA-B35:122 | HLA-B39:41 | HLA-B40:84 |
| HLA-B07:42 | HLA-B08:33 | HLA-B15:19 | HLA-B15:127 | HLA-B18:33 | HLA-B35:19 | HLA-B35:123 | HLA-B39:42 | HLA-B40:85 |
| HLA-B07:43 | HLA-B08:34 | HLA-B15:20 | HLA-B15:128 | HLA-B18:34 | HLA-B35:20 | HLA-B35:124 | HLA-B39:43 | HLA-B40:86 |
| HLA-B07:44 | HLA-B08:35 | HLA-B15:21 | HLA-B15:129 | HLA-B18:35 | HLA-B35:21 | HLA-B35:125 | HLA-B39:44 | HLA-B40:87 |
| HLA-B07:45 | HLA-B08:36 | HLA-B15:23 | HLA-B15:131 | HLA-B18:36 | HLA-B35:22 | HLA-B35:126 | HLA-B39:45 | HLA-B40:88 |
| HLA-B07:46 | HLA-B08:37 | HLA-B15:24 | HLA-B15:132 | HLA-B18:37 | HLA-B35:23 | HLA-B35:127 | HLA-B39:46 | HLA-B40:89 |
| HLA-B07:47 | HLA-B08:38 | HLA-B15:25 | HLA-B15:133 | HLA-B18:38 | HLA-B35:24 | HLA-B35:128 | HLA-B39:47 | HLA-B40:90 |
| HLA-B07:48 | HLA-B08:39 | HLA-B15:27 | HLA-B15:134 | HLA-B18:39 | HLA-B35:25 | HLA-B35:131 | HLA-B39:48 | HLA-B40:91 |
| HLA-B07:50 | HLA-B08:40 | HLA-B15:28 | HLA-B15:135 | HLA-B18:40 | HLA-B35:26 | HLA-B35:132 | HLA-B39:49 | HLA-B40:92 |
| HLA-B07:51 | HLA-B08:41 | HLA-B15:29 | HLA-B15:136 | HLA-B18:41 | HLA-B35:27 | HLA-B35:133 | HLA-B39:50 | HLA-B40:93 |
| HLA-B07:52 | HLA-B08:42 | HLA-B15:30 | HLA-B15:137 | HLA-B18:42 | HLA-B35:28 | HLA-B35:135 | HLA-B39:51 | HLA-B40:94 |
| HLA-B07:53 | HLA-B08:43 | HLA-B15:31 | HLA-B15:138 | HLA-B18:43 | HLA-B35:29 | HLA-B35:136 | HLA-B39:52 | HLA-B40:95 |
| HLA-B07:54 | HLA-B08:44 | HLA-B15:32 | HLA-B15:139 | HLA-B18:44 | HLA-B35:30 | HLA-B35:137 | HLA-B39:53 | HLA-B40:96 |
| HLA-B07:55 | HLA-B08:45 | HLA-B15:33 | HLA-B15:140 | HLA-B18:45 | HLA-B35:31 | HLA-B35:138 | HLA-B39:54 | HLA-B40:97 |
| HLA-B07:56 | HLA-B08:46 | HLA-B15:34 | HLA-B15:141 | HLA-B18:46 | HLA-B35:32 | HLA-B35:139 | HLA-B39:55 | HLA-B40:98 |
| HLA-B07:57 | HLA-B08:47 | HLA-B15:35 | HLA-B15:142 | HLA-B18:47 | HLA-B35:33 | HLA-B35:140 | HLA-B39:56 | HLA-B40:99 |
| HLA-B07:58 | HLA-B08:48 | HLA-B15:36 | HLA-B15:143 | HLA-B18:48 | HLA-B35:34 | HLA-B35:141 | HLA-B39:57 | HLA-B40:100 |
| HLA-B07:59 | HLA-B08:49 | HLA-B15:37 | HLA-B15:144 | HLA-B18:49 | HLA-B35:35 | HLA-B35:142 | HLA-B39:58 | HLA-B40:101 |
| HLA-B07:60 | HLA-B08:50 | HLA-B15:38 | HLA-B15:145 | HLA-B18:50 | HLA-B35:36 | HLA-B35:143 | HLA-B39:59 | HLA-B40:102 |
| HLA-B07:61 | HLA-B08:51 | HLA-B15:39 | HLA-B15:146 | HLA-B27:01 | HLA-B35:37 | HLA-B35:144 | HLA-B39:60 | HLA-B40:103 |
| HLA-B07:62 | HLA-B08:52 | HLA-B15:40 | HLA-B15:147 | HLA-B27:02 | HLA-B35:38 | HLA-B37:01 | HLA-B40:01 | HLA-B40:104 |
| HLA-B07:63 | HLA-B08:53 | HLA-B15:42 | HLA-B15:148 | HLA-B27:03 | HLA-B35:39 | HLA-B37:02 | HLA-B40:02 | HLA-B40:105 |
| HLA-B07:64 | HLA-B08:54 | HLA-B15:43 | HLA-B15:150 | HLA-B27:04 | HLA-B35:41 | HLA-B37:04 | HLA-B40:03 | HLA-B40:106 |
| HLA-B07:65 | HLA-B08:55 | HLA-B15:44 | HLA-B15:151 | HLA-B27:05 | HLA-B35:42 | HLA-B37:05 | HLA-B40:04 | HLA-B40:107 |
| HLA- | HLA- | HLA- | HLA- | HLA- | HLA- | HLA- | HLA- | B40:108 |

TABLE 5-continued

List of HLA-B subtypes against which
binding affinity of peptides are calculated

| | | | | | | | |
|---|---|---|---|---|---|---|---|
| HLA-B07:66 | HLA-B08:56 | HLA-B15:45 | HLA-B15:152 | HLA-B27:06 | HLA-B35:43 | HLA-B37:06 | HLA-B40:05 |
| HLA-B07:68 | HLA-B08:57 | HLA-B15:46 | HLA-B15:153 | HLA-B27:07 | HLA-B35:44 | HLA-B37:07 | HLA-B40:06 |
| HLA-B07:69 | HLA-B08:58 | HLA-B15:47 | HLA-B15:154 | HLA-B27:08 | HLA-B35:45 | HLA-B37:08 | HLA-B40:07 |
| HLA-B07:70 | HLA-B08:59 | HLA-B15:48 | HLA-B15:155 | HLA-B27:09 | HLA-B35:46 | HLA-B37:09 | HLA-B40:08 |
| HLA-B07:71 | HLA-B08:60 | HLA-B15:49 | HLA-B15:156 | HLA-B27:10 | HLA-B35:47 | HLA-B37:10 | HLA-B40:09 |
| HLA-B07:72 | HLA-B08:61 | HLA-B15:50 | HLA-B15:157 | HLA-B27:11 | HLA-B35:48 | HLA-B37:11 | HLA-B40:10 |
| HLA-B07:73 | HLA-B08:62 | HLA-B15:51 | HLA-B15:158 | HLA-B27:12 | HLA-B35:49 | HLA-B37:12 | HLA-B40:11 |
| HLA-B07:74 | HLA-B13:01 | HLA-B15:52 | HLA-B15:159 | HLA-B27:13 | HLA-B35:50 | HLA-B37:14 | HLA-B40:12 |
| HLA-B07:75 | HLA-B13:02 | HLA-B15:53 | HLA-B15:160 | HLA-B27:14 | HLA-B35:51 | HLA-B37:15 | HLA-B40:13 |
| HLA-B07:76 | HLA-B13:03 | HLA-B15:54 | HLA-B15:161 | HLA-B27:15 | HLA-B35:52 | HLA-B37:16 | HLA-B40:14 |
| HLA-B07:77 | HLA-B13:04 | HLA-B15:55 | HLA-B15:162 | HLA-B27:16 | HLA-B35:54 | HLA-B37:17 | HLA-B40:15 |
| HLA-B07:78 | HLA-B13:06 | HLA-B15:56 | HLA-B15:163 | HLA-B27:17 | HLA-B35:55 | HLA-B37:18 | HLA-B40:16 |
| HLA-B07:79 | HLA-B13:09 | HLA-B15:57 | HLA-B15:164 | HLA-B27:18 | HLA-B35:56 | HLA-B37:19 | HLA-B40:18 |
| HLA-B07:80 | HLA-B13:10 | HLA-B15:58 | HLA-B15:165 | HLA-B27:19 | HLA-B35:57 | HLA-B37:20 | HLA-B40:19 |
| HLA-B07:81 | HLA-B13:11 | HLA-B15:60 | HLA-B15:166 | HLA-B27:20 | HLA-B35:58 | HLA-B37:21 | HLA-B40:20 |
| HLA-B07:82 | HLA-B13:12 | HLA-B15:61 | HLA-B15:167 | HLA-B27:21 | HLA-B35:59 | HLA-B37:22 | HLA-B40:21 |
| HLA-B07:83 | HLA-B13:13 | HLA-B15:62 | HLA-B15:168 | HLA-B27:23 | HLA-B35:60 | HLA-B37:23 | HLA-B40:23 |
| HLA-B07:84 | HLA-B13:14 | HLA-B15:63 | HLA-B15:169 | HLA-B27:24 | HLA-B35:61 | HLA-B38:01 | HLA-B40:24 |
| HLA-B07:85 | HLA-B13:15 | HLA-B15:64 | HLA-B15:170 | HLA-B27:25 | HLA-B35:62 | HLA-B38:02 | HLA-B40:25 |
| HLA-B07:86 | HLA-B13:16 | HLA-B15:65 | HLA-B15:171 | HLA-B27:26 | HLA-B35:63 | HLA-B38:03 | HLA-B40:26 |
| HLA-B07:87 | HLA-B13:17 | HLA-B15:66 | HLA-B15:172 | HLA-B27:27 | HLA-B35:64 | HLA-B38:04 | HLA-B40:27 |
| HLA-B07:88 | HLA-B13:18 | HLA-B15:67 | HLA-B15:173 | HLA-B27:28 | HLA-B35:66 | HLA-B38:05 | HLA-B40:28 |
| HLA-B07:89 | HLA-B13:19 | HLA-B15:68 | HLA-B15:174 | HLA-B27:29 | HLA-B35:67 | HLA-B38:06 | HLA-B40:29 |
| HLA-B07:90 | HLA-B13:20 | HLA-B15:69 | HLA-B15:175 | HLA-B27:30 | HLA-B35:68 | HLA-B38:07 | HLA-B40:30 |
| HLA-B07:91 | HLA-B13:21 | HLA-B15:70 | HLA-B15:176 | HLA-B27:31 | HLA-B35:69 | HLA-B38:08 | HLA-B40:31 |
| HLA-B07:92 | HLA-B13:22 | HLA-B15:71 | HLA-B15:177 | HLA-B27:32 | HLA-B35:70 | HLA-B38:09 | HLA-B40:32 |
| HLA-B07:93 | HLA-B13:23 | HLA-B15:72 | HLA-B15:178 | HLA-B27:33 | HLA-B35:71 | HLA-B38:10 | HLA-B40:33 |
| HLA-B07:94 | HLA-B13:25 | HLA-B15:73 | HLA-B15:179 | HLA-B27:34 | HLA-B35:72 | HLA-B38:11 | HLA-B40:34 |
| HLA-B07:95 | HLA-B13:26 | HLA-B15:74 | HLA-B15:180 | HLA-B27:35 | HLA-B35:74 | HLA-B38:12 | HLA-B40:35 |
| HLA-B07:96 | HLA-B13:27 | HLA-B15:75 | HLA-B15:183 | HLA-B27:36 | HLA-B35:75 | HLA-B38:13 | HLA-B40:36 |
| HLA-B07:97 | HLA-B13:28 | HLA-B15:76 | HLA-B15:184 | HLA-B27:37 | HLA-B35:76 | HLA-B38:14 | HLA-B40:37 |
| HLA-B07:98 | HLA-B13:29 | HLA-B15:77 | HLA-B15:185 | HLA-B27:38 | HLA-B35:77 | HLA-B38:15 | HLA-B40:38 |
| HLA-B07:99 | HLA-B13:30 | HLA-B15:78 | HLA-B15:186 | HLA-B27:39 | HLA-B35:78 | HLA-B38:16 | HLA-B40:39 |
| HLA-B07:100 | HLA-B13:31 | HLA-B15:80 | HLA-B15:187 | HLA-B27:40 | HLA-B35:79 | HLA-B38:17 | HLA-B40:40 |
| HLA-B07:101 | HLA-B13:32 | HLA-B15:81 | HLA-B15:188 | HLA-B27:41 | HLA-B35:80 | HLA-B38:18 | HLA-B40:42 |
| HLA-B07:102 | HLA-B13:33 | HLA-B15:82 | HLA-B15:189 | HLA-B27:42 | HLA-B35:81 | HLA-B38:19 | HLA-B40:43 |
| | HLA-B13:34 | HLA-B15:83 | HLA-B15:191 | HLA-B27:43 | HLA-B35:82 | HLA-B38:20 | HLA-B40:44 |
| | | | | | | | HLA-B40:109 |
| | | | | | | | HLA-B40:110 |
| | | | | | | | HLA-B40:111 |
| | | | | | | | HLA-B40:112 |
| | | | | | | | HLA-B40:113 |
| | | | | | | | HLA-B40:114 |
| | | | | | | | HLA-B40:115 |
| | | | | | | | HLA-B40:116 |
| | | | | | | | HLA-B40:118 |
| | | | | | | | HLA-B40:119 |
| | | | | | | | HLA-B40:120 |
| | | | | | | | HLA-B40:121 |
| | | | | | | | HLA-B40:122 |
| | | | | | | | HLA-B40:123 |
| | | | | | | | HLA-B40:124 |
| | | | | | | | HLA-B40:125 |
| | | | | | | | HLA-B40:126 |
| | | | | | | | HLA-B40:127 |
| | | | | | | | HLA-B40:128 |
| | | | | | | | HLA-B40:129 |
| | | | | | | | HLA-B40:130 |
| | | | | | | | HLA-B40:131 |
| | | | | | | | HLA-B40:132 |

TABLE 6

List of HLA-C subtypes against which binding affinity of peptides are calculated

| | | | | | | | |
|---|---|---|---|---|---|---|---|
| HLA-C01:02 | HLA-C03:06 | HLA-C03:88 | HLA-C05:11 | HLA-C07:03 | HLA-C07:88 | HLA-C08:22 | HLA-C15:10 |
| HLA-C01:03 | HLA-C03:07 | HLA-C03:89 | HLA-C05:12 | HLA-C07:04 | HLA-C07:89 | HLA-C08:23 | HLA-C15:11 |
| HLA-C01:04 | HLA-C03:08 | HLA-C03:90 | HLA-C05:13 | HLA-C07:05 | HLA-C07:90 | HLA-C08:24 | HLA-C15:12 |
| HLA-C01:05 | HLA-C03:09 | HLA-C03:91 | HLA-C05:14 | HLA-C07:06 | HLA-C07:91 | HLA-C08:25 | HLA-C15:13 |
| HLA-C01:06 | HLA-C03:10 | HLA-C03:92 | HLA-C05:15 | HLA-C07:07 | HLA-C07:92 | HLA-C08:27 | HLA-C15:15 |
| HLA-C01:07 | HLA-C03:11 | HLA-C03:93 | HLA-C05:16 | HLA-C07:08 | HLA-C07:93 | HLA-C08:28 | HLA-C15:16 |
| HLA-C01:08 | HLA-C03:12 | HLA-C03:94 | HLA-C05:17 | HLA-C07:09 | HLA-C07:94 | HLA-C08:29 | HLA-C15:17 |
| HLA-C01:09 | HLA-C03:13 | HLA-C04:01 | HLA-C05:18 | HLA-C07:10 | HLA-C07:95 | HLA-C08:30 | HLA-C15:18 |
| HLA-C01:10 | HLA-C03:14 | HLA-C04:03 | HLA-C05:19 | HLA-C07:11 | HLA-C07:96 | HLA-C08:31 | HLA-C15:19 |
| HLA-C01:11 | HLA-C03:15 | HLA-C04:04 | HLA-C05:20 | HLA-C07:12 | HLA-C07:97 | HLA-C08:32 | HLA-C15:20 |
| HLA-C01:12 | HLA-C03:16 | HLA-C04:05 | HLA-C05:21 | HLA-C07:13 | HLA-C07:99 | HLA-C08:33 | HLA-C15:21 |
| HLA-C01:13 | HLA-C03:17 | HLA-C04:06 | HLA-C05:22 | HLA-C07:14 | HLA-C07:100 | HLA-C08:34 | HLA-C15:22 |
| HLA-C01:14 | HLA-C03:18 | HLA-C04:07 | HLA-C05:23 | HLA-C07:15 | HLA-C07:101 | HLA-C08:35 | HLA-C15:23 |
| HLA-C01:15 | HLA-C03:19 | HLA-C04:08 | HLA-C05:24 | HLA-C07:16 | HLA-C07:102 | HLA-C12:02 | HLA-C15:24 |
| HLA-C01:16 | HLA-C03:21 | HLA-C04:10 | HLA-C05:25 | HLA-C07:17 | HLA-C07:103 | HLA-C12:03 | HLA-C15:25 |
| HLA-C01:17 | HLA-C03:23 | HLA-C04:11 | HLA-C05:26 | HLA-C07:18 | HLA-C07:105 | HLA-C12:04 | HLA-C15:26 |
| HLA-C01:18 | HLA-C03:24 | HLA-C04:12 | HLA-C05:27 | HLA-C07:19 | HLA-C07:106 | HLA-C12:05 | HLA-C15:27 |
| HLA-C01:19 | HLA-C03:25 | HLA-C04:13 | HLA-C05:28 | HLA-C07:20 | HLA-C07:107 | HLA-C12:06 | HLA-C15:28 |
| HLA-C01:20 | HLA-C03:26 | HLA-C04:14 | HLA-C05:29 | HLA-C07:21 | HLA-C07:108 | HLA-C12:07 | HLA-C15:29 |
| HLA-C01:21 | HLA-C03:27 | HLA-C04:15 | HLA-C05:30 | HLA-C07:22 | HLA-C07:109 | HLA-C12:08 | HLA-C15:30 |
| HLA-C01:22 | HLA-C03:28 | HLA-C04:16 | HLA-C05:31 | HLA-C07:23 | HLA-C07:110 | HLA-C12:09 | HLA-C15:31 |
| HLA-C01:23 | HLA-C03:29 | HLA-C04:17 | HLA-C05:32 | HLA-C07:24 | HLA-C07:111 | HLA-C12:10 | HLA-C15:33 |
| HLA-C01:24 | HLA-C03:30 | HLA-C04:18 | HLA-C05:33 | HLA-C07:25 | HLA-C07:112 | HLA-C12:11 | HLA-C15:34 |
| HLA-C01:25 | HLA-C03:31 | HLA-C04:19 | HLA-C05:34 | HLA-C07:26 | HLA-C07:113 | HLA-C12:12 | HLA-C15:35 |
| HLA-C01:26 | HLA-C03:32 | HLA-C04:20 | HLA-C05:35 | HLA-C07:27 | HLA-C07:114 | HLA-C12:13 | HLA-C16:01 |
| HLA-C01:27 | HLA-C03:33 | HLA-C04:23 | HLA-C05:36 | HLA-C07:28 | HLA-C07:115 | HLA-C12:14 | HLA-C16:02 |
| HLA-C01:28 | HLA-C03:34 | HLA-C04:24 | HLA-C05:37 | HLA-C07:29 | HLA-C07:116 | HLA-C12:15 | HLA-C16:04 |
| HLA-C01:29 | HLA-C03:35 | HLA-C04:25 | HLA-C05:38 | HLA-C07:30 | HLA-C07:117 | HLA-C12:16 | HLA-C16:06 |
| HLA-C01:30 | HLA-C03:36 | HLA-C04:26 | HLA-C05:39 | HLA-C07:31 | HLA-C07:118 | HLA-C12:17 | HLA-C16:07 |
| HLA-C01:31 | HLA-C03:37 | HLA-C04:27 | HLA-C05:40 | HLA-C07:35 | HLA-C07:119 | HLA-C12:18 | HLA-C16:08 |
| HLA-C01:32 | HLA-C03:38 | HLA-C04:28 | HLA-C05:41 | HLA-C07:36 | HLA-C07:120 | HLA-C12:19 | HLA-C16:09 |
| HLA-C01:33 | HLA-C03:39 | HLA-C04:29 | HLA-C05:42 | HLA-C07:37 | HLA-C07:122 | HLA-C12:20 | HLA-C16:10 |
| HLA-C01:34 | HLA-C03:40 | HLA-C04:30 | HLA-C05:43 | HLA-C07:38 | HLA-C07:123 | HLA-C12:21 | HLA-C16:11 |
| HLA-C01:35 | HLA-C03:41 | HLA-C04:31 | HLA-C05:44 | HLA-C07:39 | HLA-C07:124 | HLA-C12:22 | HLA-C16:12 |
| HLA-C01:36 | HLA-C03:42 | HLA-C04:32 | HLA-C05:45 | HLA-C07:40 | HLA-C07:125 | HLA-C12:23 | HLA-C16:13 |
| HLA-C01:38 | HLA-C03:43 | HLA-C04:33 | HLA-C06:02 | HLA-C07:41 | HLA-C07:126 | HLA-C12:24 | HLA-C16:14 |
| HLA-C01:39 | HLA-C03:44 | HLA-C04:34 | HLA-C06:03 | HLA-C07:42 | HLA-C07:127 | HLA-C12:25 | HLA-C16:15 |
| HLA-C01:40 | HLA-C03:45 | HLA-C04:35 | HLA-C06:04 | HLA-C07:43 | HLA-C07:128 | HLA-C12:26 | HLA-C16:17 |
| HLA- | HLA- | HLA- | HLA- | HLA- | HLA- | HLA- | HLA- |

TABLE 6-continued

List of HLA-C subtypes against which binding
affinity of peptides are calculated

| | | | | | | | |
|---|---|---|---|---|---|---|---|
| HLA-C02:02 | HLA-C03:46 | HLA-C04:36 | HLA-C06:05 | HLA-C07:44 | HLA-C07:129 | HLA-C12:27 | HLA-C16:18 |
| HLA-C02:03 | HLA-C03:47 | HLA-C04:37 | HLA-C06:06 | HLA-C07:45 | HLA-C07:130 | HLA-C12:28 | HLA-C16:19 |
| HLA-C02:04 | HLA-C03:48 | HLA-C04:38 | HLA-C06:07 | HLA-C07:46 | HLA-C07:131 | HLA-C12:29 | HLA-C16:20 |
| HLA-C02:05 | HLA-C03:49 | HLA-C04:39 | HLA-C06:08 | HLA-C07:47 | HLA-C07:132 | HLA-C12:30 | HLA-C16:21 |
| HLA-C02:06 | HLA-C03:50 | HLA-C04:40 | HLA-C06:09 | HLA-C07:48 | HLA-C07:133 | HLA-C12:31 | HLA-C16:22 |
| HLA-C02:07 | HLA-C03:51 | HLA-C04:41 | HLA-C06:10 | HLA-C07:49 | HLA-C07:134 | HLA-C12:32 | HLA-C16:23 |
| HLA-C02:08 | HLA-C03:52 | HLA-C04:42 | HLA-C06:11 | HLA-C07:50 | HLA-C07:135 | HLA-C12:33 | HLA-C16:24 |
| HLA-C02:09 | HLA-C03:53 | HLA-C04:43 | HLA-C06:12 | HLA-C07:51 | HLA-C07:136 | HLA-C12:34 | HLA-C16:25 |
| HLA-C02:10 | HLA-C03:54 | HLA-C04:44 | HLA-C06:13 | HLA-C07:52 | HLA-C07:137 | HLA-C12:35 | HLA-C16:26 |
| HLA-C02:11 | HLA-C03:55 | HLA-C04:45 | HLA-C06:14 | HLA-C07:53 | HLA-C07:138 | HLA-C12:36 | HLA-C17:01 |
| HLA-C02:12 | HLA-C03:56 | HLA-C04:46 | HLA-C06:15 | HLA-C07:54 | HLA-C07:139 | HLA-C12:37 | HLA-C17:02 |
| HLA-C02:13 | HLA-C03:57 | HLA-C04:47 | HLA-C06:17 | HLA-C07:56 | HLA-C07:140 | HLA-C12:38 | HLA-C17:03 |
| HLA-C02:14 | HLA-C03:58 | HLA-C04:48 | HLA-C06:18 | HLA-C07:57 | HLA-C07:141 | HLA-C12:40 | HLA-C17:04 |
| HLA-C02:15 | HLA-C03:59 | HLA-C04:49 | HLA-C06:19 | HLA-C07:58 | HLA-C07:142 | HLA-C12:41 | HLA-C17:05 |
| HLA-C02:16 | HLA-C03:60 | HLA-C04:50 | HLA-C06:20 | HLA-C07:59 | HLA-C07:143 | HLA-C12:43 | HLA-C17:06 |
| HLA-C02:17 | HLA-C03:61 | HLA-C04:51 | HLA-C06:21 | HLA-C07:60 | HLA-C07:144 | HLA-C12:44 | HLA-C17:07 |
| HLA-C02:18 | HLA-C03:62 | HLA-C04:52 | HLA-C06:22 | HLA-C07:62 | HLA-C07:145 | HLA-C14:02 | HLA-C18:01 |
| HLA-C02:19 | HLA-C03:63 | HLA-C04:53 | HLA-C06:23 | HLA-C07:63 | HLA-C07:146 | HLA-C14:03 | HLA-C18:02 |
| HLA-C02:20 | HLA-C03:64 | HLA-C04:54 | HLA-C06:24 | HLA-C07:64 | HLA-C07:147 | HLA-C14:04 | HLA-C18:03 |
| HLA-C02:21 | HLA-C03:65 | HLA-C04:55 | HLA-C06:25 | HLA-C07:65 | HLA-C07:148 | HLA-C14:05 | |
| HLA-C02:22 | HLA-C03:66 | HLA-C04:56 | HLA-C06:26 | HLA-C07:66 | HLA-C07:149 | HLA-C14:06 | |
| HLA-C02:23 | HLA-C03:67 | HLA-C04:57 | HLA-C06:27 | HLA-C07:67 | HLA-C08:01 | HLA-C14:08 | |
| HLA-C02:24 | HLA-C03:68 | HLA-C04:58 | HLA-C06:28 | HLA-C07:68 | HLA-C08:02 | HLA-C14:09 | |
| HLA-C02:26 | HLA-C03:69 | HLA-C04:60 | HLA-C06:29 | HLA-C07:69 | HLA-C08:03 | HLA-C14:10 | |
| HLA-C02:27 | HLA-C03:70 | HLA-C04:61 | HLA-C06:30 | HLA-C07:70 | HLA-C08:04 | HLA-C14:11 | |
| HLA-C02:28 | HLA-C03:71 | HLA-C04:62 | HLA-C06:31 | HLA-C07:71 | HLA-C08:05 | HLA-C14:12 | |
| HLA-C02:29 | HLA-C03:72 | HLA-C04:63 | HLA-C06:32 | HLA-C07:72 | HLA-C08:06 | HLA C14:13 | |
| HLA-C02:30 | HLA-C03:73 | HLA-C04:64 | HLA-C06:33 | HLA-C07:73 | HLA-C08:07 | HLA-C14:14 | |
| HLA-C02:31 | HLA-C03:74 | HLA-C04:65 | HLA-C06:34 | HLA-C07:74 | HLA-C08:08 | HLA-C14:15 | |
| HLA-C02:32 | HLA-C03:75 | HLA-C04:66 | HLA-C06:35 | HLA-C07:75 | HLA-C08:09 | HLA-C14:16 | |
| HLA-C02:33 | HLA-C03:76 | HLA-C04:67 | HLA-C06:36 | HLA-C07:76 | HLA-C08:10 | HLA-C14:17 | |
| HLA-C02:34 | HLA-C03:77 | HLA-C04:68 | HLA-C06:37 | HLA-C07:77 | HLA-C08:11 | HLA-C14:18 | |
| HLA-C02:35 | HLA-C03:78 | HLA-C04:69 | HLA-C06:38 | HLA-C07:78 | HLA-C08:12 | HLA-C14:19 | |
| HLA-C02:36 | HLA-C03:79 | HLA-C04:70 | HLA-C06:39 | HLA-C07:79 | HLA-C08:13 | HLA-C14:20 | |
| HLA-C02:37 | HLA-C03:80 | HLA-C05:01 | HLA-C06:40 | HLA-C07:80 | HLA-C08:14 | HLA-C15:02 | |
| HLA-C02:39 | HLA-C03:81 | HLA-C05:03 | HLA-C06:41 | HLA-C07:81 | HLA-C08:15 | HLA-C15:03 | |
| HLA-C02:40 | HLA-C03:82 | HLA-C05:04 | HLA-C06:42 | HLA-C07:82 | HLA-C08:16 | HLA-C15:04 | |
| HLA-C03:01 | HLA-C03:83 | HLA-C05:05 | HLA-C06:43 | HLA-C07:83 | HLA-C08:17 | HLA-C15:05 | |
| HLA-C03:02 | HLA-C03:84 | HLA-C05:06 | HLA-C06:44 | HLA-C07:84 | HLA-C08:18 | HLA-C15:06 | |

TABLE 6-continued

List of HLA-C subtypes against which binding affinity of peptides are calculated

| HLA-C03:03 | HLA-C03:85 | HLA-C05:08 | HLA-C06:45 | HLA-C07:85 | HLA-C08:19 | HLA-C15:07 |
|---|---|---|---|---|---|---|
| HLA-C03:04 | HLA-C03:86 | HLA-C05:09 | HLA-C07:01 | HLA-C07:86 | HLA-C08:20 | HLA-C15:08 |
| HLA-C03:05 | HLA-C03:87 | HLA-C05:10 | HLA-C07:02 | HLA-C07:87 | HLA-C08:21 | HLA-C15:09 |

TABLE 7

List of HLA-Class II subtypes against which binding affinity of peptides are calculated

| HLA DR | HLA DQ | HLA DP |
|---|---|---|
| HLA-DRB1*01:01 | HLA-DQA1*05:01/DQB1*02:01 | HLA-DPA1*02:01/DPB1*01:01 |
| HLA-DRB1*03:01 | HLA-DQA1*05:01/DQB1*03:01 | HLA-DPA1*01:03/DPB1*02:01 |
| HLA-DRB1*04:01 | HLA-DQA1*03:01/DQB1*03:02 | HLA-DPA1*01/DPB1*04:01 |
| HLA-DRB1*04:05 | HLA-DQA1*04:01/DQB1*04:02 | HLA-DPA1*03:01/DPB1*04:02 |
| HLA-DRB1*07:01 | HLA-DQA1*01:01/DQB1*05:01 | HLA-DPA1*02:01/DPB1*05:01 |
| HLA-DRB1*08:02 | HLA-DQA1*01:02/DQB1*06:02 | HLA-DPA1*02:01/DPB1*14:01 |
| HLA-DRB1*09:01 | | |
| HLA-DRB1*11:01 | | |
| HLA-DRB1*12:01 | | |
| HLA-DRB1*13:02 | | |
| HLA-DRB1*15:01 | | |
| HLA-DRB3*01:01 | | |
| HLA-DRB3*02:02 | | |
| HLA-DRB4*01:01 | | |
| HLA-DRB5*01:01 | | |

TABLE 8

Peptides classified as Non-immunogenic in the IEDB database used for developing the TCR-binding algorithm

| | | | | |
|---|---|---|---|---|
| WLLIDTSNA (SEQ ID NO.: 90) | SLAGFVRML (SEQ ID NO.: 114) | KLDKEMEAV (SEQ ID NO.: 138) | DVVNGLANL (SEQ ID NO.: 162) | VLLLDVTPL (SEQ ID NO.: 186) |
| RVSRPTTVV (SEQ ID NO.: 91) | GLFLTTEAV (SEQ ID NO.: 115) | VLADANETL (SEQ ID NO.: 139) | ALAPAPVEV (SEQ ID NO.: 163) | AIYHPQQFV (SEQ ID NO.: 187) |
| YLDLALMSV (SEQ ID NO.: 92) | RLQSLQTYV (SEQ ID NO.: 116) | MLGNAPSVV (SEQ ID NO.: 140) | YLGKLFVTL (SEQ ID NO.: 164) | AMKADIQHV (SEQ ID NO.: 188) |
| FIFLLFLTL (SEQ ID NO.: 93) | LLPLGYPFV (SEQ ID NO.: 117) | LLWQDPVPA (SEQ ID NO.: 141) | GADEDDIKA (SEQ ID NO.: 165) | ALLSDWLPA (SEQ ID NO.: 189) |
| DETGVEVKD (SEQ ID NO.: 94) | ALLRQLAEL (SEQ ID NO.: 118) | RLLEAFQFV (SEQ ID NO.: 142) | KLLTKPWDV (SEQ ID NO.: 166) | RMFAANLGV (SEQ ID NO.: 190) |
| LMLPGMNGI (SEQ ID NO.: 95) | FVVALIPLV (SEQ ID NO.: 119) | LLPPELSET (SEQ ID NO.: 143) | WMIIHNMDLV (SEQ ID NO.: 167) | MLQDMAILT (SEQ ID NO.: 191) |
| EMKEGRYEV (SEQ ID NO.: 96) | SLQNSEFLL (SEQ ID NO.: 120) | GLVDINKHI (SEQ ID NO.: 144) | GLYLSQIAV (SEQ ID NO.: 168) | ALLWAAGVL (SEQ ID NO.: 192) |
| VLLEKATIL (SEQ ID NO.: 97) | AYGSFVRTV (SEQ ID NO.: 121) | VLLEQMGSL (SEQ ID NO.: 145) | ILFTFLHLA (SEQ ID NO.: 169) | LLFRFMRPL (SEQ ID NO.: 193) |
| SLLERGQQL (SEQ ID NO.: 98) | GLMTAVYLV (SEQ ID NO.: 122) | MLADKTKSI (SEQ ID NO.: 146) | TEVGQDQYV (SEQ ID NO.: 170) | RLGAVILFV (SEQ ID NO.: 194) |

TABLE 8-continued

Peptides classified as Non-immunogenic in the IEDB database used for developing the TCR-binding algorithm

| | | | | |
|---|---|---|---|---|
| YLSEGDMAA (SEQ ID NO.: 99) | LMHAPAFET (SEQ ID NO.: 123) | LVLEQLGQL (SEQ ID NO.: 147) | TRHPATATV (SEQ ID NO.: 171) | DLSRDLDSV (SEQ ID NO.: 195) |
| RVYEALYYV (SEQ ID NO.: 100) | GLYYLTTEV (SEQ ID NO.: 124) | RMPAVTDLV (SEQ ID NO.: 148) | LLFLGVVFL (SEQ ID NO.: 172) | GLYGAQYDV (SEQ ID NO.: 196) |
| KLGLLQVTG (SEQ ID NO.: 101) | LLYNEQFAV (SEQ ID NO.: 125) | TRVTIWKSK (SEQ ID NO.: 149) | ILSSLGLPV (SEQ ID NO.: 173) | FLAVGGVLL (SEQ ID NO.: 197) |
| SMAGNWAKV (SEQ ID NO.: 102) | VVFEDVKGT (SEQ ID NO.: 126) | YLSQIAVLL (SEQ ID NO.: 150) | FANYNFTLL (SEQ ID NO.: 174) | MLASTLTDA (SEQ ID NO.: 198) |
| VVWVKITQV (SEQ ID NO.: 103) | ALSTGLIHL (SEQ ID NO.: 127) | YLLALRYLA (SEQ ID NO.: 151) | ILLSIARVV (SEQ ID NO.: 175) | YLVTSINKL (SEQ ID NO.: 199) |
| GLYRQWALA (SEQ ID NO.: 104) | FIPENQRTV (SEQ ID NO.: 128) | RLMIGTAAA (SEQ ID NO.: 152) | IVYEAADAI (SEQ ID NO.: 176) | SLPKHNVTI (SEQ ID NO.: 200) |
| SMGIFLKSL (SEQ ID NO.: 105) | DLPSGFNTL (SEQ ID NO.: 129) | FLLPDAQSI (SEQ ID NO.: 153) | KFRVQGEAV (SEQ ID NO.: 177) | RLARAIIEL (SEQ ID NO.: 201) |
| SLFPEFSEL (SEQ ID NO.: 106) | GLFGKGSLV (SEQ ID NO.: 130) | YTYKWETFL (SEQ ID NO.: 154) | RLLDDTPEV (SEQ ID NO.: 178) | MALLRLPLV (SEQ ID NO.: 202) |
| GESVPGIEE (SEQ ID NO.: 107) | NSNDIVNAI (SEQ ID NO.: 131) | AETGSGTAS (SEQ ID NO.: 155) | KIFCISIFL (SEQ ID NO.: 179) | YKSPASDAY (SEQ ID NO.: 203) |
| YLYVHSPAL (SEQ ID NO.: 108) | TVLRFVPPL (SEQ ID NO.: 132) | KLCTFSFLI (SEQ ID NO.: 156) | AMLQDMAIL (SEQ ID NO.: 180) | KLSSFFQSV (SEQ ID NO.: 204) |
| FMKAVCVEV (SEQ ID NO.: 109) | SLLEIGEGV (SEQ ID NO.: 133) | FLIHSADWL (SEQ ID NO.: 157) | ALVLLMLPV (SEQ ID NO.: 181) | AIMDKKIIL (SEQ ID NO.: 205) |
| DSTQTTTQK (SEQ ID NO.: 110) | VIADYNYKL (SEQ ID NO.: 134) | ALWGPDPAA (SEQ ID NO.: 158) | MIAAYTAAL (SEQ ID NO.: 182) | |
| YSLEYFQFV (SEQ ID NO.: 111) | AIMDKTVIL (SEQ ID NO.: 135) | NILFVITKL (SEQ ID NO.: 159) | AALGLWLSV (SEQ ID NO.: 183) | |
| RAKAVRALK (SEQ ID NO.: 112) | KVLTLFAEV (SEQ ID NO.: 136) | LLACAVIHA (SEQ ID NO.: 160) | VLCPYMPKV (SEQ ID NO.: 184) | |
| TEQELPQSQ (SEQ ID NO.: 113) | SRAKAVRAL (SEQ ID NO.: 137) | TLAARIKFL (SEQ ID NO.: 161) | ALIIIRSLL (SEQ ID NO.: 185) | |

TABLE 9

Peptides classified as Immunogenic in the IEDB database used for developing the TCR-binding algorithm

| | | | | |
|---|---|---|---|---|
| SLKDVLVSV (SEQ ID NO.: 206) | LLMWEAVTV (SEQ ID NO.: 268) | ILLWEIPDV (SEQ ID NO.: 330) | FLYGALLLA (SEQ ID NO.: 392) | MINPLVITT (SEQ ID NO.: 454) |
| VAALFFFDI (SEQ ID NO.: 207) | GMLGFVFTL (SEQ ID NO.: 269) | HLMIDRPYV (SEQ ID NO.: 331) | LLDVAPLSL (SEQ ID NO.: 393) | FILPVLGAV (SEQ ID NO.: 455) |

TABLE 9-continued

Peptides classified as Immunogenic in the IEDB database used for developing the TCR-binding algorithm

| | | | | |
|---|---|---|---|---|
| SLWGGDVVL (SEQ ID NO.: 208) | LGYGFVNYI (SEQ ID NO.: 270) | ALISAFSGS (SEQ ID NO.: 332) | MGLPGVATV (SEQ ID NO.: 394) | FAFRDLCIV (SEQ ID NO.: 456) |
| AMDTISVFL (SEQ ID NO.: 209) | LIVDAVLQL (SEQ ID NO.: 271) | RQYDPVAAL (SEQ ID NO.: 333) | FANCNFTLV (SEQ ID NO.: 395) | RMFPNAPYL (SEQ ID NO.: 457) |
| VLLLWITAA (SEQ ID NO.: 210) | FLLDILGAT (SEQ ID NO.: 272) | LLIGGFAGL (SEQ ID NO.: 334) | NLNESLIDL (SEQ ID NO.: 396) | KVLIRCYLC (SEQ ID NO.: 458) |
| MLWYTVYNI (SEQ ID NO.: 211) | RLLQTGIHV (SEQ ID NO.: 273) | FANYKFTLV (SEQ ID NO.: 335) | LLWSYAMGV (SEQ ID NO.: 397) | KLIVTPAAL (SEQ ID NO.: 459) |
| RVPGVAPTL (SEQ ID NO.: 212) | FLGERVTLT (SEQ ID NO.: 274) | VPILLKALY (SEQ ID NO.: 336) | FMVFLQTHI (SEQ ID NO.: 398) | VLQELNVTV (SEQ ID NO.: 460) |
| WLDEVKQAL (SEQ ID NO.: 213) | FVNYDFTIV (SEQ ID NO.: 275) | LLWNGPMAV (SEQ ID NO.: 337) | RVNRLIIWV (SEQ ID NO.: 399) | LLNYILKSV (SEQ ID NO.: 461) |
| ALNTPKDHI (SEQ ID NO.: 214) | KLNDWDFVV (SEQ ID NO.: 276) | KLSDYEGRL (SEQ ID NO.: 338) | SLMSGVEPL (SEQ ID NO.: 400) | MMFGFHHSV (SEQ ID NO.: 462) |
| AWLVAAAEI (SEQ ID NO.: 215) | LFLNTLSFV (SEQ ID NO.: 277) | GMVTTSTTL (SEQ ID NO.: 339) | TLDYKPLSV (SEQ ID NO.: 401) | IVLGLIATA (SEQ ID NO.: 463) |
| AILHTPGCV (SEQ ID NO.: 216) | GGNGMLATI (SEQ ID NO.: 278) | SLVEELKKV (SEQ ID NO.: 340) | SLFNTVATL (SEQ ID NO.: 402) | YLNKIQNSL (SEQ ID NO.: 464) |
| GLLDQVAAL (SEQ ID NO.: 217) | SFHSLHLLF (SEQ ID NO.: 279) | ALSALLTKL (SEQ ID NO.: 342) | VLLRHSKNV (SEQ ID NO.: 403) | QLLSSSKYT (SEQ ID NO.: 465) |
| SQQAQLAAA (SEQ ID NO.: 218) | AIIIAVLLV (SEQ ID NO.: 280) | FVDYNITSLV (SEQ ID NO.: 343) | VLLCVCLLI (SEQ ID NO.: 404) | CLFKDWEEL (SEQ ID NO.: 466) |
| TLKDIVLDL (SEQ ID NO.: 219) | RFIAQLLLL (SEQ ID NO.: 281) | ILLNKHIDA (SEQ ID NO.: 344) | SLLMWITQC (SEQ ID NO.: 405) | AIIDPLIYA (SEQ ID NO.: 467) |
| MLNIPSINV (SEQ ID NO.: 220) | SIYVYALPL (SEQ ID NO.: 282) | ILNNPKASL (SEQ ID NO.: 345) | GLNDYLHSV (SEQ ID NO.: 406) | TLGIVCPIC (SEQ ID NO.: 468) |
| AIMDKVIIL (SEQ ID NO.: 221) | PTLDKVLEV (SEQ ID NO.: 283) | FQQLFLNTL (SEQ ID NO.: 346) | AMASTEGNV (SEQ ID NO.: 407) | KYQEFFWDA (SEQ ID NO.: 469) |
| GILGFVYTL (SEQ ID NO.: 222) | LVLILYLCV (SEQ ID NO.: 284) | ALLGLTLGV (SEQ ID NO.: 347) | GLREDLLSL (SEQ ID NO.: 408) | LALPMPATA (SEQ ID NO.: 470) |
| TLEEFSAKL (SEQ ID NO.: 223) | GMSRIGMEV (SEQ ID NO.: 285) | GLMWLSYFV (SEQ ID NO.: 348) | KLWCRHFCV (SEQ ID NO.: 409) | SLMSWSAIL (SEQ ID NO.: 471) |
| LLDAHIPQL (SEQ ID NO.: 224) | FLSHDFTLV (SEQ ID NO.: 286) | KVDDTFYYV (SEQ ID NO.: 349) | ALAIIIAVL (SEQ ID NO.: 410) | KVLGLWATV (SEQ ID NO.: 472) |
| RTLDKVLEV (SEQ ID NO.: 225) | CINGVCWSV (SEQ ID NO.: 287) | ALFHEVAKL (SEQ ID NO.: 350) | LQLPQGTTL (SEQ ID NO.: 411) | ILPDPLKPT (SEQ ID NO.: 473) |
| YLESFCEDV (SEQ ID NO.: 226) | SITEVECFL (SEQ ID NO.: 288) | SLPRSRTPI (SEQ ID NO.: 351) | FLWEDQTLL (SEQ ID NO.: 412) | FLSFASLFL (SEQ ID NO.: 474) |

TABLE 9-continued

Peptides classified as Immunogenic in the IEDB database used for developing the TCR-binding algorithm

| | | | | |
|---|---|---|---|---|
| RMTENIVEV (SEQ ID NO.: 227) | RLERKWLDV (SEQ ID NO.: 289) | LMLIWYRPV (SEQ ID NO.: 352) | FLLKLTPLL (SEQ ID NO.: 413) | ILIEGVFFA (SEQ ID NO.: 475) |
| GILGVVFTL (SEQ ID NO.: 228) | SIDQLCKTF (SEQ ID NO.: 290) | IVIEAIHTV (SEQ ID NO.: 353) | GIWGFVFTL (SEQ ID NO.: 414) | ALLEDPVGT (SEQ ID NO.: 476) |
| RGTPMVITV (SEQ ID NO.: 229) | QLFNHTMFI (SEQ ID NO.: 291) | SLILVSQYT (SEQ ID NO.: 354) | FANHKFTLV (SEQ ID NO.: 415) | FVNYNFTLV (SEQ ID NO.: 477) |
| HLGNVKYLV (SEQ ID NO.: 230) | MIMQGGFSV (SEQ ID NO.: 292) | GTLGFVFTL (SEQ ID NO.: 355) | QMMRNEFRV (SEQ ID NO.: 416) | WQWEHIPPA (SEQ ID NO.: 478) |
| VVPEDYWGV (SEQ ID NO.: 231) | KCIDFYSRI (SEQ ID NO.: 293) | RLNEVAKNL (SEQ ID NO.: 356) | FLLCFCVLL (SEQ ID NO.: 417) | VMLFILAGL (SEQ ID NO.: 479) |
| VLNDILSRL (SEQ ID NO.: 232) | SLKKNSRSL (SEQ ID NO.: 294) | MINAYLDKL (SEQ ID NO.: 357) | GILTVSVAV (SEQ ID NO.: 418) | MTYAAPLFV (SEQ ID NO.: 480) |
| RLPLVLPAV (SEQ ID NO.: 233) | MLDLQPETT (SEQ ID NO.: 295) | TIDQLCKTF (SEQ ID NO.: 358) | FVDYNFTIV (SEQ ID NO.: 419) | YLKKIKNSL (SEQ ID NO.: 481) |
| VLNETTNWL (SEQ ID NO.: 234) | MTIIFLILM (SEQ ID NO.: 296) | LVLPILIT1 (SEQ ID NO.: 359) | ALYDVVSKL (SEQ ID NO.: 420) | AMAGASTSA (SEQ ID NO.: 482) |
| ALSEDLLSI (SEQ ID NO.: 235) | NDFCCVATV (SEQ ID NO.: 297) | AIVDKNITL (SEQ ID NO.: 360) | LFAAFPSFA (SEQ ID NO.: 421) | NMLSTVLGV (SEQ ID NO.: 483) |
| GILGFIFTL (SEQ ID NO.: 236) | YLEPGPVTA (SEQ ID NO.: 298) | RLIQNSITI (SEQ ID NO.: 361) | LLGRNSFEV (SEQ ID NO.: 422) | ILAKFLHWL (SEQ ID NO.: 484) |
| IMVLSFLFL (SEQ ID NO.: 237) | ILDKKVEKV (SEQ ID NO.: 299) | ILRSFIPLL (SEQ ID NO.: 362) | MLLDKNIPI (SEQ ID NO.: 423) | KLGPGEEQV (SEQ ID NO.: 485) |
| TLAPQVEPL (SEQ ID NO.: 238) | LALLLLDRL (SEQ ID NO.: 300) | FANFINFTLV (SEQ ID NO.: 363) | MLWGYLQYV (SEQ ID NO.: 424) | SVYDFFVWL (SEQ ID NO.: 486) |
| FTWEGLYNV (SEQ ID NO.: 239) | FIDKFTPPV (SEQ ID NO.: 301) | QLSTRGVQI (SEQ ID NO.: 364) | NLLTTPKFT (SEQ ID NO.: 425) | VLTSESMHV (SEQ ID NO.: 487) |
| AIMDKTIIL (SEQ ID NO.: 240) | GILEFVFTL (SEQ ID NO.: 302) | LLSILCIWV (SEQ ID NO.: 365) | TLYAVATTI (SEQ ID NO.: 426) | SLSRFSWGA (SEQ ID NO.: 488) |
| GVLGFVFTL (SEQ ID NO.: 241) | YLVSIFLHL (SEQ ID NO.: 303) | PTLDKVLEL (SEQ ID NO.: 366) | FLKQQYMNL (SEQ ID NO.: 427) | RMLGDVMAV (SEQ ID NO.: 489) |
| RLQGISPKI (SEQ ID NO.: 242) | FVVPILLKA (SEQ ID NO.: 304) | GVRVLEDGV (SEQ ID NO.: 367) | KDLVLLATI (SEQ ID NO.: 428) | YILEETSVM (SEQ ID NO.: 490) |
| ALLKDTVYT (SEQ ID NO.: 243) | CLPACVYGL (SEQ ID NO.: 305) | MVMELIRMI (SEQ ID NO.: 368) | LLVSEIDWL (SEQ ID NO.: 429) | ILDAHSLYL (SEQ ID NO.: 491) |
| LLLIWFRPV (SEQ ID NO.: 244) | VLSEWLPVT (SEQ ID NO.: 306) | SAPLPSNRV (SEQ ID NO.: 369) | KLNPMLAKA (SEQ ID NO.: 430) | GIFEDRAPV (SEQ ID NO.: 492) |
| VAANIVLTV (SEQ ID NO.: 245) | TLLDHIRTA (SEQ ID NO.: 307) | LQLCCLATA (SEQ ID NO.: 370) | VIFDFLHCI (SEQ ID NO.: 431) | TVCGGIMFL (SEQ ID NO.: 493) |

TABLE 9-continued

Peptides classified as Immunogenic in the IEDB database used for developing the TCR-binding algorithm

| | | | | |
|---|---|---|---|---|
| AMLHWSLIL (SEQ ID NO.: 246) | KMLKEMGEV (SEQ ID NO.: 308) | ELTEVFEFA (SEQ ID NO.: 371) | FANNEFTLV (SEQ ID NO.: 432) | GLCPHCINV (SEQ ID NO.: 494) |
| ALAVLSVTL (SEQ ID NO.: 247) | AVADHVAAV (SEQ ID NO.: 309) | CLTEYILWV (SEQ ID NO.: 372) | VLCLRPVGA (SEQ ID NO.: 433) | AFLGERVTL (SEQ ID NO.: 495) |
| SGDGLVATG (SEQ ID NO.: 248) | TLNDLETDV (SEQ ID NO.: 310) | YLIIGILTL (SEQ ID NO.: 373) | SLFLGILSV (SEQ ID NO.: 434) | NGVRVLATA (SEQ ID NO.: 496) |
| GLSISGNLL (SEQ ID NO.: 249) | TLLANVTAV (SEQ ID NO.: 311) | GILGLVFTL (SEQ ID NO.: 374) | ALAHGVRAL (SEQ ID NO.: 435) | QLLNSVLTL (SEQ ID NO.: 497) |
| YLLPAIVHI (SEQ ID NO.: 250) | SLVNGVVRL (SEQ ID NO.: 312) | AMLNGLIYV (SEQ ID NO.: 375) | ALLALTRAI (SEQ ID NO.: 436) | ILHTNMPNV (SEQ ID NO.: 498) |
| WILGFVFTL (SEQ ID NO.: 251) | ALPHIIDEV (SEQ ID NO.: 313) | RMLPHAPGV (SEQ ID NO.: 376) | NLLIRCLRC (SEQ ID NO.: 437) | AITEVECFL (SEQ ID NO.: 499) |
| SLSAYIIRV (SEQ ID NO.: 252) | LITGRLQSL (SEQ ID NO.: 314) | LLIDLTSFL (SEQ ID NO.: 377) | SMINGVVKL (SEQ ID NO.: 438) | GMDPRMCSL (SEQ ID NO.: 500) |
| KLVCSPAPC (SEQ ID NO.: 253) | TLTSYWRRV (SEQ ID NO.: 315) | LLLGTLNIV (SEQ ID NO.: 378) | DVSRPTAVV (SEQ ID NO.: 439) | AILIRVRNA (SEQ ID NO.: 501) |
| YINTALLNA (SEQ ID NO.: 254) | FQGRGVFEL (SEQ ID NO.: 316) | FANYNFTLV (SEQ ID NO.: 379) | ALNTLVKQL (SEQ ID NO.: 440) | KTVLELTEV (SEQ ID NO.: 502) |
| ILLARLFLY (SEQ ID NO.: 255) | SLMDLLSSL (SEQ ID NO.: 317) | LGYGFVNYV (SEQ ID NO.: 380) | FIAGLIAIV (SEQ ID NO.: 441) | VLHKRTLGL (SEQ ID NO.: 503) |
| YLDKVRATV (SEQ ID NO.: 256) | FLTSVINRV (SEQ ID NO.: 318) | TLACFAVYT (SEQ ID NO.: 381) | KTWGQYWQV (SEQ ID NO.: 442) | MGNGCLRIV (SEQ ID NO.: 504) |
| FANNKFTLV (SEQ ID NO.: 257) | GILDFGVKL (SEQ ID NO.: 319) | SLNQTVHSL (SEQ ID NO.: 382) | RMSKGVFKV (SEQ ID NO.: 443) | LVMAQLLRI (SEQ ID NO.: 505) |
| LLHTDFEQV (SEQ ID NO.: 258) | QLVQSGAEV (SEQ ID NO.: 320) | RLNTVLATA (SEQ ID NO.: 383) | ILYGPLTRI (SEQ ID NO.: 444) | AMLDLLKSV (SEQ ID NO.: 506) |
| FLYELIWNV (SEQ ID NO.: 259) | YLLKPVQRI (SEQ ID NO.: 321) | IVSPFIPLL (SEQ ID NO.: 384) | HLSRGLPV (SEQ ID NO.: 445) | IADAALAAL (SEQ ID NO.: 507) |
| LLCGNLLIL (SEQ ID NO.: 260) | SLPITVYYA (SEQ ID NO.: 322) | LLIEGIFFI (SEQ ID NO.: 385) | SLFGGMSWI (SEQ ID NO.: 446) | DLSLRRFMV (SEQ ID NO.: 508) |
| LIDQYLYYL (SEQ ID NO.: 261) | AIMDKNITL (SEQ ID NO.: 323) | SIVAYTMSL (SEQ ID NO.: 386) | LLLLDVAPL (SEQ ID NO.: 447) | LQDIEITCV (SEQ ID NO.: 509) |
| LLYNCCYHV (SEQ ID NO.: 262) | RINAILATA (SEQ ID NO.: 324) | ELLRPTTLV (SEQ ID NO.: 387) | FLMEDQTLL (SEQ ID NO.: 448) | KLQEQQSDL (SEQ ID NO.: 510) |
| RDVPMLITT (SEQ ID NO.: 263) | FVNHRFTLV (SEQ ID NO.: 325) | FAFKDLFVV (SEQ ID NO.: 388) | AMDSNTLEL (SEQ ID NO.: 449) | FLTCTDRSV (SEQ ID NO.: 511) |
| PESSQRPPL (SEQ ID NO.: 264) | LLSLFSLWL (SEQ ID NO.: 326) | NIVCPLCTL (SEQ ID NO.: 389) | ITNCLLSTA (SEQ ID NO.: 450) | SVGGVFTSV (SEQ ID NO.: 512) |

TABLE 9-continued

Peptides classified as Immunogenic in the IEDB database used for developing the TCR-binding algorithm

| LMGDKSENV (SEQ ID NO.: 265) | ALAEGDLLA (SEQ ID NO.: 327) | GGPNLDNIL (SEQ ID NO.: 389) | ILIEGIFFA (SEQ ID NO.: 451) |
| RLNELLAYV (SEQ ID NO.: 266) | TLARGFPIN (SEQ ID NO.: 328) | TIPEALAAV (SEQ ID NO.: 390) | DLMGYIPAV (SEQ ID NO.: 452) |
| RLWHYPCTI (SEQ ID NO.: 267) | LIFLARSAL (SEQ ID NO.: 329) | TLLYVLFEV (SEQ ID NO.: 391) | AMLVLLAEI (SEQ ID NO.: 453) |

TABLE 10

Performance metrices for the different classifiers on unseen dataset

| Performance metric | FILA binding classifier | Ensemble classifier1 | Ensemble classifier2 | Ensemble classifier3 |
|---|---|---|---|---|
| TP | 228 | 183 | 220 | 277 |
| FP | 84 | 44 | 9 | 1 |
| TN | 32 | 72 | 107 | 115 |
| FN | 78 | 124 | 87 | 30 |
| Sensitivity (%) | 74.50% | 59.61 | 71.66 | 90.23 |
| Specificity (%) | 27.59% | 62.07 | 92.24 | 99.14 |
| Accuracy (%) | 61.61% | 60.28 | 77.30 | 92.67 |

TP: True Positive (Immunogenic peptide predicted as immunogenic)
FP: False Positive (Non-immunogenic peptide predicted as immunogenic)
TN: True Negative (Non-immunogenic peptide predicted as non-immunogenic)
FN: False Negative (Non-immunogenic peptide predicted as immunogenic)
HLA binding classifier: If the peptide binding affinity using NetMHCcons program is <= 500 nM then it is taken as immunogenic peptide and rest other as non-immunogenic peptide
Ensemble classifier1: The ensemble J4.8 classifier built using 500 classifiers using all features for the peptides.
Ensemble classifier2: The ensemble J4.8 classifier built using 433 classifiers using reduced features for the peptides.
Ensemble classifier3: The ensemble J4.8 classifier built using 45 best individual classifiers using reduced features for the peptides.

TABLE 11

List of selected features defining hydrophobicity and helix/turn and their position in peptide and their frequency in immunogenic peptides

| Frequency | Position in 9mer | Feature ID[1,2] | Feature Type | Brief description |
|---|---|---|---|---|
| 12 | 8,9 | RACS820104 | helix/turn | Average relative fractional occurrence in EL |
| 7 | 8,9 | JOND750102 | hydrophobicity | pK (—COOH) |
| 7 | 3 | TANS770108 | helix/turn | Normalized frequency of zeta R |
| 7 | 4,5 | RICJ880115 | helix/turn | Relative preference value at C-cap |
| 6 | 5,6 | RICJ880109 | helix/turn | Relative preference value at Mid |
| 6 | 6 | PALJ810109 | helix/turn | Normalized frequency of alpha-helix in alpha/beta class |
| 5 | 1,2,3,4,5,6,7,8,9 | NAKH920106 | helix/turn | AA composition of CYT of multi-spanning proteins |
| 4 | 2 | MEEJ800102 | hydrophobicity | Retention coefficient in HPLC |
| 4 | 8,9 | CEDJ970101 | hydrophobicity | Composition of amino acids in extracellular proteins |
| 4 | 1,2,3,4,5,6,7,8,9 | WILM950103 | hydrophobicity | Hydrophobicity coefficient in RP-HPLC |
| 4 | 2,3 | RICJ880104 | helix/turn | Relative preference value at N1 |
| 4 | 7,8 | QIAN880137 | helix/turn | Weights for coil at the window position of 4 |
| 4 | 8,9 | PALJ810108 | helix/turn | Normalized frequency of alpha-helix in alpha + beta class |
| 4 | 1,2,8,9 | QIAN880127 | helix/turn | Weights for coil at the window position of −6 |
| 4 | 3,4,5,6,7,8 | SUYM030101 | helix/turn | Linker propensity index |
| 3 | 2,3 | WILM950104 | hydrophobicity | Hydrophobicity coefficient in RP-HPLC |
| 3 | 3 | WILM950103 | hydrophobicity | Hydrophobicity coefficient in RP-HPLC |
| 3 | 1,2,3,4,5,6,7,8,9 | WILM950104 | hydrophobicity | Hydrophobicity coefficient in RP-HPLC |
| 3 | 1,2,3,4,5,6,7,8,9 | NAKH900108 | hydrophobicity | Normalized composition from fungi and plant |
| 3 | 1,2 | RACS820107 | helix/turn | Average relative fractional occurrence in A0 |
| 3 | 1,2 | ROBB760111 | helix/turn | Information measure for C-terminal turn |
| 3 | 1,2 | TANS770102 | helix/turn | Normalized frequency of isolated helix |
| 3 | 1,2 | QIAN880139 | helix/turn | Weights for coil at the window position of 6 |
| 3 | 2,3 | RICJ880113 | helix/turn | Relative preference value at C2 |
| 3 | 5,6 | RICJ880105 | helix/turn | Relative preference value at N2 |
| 3 | 6 | CHOP780204 | helix/turn | Normalized frequency of N-terminal helix |
| 3 | 6,7 | PALJ810108 | helix/turn | Normalized frequency of alpha-helix in alpha + beta class |
| 3 | 6,7 | PALJ810113 | helix/turn | Normalized frequency of turn in all-alpha class |
| 3 | 3,4,5,6,7,8 | RACS820107 | helix/turn | Average relative fractional occurrence in A0 |

TABLE 11-continued

List of selected features defining hydrophobicity and helix/turn and their position in peptide and their frequency in immunogenic peptides

| Frequency | Position in 9mer | Feature ID[1,2] | Feature Type | Brief description |
|---|---|---|---|---|
| 3 | 3,4,5,6,7,8 | RICJ880110 | helix/turn | Relative preference value at C5 |
| 3 | 1,2,3,4,5,6,7,8,9 | SUYM030101 | helix/turn | Linker propensity index |
| 2 | 1,2,3,4,5,6,7,8,9 | XLogP.VAR | hydrophobicity | An estimate of the logP partition coefficient |
| 2 | 2,3 | KIDA850101 | hydrophobicity | Hydrophobicity-related index |
| 2 | 3 | RADA880101 | hydrophobicity | Transfer free energy from chx to wat |
| 2 | 3 | RADA880104 | hydrophobicity | Transfer free energy from chx to oct |
| 2 | 3 | WILM950104 | hydrophobicity | Hydrophobicity coefficient in RP-HPLC |
| 2 | 5,6 | BULH740102 | hydrophobicity | Apparent partial specific volume |
| 2 | 6 | CIDH920103 | hydrophobicity | Normalized hydrophobicity scales for alpha + beta-proteins |
| 2 | 6,7 | RADA880107 | hydrophobicity | Energy transfer from out to in (95% buried) |
| 2 | 6,7 | PONP800103 | hydrophobicity | Average gain ratio in surrounding hydrophobicity |
| 2 | 1,2,8,9 | KANM800104 | hydrophobicity | Average relative probability of inner beta-sheet |
| 2 | 1,2,3,4,5,6,7,8,9 | ZASB820101 | hydrophobicity | Dependence of partition coefficient on ionic strength |
| 2 | 1 | SUEM840102 | helix/turn | Zimm-Bragg parameter sigma x 1.0E4 |
| 2 | 1,2 | PALJ810108 | helix/turn | Normalized frequency of alpha-helix in alpha + beta class |
| 2 | 1,2 | LEVM780104 | helix/turn | Normalized frequency of alpha-helix |
| 2 | 1,2 | RICJ880104 | helix/turn | Relative preference value at N1 |
| 2 | 2 | GEIM800109 | helix/turn | Aperiodic indices for alpha-proteins |
| 2 | 2 | ROBB760111 | helix/turn | Information measure for C-terminal turn |
| 2 | 2 | QIAN880112 | helix/turn | Weights for alpha-helix at the window position of 5 |
| 2 | 2,3 | CHOP780212 | helix/turn | Frequency of the 1st residue in turn |
| 2 | 2,3 | BUNA790101 | helix/turn | alpha-NH chemical shifts |
| 2 | 2,3 | RICJ880114 | helix/turn | Relative preference value at C1 |
| 2 | 3 | RACS820103 | helix/turn | Average relative fractional occurrence in AL |
| 2 | 3,4 | RICJ880109 | helix/turn | Relative preference value at Mid |
| 2 | 4,5 | RICJ880113 | helix/turn | Relative preference value at C2 |
| 2 | 5,6 | RACS820105 | helix/turn | Average relative fractional occurrence in E0 |
| 2 | 6 | CHOP780213 | helix/turn | Frequency of the 2nd residue in turn |
| 2 | 6 | RACS820106 | helix/turn | Average relative fractional occurrence in ER |
| 2 | 6 | PALJ810107 | helix/turn | Normalized frequency of alpha-helix in all-alpha class |
| 2 | 6 | QIAN880106 | helix/turn | Weights for alpha-helix at the window position of -1 |
| 2 | 6,7 | MAXF760103 | helix/turn | Normalized frequency of zeta R |
| 2 | 6,7 | QIAN880137 | helix/turn | Weights for coil at the window position of 4 |
| 2 | 7,8 | QIAN880101 | helix/turn | Weights for alpha-helix at the window position of -6 |
| 2 | 8,9 | QIAN880102 | helix/turn | Weights for alpha-helix at the window position of -5 |
| 2 | 8,9 | NAKH920101 | helix/turn | AA composition of CYT of single-spanning proteins |
| 2 | 3,4,5,6,7,8 | RICJ880109 | helix/turn | Relative preference value at Mid |

[1]Amino acid index
[2]PepLib library ID

Example 1a

A method of selecting immunogenic peptide from a peptide sequence

TCR binding prediction

Features of amino acids at each of the 9 positions of the 9-mer peptide considered for predicting immunogenicity

| Feature number | Feature value | Feature ID | Feature description |
|---|---|---|---|
| f1 | Average value of position 5, 6 | RICJ880105[1] | Relative preference value at N2 (Richardson-Richardson) |
| f2 | Average value of position 1, 2, 8, 9 | QIAN880107[1] | Weights for alpha-helix at the window position of 0 (Qian-Sejnowski) |
| f3 | Average value of position 8, 9 | YUTK870103[1] | Activation Gibbs energy of unfolding |
| f4 | Value of position 3 | FNSA.2[2] | a combination of surface area and partial charge |
| f5 | Average value of position 6, 7 | VASM830101[1] | Relative population of conformational state A (Vasquez et al.) |
| f6 | Average value of position 6, 7 | ROBB760108[1] | Information measure for turn (Robson-Suzuki) |
| f7 | Average value of position 1-9 | NAKH920106[1] | AA composition of CYT of multi-spanning proteins (Nakashima-Nishikawa) |
| f8 | Average value of position 2, 3 | QIAN880139[1] | Weights for coil at the window position of 6 (Qian-Sejnowski) |
| f9 | Average value of position 7, 8 | QIAN880138[1] | Weights for coil at the window position of 5 (Qian-Sejnowski) |
| f10 | Average value of position 1-9 | CHAM830103[1] | The number of atoms in the side chain labelled 1 + 1 (Charton-Charton) |
| f11 | Average value of position 5, 6 | YUTK870103[1] | Activation Gibbs energy of unfolding |
| f12 | Average value of position 1, 2 | MITS020101[1] | Amphiphilicity index (Mitaku et al.) |

-continued

| Feature number | Feature value | Feature ID | Feature description |
|---|---|---|---|
| f13 | Value of position 2 | PNSA.1.AUTO[2] | a combination of surface area and partial charge |
| f14 | Value of position 3 | KARS160118[1] | Average weighted atomic number or degree based on atomic number in the graph (Karkbara-Knisley) |
| f15 | Average value of position 8, 9 | YUTK870104[1] | Activation Gibbs energy of unfolding |

Rules for predicting immunogenicity based on the features of amino acids at each of the 9 positions of the 9-mer peptide. The rules specify the range of parameters that define the identity of each amino acid at each position of the 9-mer peptide Rule 1: f1<=0.5

Rule 2: f1>0.5 AND f2<=-0.77

Rule 3: f1>0.5 AND f2>-0.77 AND f3<=17.75

Rule 4: f1>0.5 AND f2>-0.77 AND f3>17.75 AND f4<=-0.34 AND f5<=0.2055

Rule 5: f1>0.5 AND f2>-0.77 AND f3>17.75 AND f4>-0.34 AND f6<=-5.5

Rule 6: f1>0.5 AND f2>-0.77 AND f3>17.75 AND f4>-0.34 AND f6>-5.5 AND f7<=45.56 AND f8>-0.055

Rule 7: f1>0.65 AND f2>-0.77 AND f3>17.75 AND f4>-0.34 AND f6>-5.5 AND f7>45.56 AND f8>-0.055 AND f9<=-0.23 AND f10>7.0

Rule 8: f1>0.5 AND f2>-0.77 AND f3>17.75 AND f4>-0.34 AND f6>-5.5 AND f7>45.56 AND f9>-0.23 AND 112<=0.625 AND f13<=0.144401 AND f13>-0.303435 AND f14<=6.8 AND f15<=18.04

Rule 9: f1>0.5 AND f2>-0.77 AND f3>17.75 AND f4>-0.34 AND f6>-5.5 AND f7>45.56 AND f9>-0.23 AND f12<=0.625 AND f13<=0.144401 AND f14>6.8 AND f11<=17.92

Rule 10: f1>0.5 AND f2>-0.77 AND f3>17.75 AND f4>-0.34 AND f6>-5.5 AND f7>45.56 AND f9>-0.23 AND f12<=0.625 AND f13>0.144401

Rules for Rank Ordering of Immunogenic Peptides

TABLE 12

Method of rank ordering immunogenic peptides

| Steps as shown in FIG. 1 | Output from the steps | Score |
|---|---|---|
| TCR binding (Step-10) | Positive by Ensemble model-2 and 3 | 3 |
|  | Positive by Ensemble model 3 only | 2 |
|  | Positive by Ensemble model-2 only | 1 |
|  | Negative by both Ensemble model 2 and 3 | 0 |
| MHC binding (IC$_{50}$) (Step-11) | <=100 nM | 4 |
|  | >100 nM, <=500 nM | 3 |
|  | >500 nM, <=1000 nM | 2 |
|  | >1000 nM | 1 |
| Expression of the mutant allele (Step-7) | =0 | 0 |
|  | 1-5 (read count) | 1 |
|  | 6-10 (read count) | 2 |
|  | 11-50 (read count) | 3 |
|  | >50 (read count) | 4 |
| TAP binding (Step-12) | <0.5 | 3 |
|  | >=0.5 | 1 |
| Proteasomal cleavage (Step-13) | <10.0 | 1 |
|  | >=10 | 3 |

Scores are combined to create a rank ordered score for each peptide.

Example 2

The example demonstrates an exemplary methodology for predicting immunogenic peptide from a human Head and Neck cancer sample starting from human cancer tissue sample Exome Sequencing The exome sequencing was performed for the tumor and normal samples. The exome capturing was performed using Agilent SureSelect Human All Exon V5 kit. The RNA sequencing (RNA-seq) was performed for the total RNA extracted after Ribo-depletion of tumor sample RNA. All paired-end sequencing was performed using Illumina HiSeq 2500 platform. Total data obtained for the exome-seq and RNA-seq sample exceeds 12 Gb and more than 90% of data exceed Q30 (shown in Table 12).

The exome-seq data is first pre-processed, where we remove the low quality reads/bases and adapter sequences. The pre-processed reads is then aligned to the human reference genome (hg19) using BWA program with default parameters. Then, we apply GATK-best practices where we remove the duplicate reads using Picard tools and re-align, re-calibrate using GATK and keep the file ready for somatic mutation identification (Table 13). The somatic mutations in the samples are identified using Strelka program. After this, only the quality passed and on-target mutations are processed further. A total of 222 mutations were identified in this sample. Of these 210 are SNPs and 12 are Indels (Table 14). Of the total coding mutations, 106 of them are of missense type (Table 16).

RNA Sequencing

The RNA-seq data is first pre-processed, where we remove the low quality reads/bases, adapter sequences and unwanted sequences like ribosomal RNA, tRNAs, repeat sequences. The pre-processed reads is then aligned to human reference transcriptome and genome using STAR aligner (Table 17). The expression of the gene is then identified using Cufflinks program.

HLA-Typing

The RNA-seq data is then used for HLA typing [27, 28]. We used Seq2HLA program for HLA typing from RNA-seq. The Class-I HLA alleles identified for this sample is provided in Table 18. The expression of the HLA genes is provided in Table 19. The read depth of the mutant allele in RNA-seq is then calculated. Of the total mutations, we found 62 mutations with read support >=1 in RNA-seq. These mutations are also termed as expressed mutations. The 62 mutations generated 578 unique 9-mer peptides.

Immunogenic Peptide Identification

The peptides derived from the expressed mutations were scored for TCR-binding followed by HLA binding prediction, then TAP prediction and finally proteasomal processing. The immunogenic peptides were further ranked based on the expression level of genes and variants, affinity of HLA binding, sensitivity to proteasomal processing and binding to the transporter. We applied the ranking method to 220 unique immunogenic peptides from this Head and Neck cancer sample. The ranked peptide along with HLA information is provided in Table 20.

TABLE 13

Summary of data generated from head and neck cancer tumor and paired normal sample

| Data Metrics | Exome-seq | | RNA-seq |
| --- | --- | --- | --- |
| | Blood | Tumor | Tumor |
| Total reads | 12,65,08,302 | 12,38,71,688 | 136,893,000 |
| Total data (Gb) | 12.65 | 12.39 | 13.69 |
| Average read length (bp) | 100 | 100 | 100 |
| GC (%) | 48.98 | 49.85 | 54.55 |
| Average base quality (Phred) | 39.90 | 39.74 | 34.97 |
| Total data >= Q30 (%) | 96.91 | 96.39 | 90.62 |

TABLE 14

Preprocessing, alignment and coverage summary of exome sequencing data

| Data and analysis metrics | Blood | Tumor |
| --- | --- | --- |
| Total reads after pre-processing | 12,64,41,480 | 12,38,71,678 |
| Total data after pre-processing (Gb) | 12.63 | 12.38 |
| Average read length (bp) | 99.91 | 99.94 |
| Average base quality (Phred) | 39.72 | 39.56 |
| Data <=Q30 (%) after pre-processing | 96.96 | 96.45 |
| Total aligned reads | 126,390,638 | 123,793,462 |
| Alignment (%) | 99.96 | 99.94 |
| Duplicate (%) | 14.98 | 16.20 |
| Panel length | 5,03,90,601 | 5,03,90,601 |
| Panel Coverage (%) | 99.85 | 99.84 |
| Panel Ontarget Region Avg. Depth | 111.01 | 130.42 |
| On-target (%) | 62.61 | 75.75 |

TABLE 15

Summary of variants detected in the sample

| | |
| --- | --- |
| Total variants | 222 |
| Total SNPs | 210 |
| Total Indels | 12 |
| Transition SNPs | 136 |
| Transversion SNPs | 74 |
| Ts/Tv | 1.84 |

TABLE 16

Classification of protein-altering variants

| Variant Class | # of mutations |
| --- | --- |
| Missense | 106 |
| Frameshift | 3 |
| InFrame | 3 |
| Total | 112 |

Missense - Genetic alteration that results in a different amino acid.
Frameshift - Genetic alteration that changes the reading frame. This typically results in a string of different amino acids substitutions before encountering a stop codon.
InFrame - Genetic alteration that results in either deletion or insertion of one or more amino acids.

TABLE 17

Pre-processing and alignment summary of RNA sequence data

| | |
| --- | --- |
| Read Count After Adapter Trimming | 133,225,190 |
| Read Count After Contamination Removal | 92,623,074 |
| Reads Aligned | 75,489,728 |
| Reads Unaligned | 17,133,346 |
| Reads Aligned % | 81.50 |
| % data lost after Pre-Precessing | 32.34 |

TABLE 18

HLA class I alleles present in the sample

| | |
| --- | --- |
| HLA-A | HLA-A33:03, HLA-A02:01 |
| HLA-B | HLA-B58:01, HLA-B35:01 |
| HLA-C | HLA-C03:02, HLA-C04:01 |

TABLE 19

Expression of HLA class I genes in the sample

| HLA gene | Gene Expression (RPKM) |
| --- | --- |
| HLA-A | 657.30 |
| HLA-B | 987.41 |
| HLA-C | 691.26 |

TABLE 20

Rank ordered list of immunogenic peptides from the mutations in head and neck cancer sample

| Rank | Gene | Amino acid change | Mutant Peptide (9mer) | HLA Types |
| --- | --- | --- | --- | --- |
| 1 | PIK3CA | p.E542K | strdpls(K)i (SEQ ID NO.: 513) | HLA-B35:01,HLA-A02:01,HLA-B58:01,HLA-C04:01,HLA-C03:02,HLA-A33:03 |
| 2 | BRPF3 | p.R570W | rllieli(W)k (SEQ ID NO.: 514) | HLA-B35:01,HLA-A02:01,HLA-858:01,HLA-C04:01,HLA-C03:02,HLA-A33:03 |
| 3 | ZBTB6 | p.E196Q | stvesIts(Q) (SEQ ID NO.: 515) | HLA-B35:01,HLA-A02:01,HLA-B58:01,HLA-C04:01,HLA-C03:02,HLA-A33:03 |
| 3 | BRPF3 | p.R570W | llieli(W)kr (SEQ ID NO.: 516) | HLA-A33:03 |
| 5 | BRPF3 | p.R570W | lieli(W)kre (SEQ ID NO.: 517) | HLA-B35:01,HLA-A02:01,HLA-B58:01,HLA-C04:01,HLA-C03:02,HLA-A33:03 |
| 6 | PIK3CA | p.E542K | (K)iteigekdf (SEQ ID NO.: 518) | HLA-B35:01,HLA-A02:01,HLA-B58:01,HLA-C04:01,HLA-C03:02,HLA-A33:03 |
| 7 | ZBTB6 | p.E196Q | lts(Q)rkemk (SEQ ID NO.: 519) | HLA-B35:01,HLA-A02:01,HLA-B58:01,HLA-C04:01,HLA-C03:02,HLA-A33:03 |
| 8 | BRPF3 | p.R570W | lieli(W)kr (SEQ ID NO.: 516) | HLA-B35:01,HLA-A02:01,HLA-B58:01,HLA-C04:01,HLA-C03:02 |

REFERENCES

1. Schumacher, T. N. and R. D. Schreiber, *Neoantigens in cancer immunotherapy*. Science, 2015. 348(6230): p. 69-74.
2. Gubin, M. M., et al., *Tumor neoantigens: building a framework for personalized cancer immunotherapy*. J Clin Invest, 2015. 125(9): p. 3413-21.

3. van der Burg, S. H., et al., *Vaccines for established cancer: overcoming the challenges posed by immune evasion.* Nat Rev Cancer, 2016. 16(4): p. 219-33.
4. Romero, P., et al., *The Human Vaccines Project: A roadmap for cancer vaccine development.* Sci Transl Med, 2016. 8(334): p. 334ps9.
5. Yadav, M., et al., *Predicting immunogenic tumour mutations by combining mass spectrometry and exome sequencing.* Nature, 2014. 515(7528): p. 572-6.
6. Vaughan, K., et al., *Deciphering the MHC-associated peptidome: a review of naturally processed ligand data.* Expert Rev Proteomics, 2017: p. 1-8.
7. Wieczorek, M., et al., *Major Histocompatibility Complex (MHC) Class I and MHC Class II Proteins: Conformational Plasticity in Antigen Presentation.* Front Immunol, 2017. 8: p. 292.
8. Basler, M., C. J. Kirk, and M. Groettrup, *The immunoproteasome in antigen processing and other immunological functions.* Curr Opin Immunol, 2013. 25(1): p. 74-80.
9. Eggensperger, S. and R. Tampe, *The transporter associated with antigen processing: a key player in adaptive immunity.* Biol Chem, 2015. 396(9-10): p. 1059-72.
10. Mahmutefendic, H., et al., *Endosomal trafficking of open Major Histocompatibility Class I conformers—implications for presentation of endocytosed antigens.* Mol Immunol, 2013. 55(2): p. 149-52.
11. Roche, P. A. and K. Furuta, *The ins and outs of MHC class II-mediated antigen processing and presentation.* Nat Rev Immunol, 2015. 15(4): p. 203-16.
12. Neefjes, J., et al., *Towards a systems understanding of MHC class I and MHC class II antigen presentation.* Nat Rev Immunol, 2011. 11(12): p. 823-36.
13. Leavy, O., *Antigen presentation: cross-dress to impress.* Nat Rev Immunol, 2011. 11(5): p. 302-3.
14. Joffre, O. P., et al., *Cross-presentation by dendritic cells.* Nat Rev Immunol, 2012. 12(8): p. 557-69.
15. Branca, M. A., *Rekindling cancer vaccines.* Nat Biotechnol, 2016. 34(10): p. 1019-1024.
16. Ott, P. A., et al., *An immunogenic personal neoantigen vaccine for patients with melanoma.* Nature, 2017. 547 (7662): p. 217-221.
17. Sahin, U., et al., *Personalized RNA mutanome vaccines mobilize poly-specific therapeutic immunity against cancer.* Nature, 2017. 547(7662): p. 222-226.
18. Carreno, B. M. and E. R. Mardis, *A Vaccine for Cancer?* Sci Am, 2016. 314(4): p. 46.
19. Carreno, B. M., et al., *Cancer immunotherapy. A dendritic cell vaccine increases the breadth and diversity of melanoma neoantigen-specific T cells.* Science, 2015. 348(6236): p. 803-8.
20. Liu, X. S. and E. R. Mardis, *Applications of Immunogenomics to Cancer.* Cell, 2017. 168(4): p. 600-612.
21. Hundal, J., et al., *Cancer Immunogenomics: Computational Neoantigen Identification and Vaccine Design.* Cold Spring Harb Symp Quant Biol, 2016. 81: p. 105-111.
22. Turajlic, S., et al., *Insertion-and-deletion-derived tumour-specific neoantigens and the immunogenic phenotype: a pan-cancer analysis.* Lancet Oncol, 2017. 18(8): p. 1009-1021.
23. Romero Arenas, M. A., et al., *Preliminary whole-exome sequencing reveals mutations that imply common tumorigenicity pathways in multiple endocrine neoplasia type 1 patients.* Surgery, 2014. 156(6): p. 1351-7; discussion 1357-8.
24. Karosiene, E., et al., *NetMHCcons: a consensus method for the major histocompatibility complex class I predictions.* Immunogenetics, 2012. 64(3): p. 177-86.
25. Nielsen, M., et al., *The role of the proteasome in generating cytotoxic T-cell epitopes: insights obtained from improved predictions of proteasomal cleavage.* Immunogenetics, 2005. 57(1-2): p. 33-41.
26. Hall, M. A., *Correlation-based Feature Selection for Machine Learning.* 1999.
27. Sidney, J., et al., *HLA class I supertypes: a revised and updated classification.* BMC Immunol, 2008. 9: p. 1.
28. Greenbaum, J., et al., *Functional classification of class II human leukocyte antigen (HLA) molecules reveals seven different supertypes and a surprising degree of repertoire sharing across supertypes.* Immunogenetics, 2011. 63(6): p. 325-35.

What is claimed is:

1. A method of selecting mammalian tumor immunogenic peptides from genetically altered proteins expressed by a mammalian tumor cell or a mammalian tumor tissue from a subject, which method comprises:
   a) obtaining a sample from the subject;
   b) identifying genetically altered proteins expressed by a mammalian tumor cell or a mammalian tumor tissue in the sample through nucleic acid sequences encoding the altered proteins;
   c) producing peptide fragments comprising at least one amino acid mutation from the genetically altered proteins so identified in step (b), so as to obtain peptide variants associated with the mammalian tumor cell or the mammalian tumor tissue;
   d) selecting peptide variants from step c which bind T-cell receptor (TCR) comprising:
      i) selecting peptide variants with a pre-defined length of 9 amino acids;

ii) characterizing the peptide variants in silico by selecting and matching features associated with an amino acid at each position of the peptide variants with selected pre-defined features of hydrophobic and helix/turn motif for each position of peptides recognized by TCR associated with CD8+ T-cell, so as to obtain predictive ability of the peptide variants to interact with the TCR and identifying peptide variants having the matching selected pre-defined features; and iii) selecting the peptide variants in step d.ii by:

A. applying RICJ880105 and QIAN880107 helix/turn motif scales and a YUTK870103 hydrophobic scale and selecting peptide variants having:

(a) at positions 5 and 6 an average value greater than 0.5 using a RICJ880105 helix/turn motif scale, (b) at positions 1, 2, 8, and 9 an average value greater than −0.77 using a QIAN880107 helix/turn scale, and (c) at positions 8 and 9 an average value less than or equal to 17.75 using a YUTK870103 hydrophobic scale;

B. applying RICJ880105 and QIAN880107 helix/turn motif scales and a YUTK870103 hydrophobic scale and selecting peptide variants having:

(a) at positions 5 and 6 an average value greater than 0.5 using a RICJ880105 helix/turn motif scale, (b) at positions 1, 2, 8, and 9 an average value greater than −0.77 using a QIAN880107 helix/turn scale, (c) at positions 8 and 9 an average value greater than 17.75 using a YUTK870103 hydrophobic scale, (d) at position 3 a value less than or equal to −0.34 using a FNSA.2 charge of side chain scale, and (e) at positions 6 and 7 an average value less than or equal to 0.2055 using a VASM830101 scale for spatial flexibility of side chain and spatial flexibility of main chain;

C. applying using RICJ880105 and QIAN880107 helix/turn motif scales and a YUTK870103 hydrophobic scale and selecting peptide variants having:

(a) at positions 5 and 6 an average value greater than 0.5 using a RICJ880105 helix/turn motif scale, (b) at positions 1, 2, 8, and 9 an average greater than −0.77 using a QIAN880107 helix/turn motif scale, (c) at positions 8 and 9 an average value greater than 17.75 using a YUTK870103 hydrophobic scale, (d) at position 3 a value greater than −0.34 using a FNSA.2 charge of side chain scale, and (e) at positions 6 and 7 an average value less than or equal to −5.5 using a ROBB760108 helix/turn scale;

D. applying RICJ880105 and QIAN880107 helix/turn motif scales and a YUTK870103 hydrophobic scale and selecting peptide variants having:

(a) at positions 5 and 6 an average value greater than 0.5 using a RICJ880105 helix/turn motif scale, (b) at positions 1, 2, 8, and 9 an average value greater than −0.77 using a QIAN880107 helix/turn motif scale, (c) at positions 8 and 9 an average value greater than 17.75 using a YUTK870103 hydrophobic scale, (d) at position 3 a value greater than −0.34 using a FNSA.2 charge of side chain scale, (e) at positions 6 and 7 an average value greater than −5.5 using a ROBB760108 helix/turn scale, (f) at positions 1-9 an average value less than or equal to 45.56 using a NAKH920106 helix/turn motif scale, and (g) at positions 2 and 3 an average value greater than −0.055 using a QIAN880139 helix/turn motif scale;

E. applying RICJ880105 and QIAN880107 helix/turn motif scales and a YUTK870103 hydrophobic scale and selecting peptide variants having:

(a) at positions 5 and 6 an average value greater than 0.65 using a RICJ880105 helix/turn motif scale, (b) at positions 1, 2, 8, and 9 an average value greater than −0.77 using a QIAN880107 helix/turn motif scale, (c) at positions 8 and 9 an average value greater than 17.75 using a YUTK870103 hydrophobic scale, (d) at position 3 a value greater than −0.34 using a FNSA.2 charge of side chain scale, (e) at positions 6 and 7 an average value greater than −5.5 using a ROBB760108 helix/turn scale, (f) at positions 1-9 an average value greater than 45.56 using a NAKH920106 helix/turn motif scale, (g) at positions 2 and 3 an average value greater than −0.055 using a QIAN880139 helix/turn motif scale, (h) at positions 7 and 8 an average value less than or equal to −0.23 using a QIAN880138 helix/turn motif scale, and (i) at positions 1-9 an average value greater than 7.0 using a CHAM830103 steric scale;

F. applying RICJ880105, QIAN880107, ROBB760108, NAKH920106 and QIAN880138 helix/turn motif scales and a YUTK870103 hydrophobic scale and selecting peptide variants having:

(a) at positions 5 and 6 an average value greater than 0.5 using a RICJ880105 helix/turn motif scale, (b) at positions 1, 2, 8, and 9 an average value greater than −0.77 using a QIAN880107 helix/turn motif scale, (c) at positions 8 and 9 an average value greater than 17.75 using a YUTK870103 hydrophobic scale, (d) at position 3 a value greater than −0.34 using a FNSA.2 charge of side chain scale, (e) at positions 6 and 7 an average value greater than −5.5 using a ROBB760108 helix/turn scale, (f) at positions 1-9 an average value greater than 45.56 using a NAKH920106 helix/turn motif scale, (g) at positions 7 and 8 an average value greater than −0.23 using a QIAN880138 helix/turn motif scale, (h) at positions 1 and 2 an average value less than or equal to 0.625 using a MITS020101 solvent accessibility of an amino acid scale, (i) at positions 2 a value less than or equal to 0.144401 using PNSA.1.AUTO charge of side chain scale, (j) at position 2 a value greater than −0.303435 using a PNSA.1.AUTO charge of side chain scale, (k) at position 3 a value less than or equal to 6.8 using a KARS160118 amino frequency scale, and (l) at positions 8 and 9 an average value less than or equal to 18.04 using a YUTK870104 hydrophobic scale;

G. applying RICJ880105, QIAN880107, ROBB760108, NAKH920106 and QIAN880138 helix/turn motif scales and a YUTK870103 hydrophobic scale and selecting peptide variants having:

(a) at positions 5 and 6 an average value greater than 0.5 using a RICJ880105 helix/turn motif scale, (b) at positions 1, 2, 8, and 9 an average value greater than −0.77 using a QIAN880107 helix/turn motif scale, (c) at positions 8 and 9 an average value greater than 17.75 using a YUTK870103 hydrophobic scale, (d) at position 3 a value greater than −0.34 using a FNSA.2 charge of side chain scale, (e) at positions 6 and 7 an average value greater than −5.5 using a ROBB760108 helix/turn scale, (f) at positions 1-9 an average value greater than 45.56 using a NAKH920106 helix/turn motif scale, (g) at positions 7 and 8 an average value greater than −0.23 using a QIAN880138 helix/turn motif scale,
(h) at positions 1 and 2 an average value less than or equal to 0.625 using a MITS020101 solvent accessibility of an amino acid scale,
(i) at position 2 a value less than or equal to 0.144401 using a PNSA.1.AUTO charge of side chain scale,
(j) at position 3 a value greater than 6.8 using a KARS160118 amino frequency scale, and
(k) at positions 5 and 6 an average value less than or equal to 17.92 using a YUTK870103 hydrophobic scale; or
H. applying RICJ880105, QIAN880107, ROBB760108, NAKH920106 and QIAN880138 helix/turn motif scales and a YUTK870103 hydrophobic scale and selecting peptide variants having:
(a) at positions 5 and 6 an average value greater than 0.5 using a RICJ880105 helix/turn motif scale,
(b) at positions 1, 2, 8, and 9 an average value greater than −0.77 using a QIAN880107 helix/turn motif scale,
(c) at positions 8 and 9 an average value greater than 17.75 using a YUTK870103 hydrophobic scale,
(d) at position 3 a value greater than −0.34 using a FNSA.2 charge of side chain scale,
(e) at positions 6 and 7 an average value greater than −5.5 using a ROBB760108 helix/turn scale,
(f) at positions 1-9 an average value greater than 45.56 using a NAKH920106 helix/turn motif scale,
(g) at positions 7 and 8 an average value greater than −0.23 using a QIAN880138 helix/turn motif scale,
(h) at positions 1 and 2 an average value less than or equal to 0.625 using a MITS020101 solvent accessibility of an amino acid scale, and
(i) at position 2 a value greater than 0.144401 using PNSA.1.AUTO charge of side chain scale;
thereby, selecting mammalian tumor immunogenic peptides from genetically altered proteins expressed by the mammalian tumor cell or the mammalian tumor tissue.

2. The method of claim 1, wherein the immunogenic peptides are further selected by potential or ability to be produced inside the cell by processes comprising:
a) determining the action of proteases, which are part of the proteasomal or immunoproteasomal complexes, based on the probability that processing event of the altered proteins will produce the immunogenic peptides so selected; and
b) determining the entry of the immunogenic peptides into the endoplasmic reticulum compartment by binding to peptide transporters expressed on the surface of the compartment.

3. The method of claim 1, wherein in step (b) identifying the genetically altered proteins expressed by the mammalian tumor cell or the mammalian tumor tissue through nucleic acid sequences encoding the altered proteins comprises:
a) identifying tumor variants from transcriptome analysis of the mammalian tumor cell or mammalian tumor tissue corresponding to protein coding and protein non-coding sequences; and
b) performing conceptual translation or in silico translation of the coding sequences in step (a) so as to identify the genetically altered proteins expressed by the mammalian tumor cell or the mammalian tumor tissue.

4. The method of claim 3, wherein in step (a) identifying tumor variants from transcriptome analysis of the mammalian tumor cell or mammalian tumor tissue comprises:
a) determining nucleotide sequence of transcripts produced by the mammalian tumor cell or mammalian tumor tissue; and
b) comparing the determined nucleotide sequence of transcripts in (a) with a reference nucleotide sequence of transcripts produced by mammalian non-tumor cell or mammalian non-tumor tissue, so as to identify nucleotide sequence changes in the protein coding and protein non-coding sequences;
thereby, identifying tumor variants from transcriptome analysis of the mammalian tumor cell or mammalian tumor tissue.

5. The method of claim 3, further comprising performing genomic analysis for tumor variants in the sequence of the genome present in the mammalian tumor cell or the mammalian tumor tissue but absent or deficient in the mammalian non-tumor cell or the mammalian non-tumor tissue.

6. The method of claim 5, wherein the genomic analysis for tumor variants comprises determining nucleotide sequence of the genome or exome.

7. The method of claim 1, wherein in step (c) producing peptide fragments comprising at least one amino acid mutation from each genetically altered protein, so as to obtain peptide variants associated with the mammalian tumor cell or the mammalian tumor tissue comprises:
a) defining length of the peptide fragments to be produced from the genetically altered protein; and
b) producing in silico peptide fragments of the pre-defined length at a site of alteration in the protein comprising at least one mutated amino acid of the genetically altered protein.

8. The method of claim 1, wherein the length of the peptide fragments to be produced from the genetically altered proteins or the peptide fragments of the pre-defined length further supports interaction with the TCR of CD8+ T-cell.

9. The method of claim 1, wherein predictive ability of the peptide variants to interact with the TCR comprises a numerical value or set of numerical values in which the value or set of numerical values is reflective of the degree of matching of the features associated with the amino acids of the peptide variants to the pre-defined features for each position of the peptides recognized by TCR-associated with CD8+ T-cell.

10. The method of claim 1, further comprising predicting a rank ordered list of immunogenic peptides derived from mammalian tumor cell or mammalian tumor tissue so selected in step d.iii, wherein rank ordering peptides is based on a combination of the following parameters:
a) expression of variant gene from which variant peptide is derived;
b) predicted ability to bind TCR of CD8+ T-cell;
c) binding affinity of the peptides to MHC class-I proteins;
d) peptide processing by immunoproteosomes or proteasomes;
e) peptide transporter binding; and
wherein each parameter may be subdivided to reflect quality of the parameter through numerical value(s) or range(s) of values, and wherein the numerical value(s) or range(s) of values from the parameters assessed or combined so as to produce output(s) permissive of sorting by ascending or descending order, thereby predicting a rank ordered list of the immunogenic peptides derived from mammalian tumor cell or mammalian tumor tissue so selected.

11. The method of claim 1, wherein selecting the immunogenic peptides further comprises HLA/MHC-typing analysis comprising:
a) determining serotype or expressed isotype or supertype of HLA/MHC proteins expressed by HLA genes of the mammalian tumor cell or tumor tissue, or alternatively of the cell or immune cell of an individual or subject to be administered with mammalian tumor immunogenic peptides comprising the selected immunogenic peptides;
b) calculating probability of HLA/MHC proteins of (a) binding mammalian tumor peptide variants with optimal processing sites from a library of tumor peptide variants;
c) calculating probability of TCR binding to generate a T-cell response;
d) selecting tumor peptide variants having highest probability from step (b) that can modulate the immune response of a mammal when challenged with the tumor peptide variants, thereby further selecting mammalian tumor immunogenic peptides dependent on HLA/MHC expression of the mammalian tumor cell or tumor tissue, or alternatively of the cell or immune cell of an individual or subject to be administered with mammalian tumor immunogenic peptides comprising the selected immunogenic peptides.

12. The method of claim 1, wherein the selected mammalian tumor immunogenic peptides from genetically altered proteins expressed by the mammalian tumor cell or the mammalian tumor tissue is any one or more of the peptides in Table 1.

13. The method of claim 1, wherein the selected predefined features for each position of peptides recognized by TCR comprise a combination of numerical indices representing physicochemical and biochemical properties of amino acids and pairs of amino acids.

14. The method of claim 1, wherein in step iii), the peptide variants so selected have:
    (a) at positions 5 and 6 an average value greater than 0.5 using RICJ880105 helix/turn motif scale,
    (b) at positions 1, 2, 8, and 9 an average value greater than −0.77 using a QIAN880107 helix/turn scale, and
    (c) at positions 8 and 9 an average value less than or equal to 17.75 using a YUTK870103 hydrophobic scale.

15. The method of claim 1, wherein in step iii), the peptide variants so selected have:
    (a) at positions 5 and 6 an average value greater than 0.5 using RICJ880105 helix/turn motif scale,
    (b) at positions 1, 2, 8, and 9 an average value greater than −0.77 using a QIAN880107 helix/turn scale,
    (c) at positions 8 and 9 an average value greater than 17.75 using a YUTK870103 hydrophobic scale,
    (d) at position 3 a value less than or equal to −0.34 using a FNSA.2 charge of side chain scale, and
    (e) at positions 6 and 7 an average value less than or equal to 0.2055 using a VASM830101 scale for spatial flexibility of side chain and spatial flexibility of main chain.

16. The method of claim 1, wherein in step iii), the peptide variants so selected have:
    (a) at positions 5 and 6 an average value greater than 0.5 using RICJ880105 helix/turn motif scale,
    (b) at positions 1, 2, 8, and 9 an average value greater than −0.77 using a QIAN880107 helix/turn motif scale,
    (c) at positions 8 and 9 an average value greater than 17.75 using a YUTK870103 hydrophobic scale,
    (d) at position 3 a value greater than −0.34 using a FNSA.2 charge of side chain scale, and
    (e) at positions 6 and 7 an average value less than or equal to −5.5 using a ROBB760108 helix/turn scale.

17. The method of claim 1, wherein in step iii), the peptide variants so selected have:
    (a) at positions 5 and 6 an average value greater than 0.5 using RICJ880105 helix/turn motif scale,
    (b) at positions 1, 2, 8, and 9 an average value greater than −0.77 using a QIAN880107 helix/turn motif scale,
    (c) at positions 8 and 9 an average value greater than 17.75 using a YUTK870103 hydrophobic scale,
    (d) at position 3 a value greater than −0.34 using a FNSA.2 charge of side chain scale,
    (e) at positions 6 and 7 an average value greater than −5.5 using a ROBB760108 helix/turn scale,
    (f) at positions 1-9 an average value less than or equal to 45.56 using a NAKH920106 helix/turn motif scale, and
    (g) at positions 2 and 3 an average value greater than −0.055 using a QIAN880139 helix/turn motif scale.

18. The method of claim 1, wherein in step iii), the peptide variants so selected have:
    (a) at positions 5 and 6 an average value greater than 0.65 using RICJ880105 helix/turn motif scale,
    (b) at positions 1, 2, 8, and 9 an average value greater than −0.77 using a QIAN880107 helix/turn motif scale,
    (c) at positions 8 and 9 an average value greater than 17.75 using a YUTK870103 hydrophobic scale,
    (d) at position 3 a value greater than −0.34 using a FNSA.2 charge of side chain scale,
    (e) at positions 6 and 7 an average value greater than −5.5 using a ROBB760108 helix/turn scale,
    (f) at positions 1-9 an average value greater than 45.56 using a NAKH920106 helix/turn motif scale, and
    (g) at positions 2 and 3 an average value greater than −0.055 using a QIAN880139 helix/turn motif scale,
    (h) at positions 7 and 8 an average value less than or equal to −0.23 using a QIAN880138 helix/turn motif scale, and
    (i) at positions 1-9 an average value greater than 7.0 using a CHAM830103 steric scale.

19. The method of claim 1, wherein in step iii), the peptide variants so selected have:
    (a) at positions 5 and 6 an average value greater than 0.5 using RICJ880105 helix/turn motif scale,
    (b) at positions 1, 2, 8, and 9 an average value greater than −0.77 using a QIAN880107 helix/turn motif scale,
    (c) at positions 8 and 9 an average value greater than 17.75 using a YUTK870103 hydrophobic scale,
    (d) at position 3 a value greater than −0.34 using a FNSA.2 charge of side chain scale,
    (e) at positions 6 and 7 an average value greater than −5.5 using a ROBB760108 helix/turn scale,
    (f) at positions 1-9 an average value greater than 45.56 using a NAKH920106 helix/turn motif scale,
    (g) at positions 7 and 8 an average value greater than −0.23 using a QIAN880138 helix/turn motif scale,
    (h) at positions 1 and 2 an average value less than or equal to 0.625 using a MITS020101 solvent accessibility of an amino acid scale,
    (i) at position 2 a value less than or equal to 0.144401 using PNSA.1.AUTO charge of side chain scale,
    (j) at position 2 a value greater than −0.303435 using PNSA.1.AUTO charge of side chain scale,
    (k) at position 3 a value less than or equal to 6.8 using a KARS160118 amino frequency scale, and
    (l) at positions 8 and 9 an average value less than or equal to 18.04 using a YUTK870104 hydrophobic scale.

20. The method of claim 1, wherein in step iii), the peptide variants so selected have:
    (a) at positions 5 and 6 an average value greater than 0.5 using RICJ880105 helix/turn motif scale,
    (b) at positions 1, 2, 8, and 9 an average value greater than −0.77 using a QIAN880107 helix/turn motif scale, (c) at positions 8 and 9 an average value greater than 17.75 using a YUTK870103 hydrophobic scale,
(d) at position 3 a value greater than −0.34 using a FNSA.2 charge of side chain scale,
(e) at positions 6 and 7 an average value greater than −5.5 using a ROBB760108 helix/turn scale,
(f) at positions 1-9 an average value greater than 45.56 using a NAKH920106 helix/turn motif scale,
(g) at positions 7 and 8 an average value greater than −0.23 using a QIAN880138 helix/turn motif scale,
(h) at positions 1 and 2 an average value less than or equal to 0.625 using a MITS020101 solvent accessibility of an amino acid scale,
(i) at positions 2 a value less than or equal to 0.144401 using a PNSA.1.AUTO charge of side chain scale,
(j) at position 3 a value greater than 6.8 using a KARS160118 amino frequency scale, and
(k) at positions 5 and 6 an average value less than or equal to 17.92 using a YUTK870103 hydrophobic scale.

21. The method of claim 1, wherein in step iii), the peptide variants so selected have a helix/turn motif
(a) at positions 5 and 6 an average value greater than 0.5 using RICJ880105 helix/turn motif scale,
(b) at positions 1, 2, 8, and 9 an average value greater than −0.77 using a QIAN880107 helix/turn motif scale,
(c) at positions 8 and 9 an average value greater than 17.75 using a YUTK870103 hydrophobic scale,
(d) at position 3 a value greater than −0.34 using a FNSA.2 charge of side chain scale,
(e) at positions 6 and 7 an average value greater than −5.5 using a ROBB760108 helix/turn scale,
(f) at positions 1-9 an average value greater than 45.56 using a NAKH920106 helix/turn motif scale,
(g) at positions 7 and 8 an average value greater than −0.23 using a QIAN880138 helix/turn motif scale,
(h) at positions 1 and 2 an average value less than or equal to 0.625 using a MITS020101 solvent accessibility of an amino acid scale, and
(i) at position 2 a value greater than 0.144401 using PNSA.1.AUTO charge of side chain scale.

22. The method of claim 1, wherein at step d.ii, the helix/turn motif so matched is applied to any of a:
a. RACS820104 helix/turn motif scale applied to positions 8 and 9 of the peptide,
b. TANS770108 helix/turn motif scale applied to position 3 of the peptide,
c. RICJ880115 helix/turn motif scale applied to positions 4 and 5 of the peptide,
d. RICJ880109 helix/turn motif scale applied to positions 5 and 6 of the peptide,
e. PALI810109 helix/turn motif scale applied to position 6 of the peptide,
f. RICJ880104 helix/turn motif scale applied to positions 2 and 3 of the peptide,
g. QIAN880137 helix/turn motif scale applied to positions 7 and 8 of the peptide,
h. PALI810108 helix/turn motif scale applied to positions 8 and 9 of the peptide,
i. QIAN880127 helix/turn motif scale applied to positions 1, 2, 8 and 9 of the peptide,
j. SUYM030101 helix/turn motif scale applied to positions 3, 4, 5, 6, 7 and 8 of the peptide,
k. RACS820107 helix/turn motif scale applied to positions 1 and 2 of the peptide,
l. ROBB760111 helix/turn motif scale applied to positions 1 and 2 of the peptide,
m. TANS770102 helix/turn motif scale applied to positions 1 and 2 of the peptide,
n. QIAN880139 helix/turn motif scale applied to positions 1 and 2 of the peptide,
o. RICJ880113 helix/turn motif scale applied to positions 2 and 3 of the peptide,
p. RICJ880105 helix/turn motif scale applied to positions 5 and 6 of the peptide,
q. CHOP780204 helix/turn motif scale applied to position 6 of the peptide,
r. PALI810108 helix/turn motif scale applied to positions 6 and 7 of the peptide,
s. PALI810113 helix/turn motif scale applied to positions 6 and 7 of the peptide,
t. RACS820107 helix/turn motif scale applied to positions 3, 4, 5, 6, 7 and 8 of the peptide,
u. RICJ880110 helix/turn motif scale applied to positions 3, 4, 5, 6, 7 and 8 of the peptide,
v. SUYM030101 helix/turn motif scale applied to positions 1, 2, 3, 4, 5, 6, 7, 8 and 9 of the peptide,
w. SUEM840102 helix/turn motif scale applied to position 1 of the peptide,
x. PALI810108 helix/turn motif scale applied to positions 1 and 2 of the peptide,
y. LEVM780104 helix/turn motif scale applied to positions 1 and 2 of the peptide,
z. RICJ880104 helix/turn motif scale applied to positions 1 and 2 of the peptide,
aa. GEIM800109 helix/turn motif scale applied to position 2 of the peptide,
bb. ROBB760111 helix/turn motif scale applied to position 2 of the peptide,
cc. QIAN880112 helix/turn motif scale applied to position 2 of the peptide,
dd. CHOP780212 helix/turn motif scale applied to positions 2 and 3 of the peptide,
ee. BUNA790101 helix/turn motif scale applied to positions 2 and 3 of the peptide,
ff. RICJ880114 helix/turn motif scale applied to positions 2 and 3 of the peptide,
gg. RACS820103 helix/turn motif scale applied to position 3 of the peptide,
hh. RICJ880109 helix/turn motif scale applied to positions 3 and 4 of the peptide,
ii. RICJ880113 helix/turn motif scale applied to positions 4 and 5 of the peptide,
jj. RACS820105 helix/turn motif scale applied to positions 5 and 6 of the peptide,
kk. CHOP780213 helix/turn motif scale applied to position 6 of the peptide,
ll. RACS820106 helix/turn motif scale applied to position 6 of the peptide,
mm. PALI810107 helix/turn motif scale applied to position 6 of the peptide,
nn. QIAN880106 helix/turn motif scale applied to position 6 of the peptide,
oo. MAXF760103 helix/turn motif scale applied to positions 6 and 7 of the peptide,
pp. QIAN880137 helix/turn motif scale applied to positions 6 and 7 of the peptide,
qq. QIAN880101 helix/turn motif scale applied to positions 7 and 8 of the peptide,
rr. QIAN880102 helix/turn motif scale applied to positions 8 and 9 of the peptide,
ss. NAKH920101 helix/turn motif scale applied to positions 8 and 9 of the peptide, tt. RICJ880109 helix/turn motif scale applied to positions 3, 4, 5, 6, 7 and 8,
uu. NAKH920106 helix/turn motif scale applied to positions 1, 2, 3, 4, 5, 6, 7, 8 and 9 of the peptide,
vv. QIAN880107 helix/turn motif scale applied to positions 1, 2, 8 and 9 of the peptide,
ww. ROBB760108 helix/turn motif scale applied to positions 6 and 7 of the peptide,
xx. QIAN880139 helix/turn motif scale applied to positions 2 and 3 of the peptide, and
yy. QIAN880138 helix/turn motif scale applied to positions 7 and 8 of the peptide,
or a combination thereof.

23. The method of claim 1, wherein at step d.ii, the hydrophobic features so matched is applied to any of
a. JOND750102 hydrophobic scale applied to positions 8 and 9 of the peptide,
b. MEEJ800102 hydrophobic scale applied to position 2 of the peptide,
c. CEDJ970101 hydrophobic scale applied to positions 8 and 9 of the peptide,
d. WILM950104 hydrophobic scale applied to positions 2 and 3 of the peptide,
e. WILM950103 hydrophobic scale applied to position 3 of the peptide,
f. WILM950104 hydrophobic scale applied to positions 1, 2, 3, 4, 5, 6, 7, 8 and 9 of the peptide,
g. NAKH900108 hydrophobic scale applied to positions 1, 2, 3, 4, 5, 6, 7, 8 and 9 of the peptide,
h. X Log P.VAR hydrophobic scale applied to positions 1, 2, 3, 4, 5, 6, 7, 8 and 9 of the peptide,
i. KIDA850101 hydrophobic scale applied to positions 2 and 3 of the peptide,
j. RADA880101 hydrophobic scale applied to position 3 of the peptide,
k. RADA880104 hydrophobic scale applied to position 3 of the peptide,
l. WILM950104 hydrophobic scale applied to position 3 of the peptide,
m. BULH740102 hydrophobic scale applied to positions 5 and 6 of the peptide,
n. CIDH920103 hydrophobic scale applied to position 6 of the peptide,
o. RADA880107 hydrophobic scale applied to positions 6 and 7 of the peptide,
p. PONP800103 hydrophobic scale applied to positions 6 and 7 of the peptide,
q. KANM800104 hydrophobic scale applied to positions 1, 2, 8 and 9 of the peptide,
r. ZASB820101 hydrophobic scale applied to positions 1, 2, 3, 4, 5, 6, 7, 8 and 9 of the peptide,
s. WILM950103 hydrophobic scale applied to positions 1, 2, 3, 4, 5, 6, 7, 8 and 9 of the peptide,
t. YUTK870103 hydrophobic scale applied to positions 5 and 6 of the peptide,
u. YUTK870103 hydrophobic scale applied to positions 8 and 9 of the peptide, and
v. YUTK870104 hydrophobic scale applied to positions 8 and 9 of the peptide,
or a combination thereof.

24. The method of claim 1, wherein at step d.ii, the helix/turn motif and the hydrophobic feature so matched is applied to any of:
a. RACS820104 helix/turn motif scale applied to positions 8 and 9 of the peptide,
b. TANS770108 helix/turn motif scale applied to position 3 of the peptide,
c. RICJ880115 helix/turn motif scale applied to positions 4 and 5 of the peptide,
d. RICJ880109 helix/turn motif scale applied to positions 5 and 6 of the peptide,
e. PALI810109 helix/turn motif scale applied to position 6 of the peptide,
f. RICJ880104 helix/turn motif scale applied to positions 2 and 3 of the peptide,
g. QIAN880137 helix/turn motif scale applied to positions 7 and 8 of the peptide,
h. PALI810108 helix/turn motif scale applied to positions 8 and 9 of the peptide,
i. QIAN880127 helix/turn motif scale applied to positions 1, 2, 8 and 9 of the peptide,
j. SUYM030101 helix/turn motif scale applied to positions 3, 4, 5, 6, 7 and 8 of the peptide,
k. RACS820107 helix/turn motif scale applied to positions 1 and 2 of the peptide,
l. ROBB760111 helix/turn motif scale applied to positions 1 and 2 of the peptide,
m. TANS770102 helix/turn motif scale applied to positions 1 and 2 of the peptide,
n. QIAN880139 helix/turn motif scale applied to positions 1 and 2 of the peptide,
o. RICJ880113 helix/turn motif scale applied to positions 2 and 3 of the peptide,
p. RICJ880105 helix/turn motif scale applied to positions 5 and 6 of the peptide,
q. CHOP780204 helix/turn motif scale applied to position 6 of the peptide,
r. PALI810108 helix/turn motif scale applied to positions 6 and 7 of the peptide,
s. PALI810113 helix/turn motif scale applied to positions 6 and 7 of the peptide,
t. RACS820107 helix/turn motif scale applied to positions 3, 4, 5, 6, 7 and 8 of the peptide,
u. RICJ880110 helix/turn motif scale applied to positions 3, 4, 5, 6, 7 and 8 of the peptide,
v. SUYM030101 helix/turn motif scale applied to positions 1, 2, 3, 4, 5, 6, 7, 8 and 9 of the peptide,
w. SUEM840102 helix/turn motif scale applied to position 1 of the peptide,
x. PALI810108 helix/turn motif scale applied to positions 1 and 2 of the peptide,
y. LEVM780104 helix/turn motif scale applied to positions 1 and 2 of the peptide,
z. RICJ880104 helix/turn motif scale applied to positions 1 and 2 of the peptide,
aa. GEIM800109 helix/turn motif scale applied to position 2 of the peptide,
bb. ROBB760111 helix/turn motif scale applied to position 2 of the peptide,
cc. QIAN880112 helix/turn motif scale applied to position 2 of the peptide,
dd. CHOP780212 helix/turn motif scale applied to positions 2 and 3 of the peptide,
ee. BUNA790101 helix/turn motif scale applied to positions 2 and 3 of the peptide,
ff. RICJ880114 helix/turn motif scale applied to positions 2 and 3 of the peptide,
gg. RACS820103 helix/turn motif scale applied to position 3 of the peptide,
hh. RICJ880109 helix/turn motif scale applied to positions 3 and 4 of the peptide,
ii. RICJ880113 helix/turn motif scale applied to positions 4 and 5 of the peptide, jj. RACS820105 helix/turn motif scale applied to positions 5 and 6 of the peptide,
kk. CHOP780213 helix/turn motif scale applied to position 6 of the peptide,
ll. RACS820106 helix/turn motif scale applied to position 6 of the peptide,
mm. PALI810107 helix/turn motif scale applied to position 6 of the peptide,
nn. QIAN880106 helix/turn motif scale applied to position 6 of the peptide,
oo. MAXF760103 helix/turn motif scale applied to positions 6 and 7 of the peptide,
pp. QIAN880137 helix/turn motif scale applied to positions 6 and 7 of the peptide,
qq. QIAN880101 helix/turn motif scale applied to positions 7 and 8 of the peptide,
rr. QIAN880102 helix/turn motif scale applied to positions 8 and 9 of the peptide,
ss. NAKH920101 helix/turn motif scale applied to positions 8 and 9 of the peptide,
tt. RICJ880109 helix/turn motif scale applied to positions 3, 4, 5, 6, 7 and 8 of the peptide,
uu. NAKH920106 helix/turn motif scale applied to positions 1, 2, 3, 4, 5, 6, 7, 8 and 9 of the peptide,
vv. QIAN880107 helix/turn motif scale applied to positions 1, 2, 8 and 9 of the peptide,
ww. ROBB760108 helix/turn motif scale applied to positions 6 and 7 of the peptide,
xx. QIAN880139 helix/turn motif scale applied to positions 2 and 3 of the peptide,
yy. QIAN880138 helix/turn motif scale applied to positions 7 and 8 of the peptide,
zz. JOND750102 hydrophobic scale applied to positions 8 and 9 of the peptide,
aaa. MEEJ800102 hydrophobic scale applied to position 2 of the peptide,
bbb. CEDJ970101 hydrophobic scale applied to positions 8 and 9 of the peptide,
ccc. WILM950104 hydrophobic scale applied to positions 2 and 3 of the peptide,
ddd. WILM950103 hydrophobic scale applied to position 3 of the peptide,
eee. WILM950104 hydrophobic scale applied to positions 1, 2, 3, 4, 5, 6, 7, 8 and 9 of the peptide,
fff. NAKH900108 hydrophobic scale applied to positions 1, 2, 3, 4, 5, 6, 7, 8 and 9 of the peptide,
ggg. X Log P.VAR hydrophobic scale applied to positions 1, 2, 3, 4, 5, 6, 7, 8 and 9 of the peptide,
hhh. KIDA850101 hydrophobic scale applied to positions 2 and 3 of the peptide,
iii. RADA880101 hydrophobic scale applied to position 3 of the peptide,
jjj. RADA880104 hydrophobic scale applied to position 3 of the peptide,
jjj. WILM950104 hydrophobic scale applied to position 3 of the peptide,
kkk. BULH740102 hydrophobic scale applied to positions 5 and 6 of the peptide,
lll. CIDH920103 hydrophobic scale applied to position 6 of the peptide,
mmm. RADA880107 hydrophobic scale applied to positions 6 and 7 of the peptide,
nnn. PONP800103 hydrophobic scale applied to positions 6 and 7 of the peptide,
ooo. KANM800104 hydrophobic scale applied to positions 1, 2, 8 and 9 of the peptide,
ppp. ZASB820101 hydrophobic scale applied to positions 1, 2, 3, 4, 5, 6, 7, 8 and 9 of the peptide,
qqq. WILM950103 hydrophobic scale applied to positions 1, 2, 3, 4, 5, 6, 7, 8 and 9 of the peptide,
rrr. YUTK870103 hydrophobic scale applied to positions 5 and 6 of the peptide,
sss. YUTK870103 hydrophobic scale applied to positions 8 and 9 of the peptide, and
ttt. YUTK870104 hydrophobic scale applied to positions 8 and 9 of the peptide,
or a combination thereof.

* * * * *

SEQUENCE LISTING

```
<160> NUMBER OF SEQ ID NOS: 519

<210> SEQ ID NO 1
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 1

Leu Gln Val Asp Gln Leu Trp Asp Val
1               5

<210> SEQ ID NO 2
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
``` ability to interact with the TCR and may or can serve as a
mammalian tumor vaccine

<400> SEQUENCE: 2

Arg Thr Phe Cys Leu Leu Val Val Val
1               5

<210> SEQ ID NO 3
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: QLREASPWV

<400> SEQUENCE: 3

Gln Leu Arg Glu Ala Ser Pro Trp Val
1               5

<210> SEQ ID NO 4
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 4

Cys Leu Leu Val Val Val Val Val Val
1               5

<210> SEQ ID NO 5
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 5

Phe Cys Leu Leu Val Val Val Val Val
1               5

<210> SEQ ID NO 6
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 6

Pro Ile Tyr Met Tyr Ser Thr Met Val
1               5

<210> SEQ ID NO 7
<211> LENGTH: 9
<212> TYPE: PRT
<213> ORGANISM: Homo sapiens

```
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 7

Leu Val Val Val Val Val Val Phe Ala
1               5

<210> SEQ ID NO 8
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 8

Thr Ala Phe Trp Arg Ser Leu Leu Ala
1               5

<210> SEQ ID NO 9
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 9

Gln Leu Trp Asp Val Leu Leu Ser Arg
1               5

<210> SEQ ID NO 10
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 10

Val Gln Arg Leu Pro Phe Ser Thr Val
1               5

<210> SEQ ID NO 11
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 11

Pro Gln Leu Arg Arg Trp Leu Leu Val
1               5
```

```
<210> SEQ ID NO 12
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 12

Leu Leu Val Val Val Val Val Val Phe
1               5

<210> SEQ ID NO 13
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 13

Thr Phe Cys Leu Leu Val Val Val Val
1               5

<210> SEQ ID NO 14
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 14

Gly Gln Ala Thr Pro Leu Pro Val Thr
1               5

<210> SEQ ID NO 15
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 15

Thr Met Arg Pro Leu Pro Gly Arg Ile
1               5

<210> SEQ ID NO 16
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
``` mammalian tumor vaccine

<400> SEQUENCE: 16

Val Leu Leu Ser Arg Glu Leu Phe Arg
1               5

<210> SEQ ID NO 17
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 17

Gln Ala Thr Pro Leu Pro Val Thr Ile
1               5

<210> SEQ ID NO 18
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 18

Ile Tyr Met Tyr Ser Thr Met Val Phe
1               5

<210> SEQ ID NO 19
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 19

Ser Asp Ala Tyr Pro Ser Ala Phe Pro
1               5

<210> SEQ ID NO 20
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 20

Arg Gln Gly Arg Gln Arg Arg Val Arg
1               5

<210> SEQ ID NO 21
<211> LENGTH: 9
<212> TYPE: PRT

```
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 21

Leu Leu Arg Gln Gly Arg Gln Arg Arg
1               5

<210> SEQ ID NO 22
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 22

Val Gly Gln Arg Ile Gly Ser Val Ser
1               5

<210> SEQ ID NO 23
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 23

Val Gly Arg Ser Val Ala Ile Gly Pro
1               5

<210> SEQ ID NO 24
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 24

Glu Leu His Ser Leu Trp Thr Cys Asp
1               5

<210> SEQ ID NO 25
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 25

Ser Pro Trp Val Arg Pro Arg Arg Arg
```

<210> SEQ ID NO 26
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 26

Pro Leu Pro Gly Arg Ile Glu Val Arg
1               5

<210> SEQ ID NO 27
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 27

Thr Pro Glu Val Gln Gly Arg Val Pro
1               5

<210> SEQ ID NO 28
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 28

Pro Trp Val Arg Pro Arg Arg Arg Leu
1               5

<210> SEQ ID NO 29
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 29

Val Val Val Val Val Val Phe Ala Val
1               5

<210> SEQ ID NO 30
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted

```
        ability to interact with the TCR and may or can serve as a
        mammalian tumor vaccine

<400> SEQUENCE: 30

Trp Leu Leu Val Ser Ser Pro Pro Ser
1               5

<210> SEQ ID NO 31
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
        ability to interact with the TCR and may or can serve as a
        mammalian tumor vaccine

<400> SEQUENCE: 31

Leu Val Val Gly Arg Ser Val Ala Ile
1               5

<210> SEQ ID NO 32
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
        ability to interact with the TCR and may or can serve as a
        mammalian tumor vaccine

<400> SEQUENCE: 32

Arg Ile Gly Ser Val Ser Phe Gly Thr
1               5

<210> SEQ ID NO 33
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
        ability to interact with the TCR and may or can serve as a
        mammalian tumor vaccine

<400> SEQUENCE: 33

Arg Ala Asp Leu Ile Arg Leu Leu Leu
1               5

<210> SEQ ID NO 34
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
        ability to interact with the TCR and may or can serve as a
        mammalian tumor vaccine

<400> SEQUENCE: 34

Thr Val Gly Gln Arg Ile Gly Ser Val
1               5

<210> SEQ ID NO 35
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 35

Arg Thr Pro Glu Val Gln Gly Arg Val
1               5

<210> SEQ ID NO 36
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 36

Arg Ser Leu Leu Ala Cys Cys Gln Leu
1               5

<210> SEQ ID NO 37
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 37

Tyr Pro Val Gln Arg Leu Pro Phe Ser
1               5

<210> SEQ ID NO 38
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 38

Arg Trp Leu Leu Val Ser Ser Pro Pro
1               5

<210> SEQ ID NO 39
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 39
```

```
Phe Trp Arg Ser Leu Leu Ala Cys Cys
1               5

<210> SEQ ID NO 40
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 40

Val Val Val Val Phe Ala Val Cys Trp
1               5

<210> SEQ ID NO 41
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 41

Thr Cys Asn Ser Arg Gln Ala Ala Leu
1               5

<210> SEQ ID NO 42
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 42

Pro Val Gln Arg Leu Pro Phe Ser Thr
1               5

<210> SEQ ID NO 43
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 43

Ala Leu Ser Arg Pro Gly Leu Leu Arg
1               5

<210> SEQ ID NO 44
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<223> OTHER INFORMATION: selected peptide variant with a predicted
      ability to interact with the TCR and may or can serve as a
      mammalian tumor vaccine

<400> SEQUENCE: 44

Glu Pro Ile Tyr Met Tyr Ser Thr Met
1               5

<210> SEQ ID NO 45
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 45

Val Val Gly Arg Ser Val Ala Ile Gly
1               5

<210> SEQ ID NO 46
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 46

His Gly Arg Ala Asp Leu Ile Arg Leu
1               5

<210> SEQ ID NO 47
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 47

Ser Gly Val Gly Lys Ser Ala Leu Thr
1               5

<210> SEQ ID NO 48
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 48

Arg Tyr Pro Val Gln Arg Leu Pro Phe
1               5

<210> SEQ ID NO 49
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 49

Asp Leu Ile Arg Leu Leu Leu Lys His
1               5

<210> SEQ ID NO 50
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 50

Ala Asp Leu Ile Arg Leu Leu Leu Lys
1               5

<210> SEQ ID NO 51
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 51

Leu His Ser Leu Trp Thr Cys Asp Cys
1               5

<210> SEQ ID NO 52
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 52

Val Ala Ile Gly Pro Arg Glu Gln Trp
1               5

<210> SEQ ID NO 53
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 53
```

```
Leu Ile Arg Leu Leu Leu Lys His Gly
1               5

<210> SEQ ID NO 54
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 54

Ser Ala Thr Val Thr Ala Phe Trp Arg
1               5

<210> SEQ ID NO 55
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 55

Gly Ser Val Ser Phe Gly Thr Val Tyr
1               5

<210> SEQ ID NO 56
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 56

Val Gln Gly Arg Val Pro Thr Leu Glu
1               5

<210> SEQ ID NO 57
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 57

Pro Gln Ala Arg Ala Val His Leu Pro
1               5

<210> SEQ ID NO 58
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 58

Leu Ser Arg Pro Gly Leu Leu Arg Gln
1               5

<210> SEQ ID NO 59
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 59

Leu Arg Glu Ala Ser Pro Trp Val Arg
1               5

<210> SEQ ID NO 60
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 60

Arg Pro Glu Val Arg Lys Thr Ala Ser
1               5

<210> SEQ ID NO 61
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 61

Leu His Gly Arg Ala Asp Leu Ile Arg
1               5

<210> SEQ ID NO 62
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 62

Gln Gly Arg Val Pro Thr Leu Glu Arg
1               5
```

```
<210> SEQ ID NO 63
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 63

His Asp Pro Gln Ala Arg Ala Val His
1               5

<210> SEQ ID NO 64
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 64

Pro Gly Leu Leu Arg Gln Gly Arg Gln
1               5

<210> SEQ ID NO 65
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 65

Ile Gly Ser Val Ser Phe Gly Thr Val
1               5

<210> SEQ ID NO 66
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 66

Val Val Val Val Val Phe Ala Val Cys
1               5

<210> SEQ ID NO 67
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine
```

```
<400> SEQUENCE: 67

Val His Leu Pro Glu Leu Leu Ser Leu
1               5

<210> SEQ ID NO 68
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 68

Gln Leu Arg Arg Trp Leu Leu Val Ser
1               5

<210> SEQ ID NO 69
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 69

Gly Gln Arg Ile Gly Ser Val Ser Phe
1               5

<210> SEQ ID NO 70
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 70

Gly Glu Leu His Ser Leu Trp Thr Cys
1               5

<210> SEQ ID NO 71
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 71

Arg Thr Met Arg Pro Leu Pro Gly Arg
1               5

<210> SEQ ID NO 72
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 72

Met Tyr Ser Thr Met Val Phe Leu Pro
1               5

<210> SEQ ID NO 73
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 73

Thr Gly Gln Ala Thr Pro Leu Pro Val
1               5

<210> SEQ ID NO 74
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 74

Ala Phe Trp Arg Ser Leu Leu Ala Cys
1               5

<210> SEQ ID NO 75
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 75

Tyr Ser Thr Met Val Phe Leu Pro Trp
1               5

<210> SEQ ID NO 76
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 76

Val Asp Gln Leu Trp Asp Val Leu Leu
1               5
```

```
<210> SEQ ID NO 77
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 77

Arg Pro Gln Leu Arg Arg Trp Leu Leu
1               5

<210> SEQ ID NO 78
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 78

Leu Gln Leu Arg Glu Ala Ser Pro Trp
1               5

<210> SEQ ID NO 79
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 79

His Ser Leu Trp Thr Cys Asp Cys Glu
1               5

<210> SEQ ID NO 80
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 80

Leu Pro Gly Arg Ile Glu Val Arg Thr
1               5

<210> SEQ ID NO 81
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine
```

```
<400> SEQUENCE: 81

Leu Trp Asp Val Leu Leu Ser Arg Glu
1               5

<210> SEQ ID NO 82
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 82

Glu Val Gln Gly Arg Val Pro Thr Leu
1               5

<210> SEQ ID NO 83
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 83

Ala Thr Val Thr Ala Phe Trp Arg Ser
1               5

<210> SEQ ID NO 84
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 84

Gln Val Asp Gln Leu Trp Asp Val Leu
1               5

<210> SEQ ID NO 85
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 85

Ala Ser Asp Ala Tyr Pro Ser Ala Phe
1               5

<210> SEQ ID NO 86
<211> LENGTH: 9
<212> TYPE: PRT
<213> ORGANISM: Homo sapiens
```

-continued

```
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 86

Asp Gly Leu Val Val Gly Arg Ser Val
1               5

<210> SEQ ID NO 87
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 87

Ser Gly Glu Leu His Ser Leu Trp Thr
1               5

<210> SEQ ID NO 88
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 88

Asp Gln Leu Trp Asp Val Leu Leu Ser
1               5

<210> SEQ ID NO 89
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: selected peptide variant with a predicted
      ability to interact with the TCR and may or can serve as a
      mammalian tumor vaccine

<400> SEQUENCE: 89

Phe Gln Asp His Lys Pro Lys Ile Ser
1               5

<210> SEQ ID NO 90
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 90

Trp Leu Leu Ile Asp Thr Ser Asn Ala
1               5
```

-continued

<210> SEQ ID NO 91
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 91

Arg Val Ser Arg Pro Thr Thr Val Val
1               5

<210> SEQ ID NO 92
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 92

Tyr Leu Asp Leu Ala Leu Met Ser Val
1               5

<210> SEQ ID NO 93
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 93

Phe Ile Phe Leu Leu Phe Leu Thr Leu
1               5

<210> SEQ ID NO 94
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 94

Asp Glu Thr Gly Val Glu Val Lys Asp
1               5

<210> SEQ ID NO 95
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 95

Leu Met Leu Pro Gly Met Asn Gly Ile
1               5

```
<210> SEQ ID NO 96
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: EMKEGRYEV

<400> SEQUENCE: 96

Glu Met Lys Glu Gly Arg Tyr Glu Val
1               5

<210> SEQ ID NO 97
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 97

Val Leu Leu Glu Lys Ala Thr Ile Leu
1               5

<210> SEQ ID NO 98
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 98

Ser Leu Leu Glu Arg Gly Gln Gln Leu
1               5

<210> SEQ ID NO 99
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 99

Tyr Leu Ser Glu Gly Asp Met Ala Ala
1               5

<210> SEQ ID NO 100
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 100

Arg Val Tyr Glu Ala Leu Tyr Tyr Val
1               5
```

<210> SEQ ID NO 101
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 101

Lys Leu Gly Leu Leu Gln Val Thr Gly
1               5

<210> SEQ ID NO 102
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 102

Ser Met Ala Gly Asn Trp Ala Lys Val
1               5

<210> SEQ ID NO 103
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 103

Val Val Trp Val Lys Ile Thr Gln Val
1               5

<210> SEQ ID NO 104
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 104

Gly Leu Tyr Arg Gln Trp Ala Leu Ala
1               5

<210> SEQ ID NO 105
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 105

Ser Met Gly Ile Phe Leu Lys Ser Leu

```
<210> SEQ ID NO 106
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 106

Ser Leu Phe Pro Glu Phe Ser Glu Leu
1               5

<210> SEQ ID NO 107
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 107

Gly Glu Ser Val Pro Gly Ile Glu Glu
1               5

<210> SEQ ID NO 108
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 108

Tyr Leu Tyr Val His Ser Pro Ala Leu
1               5

<210> SEQ ID NO 109
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 109

Phe Met Lys Ala Val Cys Val Glu Val
1               5

<210> SEQ ID NO 110
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 110
```

```
Asp Ser Thr Gln Thr Thr Thr Gln Lys
1               5

<210> SEQ ID NO 111
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 111

Tyr Ser Leu Glu Tyr Phe Gln Phe Val
1               5

<210> SEQ ID NO 112
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 112

Arg Ala Lys Ala Val Arg Ala Leu Lys
1               5

<210> SEQ ID NO 113
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 113

Thr Glu Gln Glu Leu Pro Gln Ser Gln
1               5

<210> SEQ ID NO 114
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 114

Ser Leu Ala Gly Phe Val Arg Met Leu
1               5

<210> SEQ ID NO 115
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 115
```

```
Gly Leu Phe Leu Thr Thr Glu Ala Val
1               5

<210> SEQ ID NO 116
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 116

Arg Leu Gln Ser Leu Gln Thr Tyr Val
1               5

<210> SEQ ID NO 117
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 117

Leu Leu Pro Leu Gly Tyr Pro Phe Val
1               5

<210> SEQ ID NO 118
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 118

Ala Leu Leu Arg Gln Leu Ala Glu Leu
1               5

<210> SEQ ID NO 119
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 119

Phe Val Val Ala Leu Ile Pro Leu Val
1               5

<210> SEQ ID NO 120
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm
```

```
<400> SEQUENCE: 120

Ser Leu Gln Asn Ser Glu Phe Leu Leu
1               5

<210> SEQ ID NO 121
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 121

Ala Tyr Gly Ser Phe Val Arg Thr Val
1               5

<210> SEQ ID NO 122
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 122

Gly Leu Met Thr Ala Val Tyr Leu Val
1               5

<210> SEQ ID NO 123
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 123

Leu Met His Ala Pro Ala Phe Glu Thr
1               5

<210> SEQ ID NO 124
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 124

Gly Leu Tyr Tyr Leu Thr Thr Glu Val
1               5

<210> SEQ ID NO 125
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm
```

<400> SEQUENCE: 125

Leu Leu Tyr Asn Glu Gln Phe Ala Val
1               5

<210> SEQ ID NO 126
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 126

Val Val Phe Glu Asp Val Lys Gly Thr
1               5

<210> SEQ ID NO 127
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 127

Ala Leu Ser Thr Gly Leu Ile His Leu
1               5

<210> SEQ ID NO 128
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 128

Phe Ile Pro Glu Asn Gln Arg Thr Val
1               5

<210> SEQ ID NO 129
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 129

Asp Leu Pro Ser Gly Phe Asn Thr Leu
1               5

<210> SEQ ID NO 130
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the -continued

```
                TCR-binding algorithm

<400> SEQUENCE: 130

Gly Leu Phe Gly Lys Gly Ser Leu Val
1               5

<210> SEQ ID NO 131
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 131

Asn Ser Asn Asp Ile Val Asn Ala Ile
1               5

<210> SEQ ID NO 132
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 132

Thr Val Leu Arg Phe Val Pro Pro Leu
1               5

<210> SEQ ID NO 133
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 133

Ser Leu Leu Glu Ile Gly Glu Gly Val
1               5

<210> SEQ ID NO 134
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 134

Val Ile Ala Asp Tyr Asn Tyr Lys Leu
1               5

<210> SEQ ID NO 135
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<223> OTHER INFORMATION: Non-immunogenic peptide used for developing the
      TCR-binding algorithm

<400> SEQUENCE: 135

Ala Ile Met Asp Lys Thr Val Ile Leu
1               5

<210> SEQ ID NO 136
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 136

Lys Val Leu Thr Leu Phe Ala Glu Val
1               5

<210> SEQ ID NO 137
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 137

Ser Arg Ala Lys Ala Val Arg Ala Leu
1               5

<210> SEQ ID NO 138
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 138

Lys Leu Asp Lys Glu Met Glu Ala Val
1               5

<210> SEQ ID NO 139
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 139

Val Leu Ala Asp Ala Asn Glu Thr Leu
1               5

<210> SEQ ID NO 140
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)
<223> OTHER INFORMATION: Non-immunogenic peptide used for developing the
      TCR-binding algorithm

<400> SEQUENCE: 140

Met Leu Gly Asn Ala Pro Ser Val Val
1               5

<210> SEQ ID NO 141
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 141

Leu Leu Trp Gln Asp Pro Val Pro Ala
1               5

<210> SEQ ID NO 142
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 142

Arg Leu Leu Glu Ala Phe Gln Phe Val
1               5

<210> SEQ ID NO 143
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 143

Leu Leu Pro Pro Glu Leu Ser Glu Thr
1               5

<210> SEQ ID NO 144
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 144

Gly Leu Val Asp Phe Val Lys His Ile
1               5

<210> SEQ ID NO 145
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 145

Val Leu Leu Glu Gln Met Gly Ser Leu
1               5

<210> SEQ ID NO 146
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 146

Met Leu Ala Asp Lys Thr Lys Ser Ile
1               5

<210> SEQ ID NO 147
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 147

Leu Val Leu Glu Gln Leu Gly Gln Leu
1               5

<210> SEQ ID NO 148
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 148

Arg Met Pro Ala Val Thr Asp Leu Val
1               5

<210> SEQ ID NO 149
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 149

Thr Arg Val Thr Ile Trp Lys Ser Lys
1               5

<210> SEQ ID NO 150
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 150

Tyr Leu Ser Gln Ile Ala Val Leu Leu
1               5

<210> SEQ ID NO 151
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 151

Tyr Leu Leu Ala Leu Arg Tyr Leu Ala
1               5

<210> SEQ ID NO 152
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 152

Arg Leu Met Ile Gly Thr Ala Ala Ala
1               5

<210> SEQ ID NO 153
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 153

Phe Leu Leu Pro Asp Ala Gln Ser Ile
1               5

<210> SEQ ID NO 154
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 154

Tyr Thr Tyr Lys Trp Glu Thr Phe Leu
1               5

<210> SEQ ID NO 155
<211> LENGTH: 9
<212> TYPE: PRT
```

```
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 155

Ala Glu Thr Gly Ser Gly Thr Ala Ser
1               5

<210> SEQ ID NO 156
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 156

Lys Leu Cys Thr Phe Ser Phe Leu Ile
1               5

<210> SEQ ID NO 157
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 157

Phe Leu Ile His Ser Ala Asp Trp Leu
1               5

<210> SEQ ID NO 158
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 158

Ala Leu Trp Gly Pro Asp Pro Ala Ala
1               5

<210> SEQ ID NO 159
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 159

Asn Ile Leu Phe Val Ile Thr Lys Leu
1               5

<210> SEQ ID NO 160
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 160

Leu Leu Ala Cys Ala Val Ile His Ala
1               5

<210> SEQ ID NO 161
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 161

Thr Leu Ala Ala Arg Ile Lys Phe Leu
1               5

<210> SEQ ID NO 162
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 162

Asp Val Val Asn Gly Leu Ala Asn Leu
1               5

<210> SEQ ID NO 163
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 163

Ala Leu Ala Pro Ala Pro Val Glu Val
1               5

<210> SEQ ID NO 164
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 164

Tyr Leu Gly Lys Leu Phe Val Thr Leu
1               5

<210> SEQ ID NO 165
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 165

Gly Ala Asp Glu Asp Asp Ile Lys Ala
1               5

<210> SEQ ID NO 166
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 166

Lys Leu Leu Thr Lys Pro Trp Asp Val
1               5

<210> SEQ ID NO 167
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 167

Trp Met His His Asn Met Asp Leu Val
1               5

<210> SEQ ID NO 168
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 168

Gly Leu Tyr Leu Ser Gln Ile Ala Val
1               5

<210> SEQ ID NO 169
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 169

Ile Leu Phe Thr Phe Leu His Leu Ala
1               5
```

```
<210> SEQ ID NO 170
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 170

Thr Glu Val Gly Gln Asp Gln Tyr Val
1               5

<210> SEQ ID NO 171
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 171

Thr Arg His Pro Ala Thr Ala Thr Val
1               5

<210> SEQ ID NO 172
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 172

Leu Leu Phe Leu Gly Val Val Phe Leu
1               5

<210> SEQ ID NO 173
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 173

Ile Leu Ser Ser Leu Gly Leu Pro Val
1               5

<210> SEQ ID NO 174
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 174

Phe Ala Asn Tyr Asn Phe Thr Leu Leu
1               5
```

```
<210> SEQ ID NO 175
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 175

Ile Leu Leu Ser Ile Ala Arg Val Val
1               5

<210> SEQ ID NO 176
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 176

Ile Val Tyr Glu Ala Ala Asp Ala Ile
1               5

<210> SEQ ID NO 177
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 177

Lys Phe Arg Val Gln Gly Glu Ala Val
1               5

<210> SEQ ID NO 178
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 178

Arg Leu Leu Asp Asp Thr Pro Glu Val
1               5

<210> SEQ ID NO 179
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 179

Lys Ile Phe Cys Ile Ser Ile Phe Leu
1               5
```

```
<210> SEQ ID NO 180
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 180

Ala Met Leu Gln Asp Met Ala Ile Leu
1               5

<210> SEQ ID NO 181
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 181

Ala Leu Val Leu Leu Met Leu Pro Val
1               5

<210> SEQ ID NO 182
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 182

Met Ile Ala Ala Tyr Thr Ala Ala Leu
1               5

<210> SEQ ID NO 183
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 183

Ala Ala Leu Gly Leu Trp Leu Ser Val
1               5

<210> SEQ ID NO 184
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 184

Val Leu Cys Pro Tyr Met Pro Lys Val
```

<210> SEQ ID NO 185
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 185

Ala Leu Ile Ile Ile Arg Ser Leu Leu
1               5

<210> SEQ ID NO 186
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 186

Val Leu Leu Leu Asp Val Thr Pro Leu
1               5

<210> SEQ ID NO 187
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 187

Ala Ile Tyr His Pro Gln Gln Phe Val
1               5

<210> SEQ ID NO 188
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 188

Ala Met Lys Ala Asp Ile Gln His Val
1               5

<210> SEQ ID NO 189
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 189

```
Ala Leu Leu Ser Asp Trp Leu Pro Ala
1               5

<210> SEQ ID NO 190
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 190

Arg Met Phe Ala Ala Asn Leu Gly Val
1               5

<210> SEQ ID NO 191
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 191

Met Leu Gln Asp Met Ala Ile Leu Thr
1               5

<210> SEQ ID NO 192
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 192

Ala Leu Leu Trp Ala Ala Gly Val Leu
1               5

<210> SEQ ID NO 193
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 193

Leu Leu Phe Arg Phe Met Arg Pro Leu
1               5

<210> SEQ ID NO 194
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 194
```

Arg Leu Gly Ala Val Ile Leu Phe Val
1               5

<210> SEQ ID NO 195
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 195

Asp Leu Ser Arg Asp Leu Asp Ser Val
1               5

<210> SEQ ID NO 196
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 196

Gly Leu Tyr Gly Ala Gln Tyr Asp Val
1               5

<210> SEQ ID NO 197
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 197

Phe Leu Ala Val Gly Gly Val Leu Leu
1               5

<210> SEQ ID NO 198
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 198

Met Leu Ala Ser Thr Leu Thr Asp Ala
1               5

<210> SEQ ID NO 199
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

```
<400> SEQUENCE: 199

Tyr Leu Val Thr Ser Ile Asn Lys Leu
1               5

<210> SEQ ID NO 200
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 200

Ser Leu Pro Lys His Asn Val Thr Ile
1               5

<210> SEQ ID NO 201
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 201

Arg Leu Ala Arg Ala Ile Ile Glu Leu
1               5

<210> SEQ ID NO 202
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 202

Met Ala Leu Leu Arg Leu Pro Leu Val
1               5

<210> SEQ ID NO 203
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 203

Tyr Lys Ser Pro Ala Ser Asp Ala Tyr
1               5

<210> SEQ ID NO 204
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm
```

```
<400> SEQUENCE: 204

Lys Leu Ser Ser Phe Phe Gln Ser Val
1               5

<210> SEQ ID NO 205
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Non-immunogenic peptide used for developing the
      TCR-binding algorithm

<400> SEQUENCE: 205

Ala Ile Met Asp Lys Lys Ile Ile Leu
1               5

<210> SEQ ID NO 206
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 206

Ser Leu Lys Asp Val Leu Val Ser Val
1               5

<210> SEQ ID NO 207
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 207

Val Ala Ala Leu Phe Phe Phe Asp Ile
1               5

<210> SEQ ID NO 208
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 208

Ser Leu Trp Gly Gly Asp Val Val Leu
1               5

<210> SEQ ID NO 209
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
```

```
                          TCR-binding algorithm

<400> SEQUENCE: 209

Ala Met Asp Thr Ile Ser Val Phe Leu
1               5

<210> SEQ ID NO 210
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 210

Val Leu Leu Leu Trp Ile Thr Ala Ala
1               5

<210> SEQ ID NO 211
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 211

Met Leu Trp Tyr Thr Val Tyr Asn Ile
1               5

<210> SEQ ID NO 212
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 212

Arg Val Pro Gly Val Ala Pro Thr Leu
1               5

<210> SEQ ID NO 213
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 213

Trp Leu Asp Glu Val Lys Gln Ala Leu
1               5

<210> SEQ ID NO 214
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

<223> OTHER INFORMATION: Immunogenic peptide used for developing the
      TCR-binding algorithm

<400> SEQUENCE: 214

Ala Leu Asn Thr Pro Lys Asp His Ile
1               5

<210> SEQ ID NO 215
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 215

Ala Trp Leu Val Ala Ala Ala Glu Ile
1               5

<210> SEQ ID NO 216
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 216

Ala Ile Leu His Thr Pro Gly Cys Val
1               5

<210> SEQ ID NO 217
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 217

Gly Leu Leu Asp Gln Val Ala Ala Leu
1               5

<210> SEQ ID NO 218
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 218

Ser Gln Gln Ala Gln Leu Ala Ala Ala
1               5

<210> SEQ ID NO 219
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)
<223> OTHER INFORMATION: Immunogenic peptide used for developing the
      TCR-binding algorithm

<400> SEQUENCE: 219

Thr Leu Lys Asp Ile Val Leu Asp Leu
1               5

<210> SEQ ID NO 220
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 220

Met Leu Asn Ile Pro Ser Ile Asn Val
1               5

<210> SEQ ID NO 221
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 221

Ala Ile Met Asp Lys Val Ile Ile Leu
1               5

<210> SEQ ID NO 222
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 222

Gly Ile Leu Gly Phe Val Tyr Thr Leu
1               5

<210> SEQ ID NO 223
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 223

Thr Leu Glu Glu Phe Ser Ala Lys Leu
1               5

<210> SEQ ID NO 224
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 224

Leu Leu Asp Ala His Ile Pro Gln Leu
1               5

<210> SEQ ID NO 225
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 225

Arg Thr Leu Asp Lys Val Leu Glu Val
1               5

<210> SEQ ID NO 226
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 226

Tyr Leu Glu Ser Phe Cys Glu Asp Val
1               5

<210> SEQ ID NO 227
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 227

Arg Met Thr Glu Asn Ile Val Glu Val
1               5

<210> SEQ ID NO 228
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 228

Gly Ile Leu Gly Val Val Phe Thr Leu
1               5

<210> SEQ ID NO 229
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 229

Arg Gly Thr Pro Met Val Ile Thr Val
1               5

<210> SEQ ID NO 230
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 230

His Leu Gly Asn Val Lys Tyr Leu Val
1               5

<210> SEQ ID NO 231
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 231

Val Val Pro Glu Asp Tyr Trp Gly Val
1               5

<210> SEQ ID NO 232
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 232

Val Leu Asn Asp Ile Leu Ser Arg Leu
1               5

<210> SEQ ID NO 233
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 233

Arg Leu Pro Leu Val Leu Pro Ala Val
1               5

<210> SEQ ID NO 234
<211> LENGTH: 9
<212> TYPE: PRT
```

```
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 234

Val Leu Asn Glu Thr Thr Asn Trp Leu
1               5

<210> SEQ ID NO 235
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 235

Ala Leu Ser Glu Asp Leu Leu Ser Ile
1               5

<210> SEQ ID NO 236
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 236

Gly Ile Leu Gly Phe Ile Phe Thr Leu
1               5

<210> SEQ ID NO 237
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 237

Ile Met Val Leu Ser Phe Leu Phe Leu
1               5

<210> SEQ ID NO 238
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 238

Thr Leu Ala Pro Gln Val Glu Pro Leu
1               5

<210> SEQ ID NO 239
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 239

Phe Thr Trp Glu Gly Leu Tyr Asn Val
1               5

<210> SEQ ID NO 240
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 240

Ala Ile Met Asp Lys Thr Ile Ile Leu
1               5

<210> SEQ ID NO 241
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 241

Gly Val Leu Gly Phe Val Phe Thr Leu
1               5

<210> SEQ ID NO 242
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 242

Arg Leu Gln Gly Ile Ser Pro Lys Ile
1               5

<210> SEQ ID NO 243
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 243

Ala Leu Leu Lys Asp Thr Val Tyr Thr
1               5

<210> SEQ ID NO 244
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 244

Leu Leu Leu Ile Trp Phe Arg Pro Val
1               5

<210> SEQ ID NO 245
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 245

Val Ala Ala Asn Ile Val Leu Thr Val
1               5

<210> SEQ ID NO 246
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 246

Ala Met Leu His Trp Ser Leu Ile Leu
1               5

<210> SEQ ID NO 247
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 247

Ala Leu Ala Val Leu Ser Val Thr Leu
1               5

<210> SEQ ID NO 248
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 248

Ser Gly Asp Gly Leu Val Ala Thr Gly
1               5
```

```
<210> SEQ ID NO 249
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 249

Gly Leu Ser Ile Ser Gly Asn Leu Leu
1               5

<210> SEQ ID NO 250
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 250

Tyr Leu Leu Pro Ala Ile Val His Ile
1               5

<210> SEQ ID NO 251
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 251

Trp Ile Leu Gly Phe Val Phe Thr Leu
1               5

<210> SEQ ID NO 252
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 252

Ser Leu Ser Ala Tyr Ile Ile Arg Val
1               5

<210> SEQ ID NO 253
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 253

Lys Leu Val Cys Ser Pro Ala Pro Cys
1               5
```

```
<210> SEQ ID NO 254
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 254

Tyr Ile Asn Thr Ala Leu Leu Asn Ala
1               5

<210> SEQ ID NO 255
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 255

Ile Leu Leu Ala Arg Leu Phe Leu Tyr
1               5

<210> SEQ ID NO 256
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 256

Tyr Leu Asp Lys Val Arg Ala Thr Val
1               5

<210> SEQ ID NO 257
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 257

Phe Ala Asn Asn Lys Phe Thr Leu Val
1               5

<210> SEQ ID NO 258
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 258

Leu Leu His Thr Asp Phe Glu Gln Val
1               5
```

<210> SEQ ID NO 259
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 259

Phe Leu Tyr Glu Leu Ile Trp Asn Val
1               5

<210> SEQ ID NO 260
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 260

Leu Leu Cys Gly Asn Leu Leu Ile Leu
1               5

<210> SEQ ID NO 261
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 261

Leu Ile Asp Gln Tyr Leu Tyr Tyr Leu
1               5

<210> SEQ ID NO 262
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 262

Leu Leu Tyr Asn Cys Cys Tyr His Val
1               5

<210> SEQ ID NO 263
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 263

Arg Asp Val Pro Met Leu Ile Thr Thr

```
1               5

<210> SEQ ID NO 264
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 264

Pro Glu Ser Ser Gln Arg Pro Pro Leu
1               5

<210> SEQ ID NO 265
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 265

Leu Met Gly Asp Lys Ser Glu Asn Val
1               5

<210> SEQ ID NO 266
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 266

Arg Leu Asn Glu Leu Leu Ala Tyr Val
1               5

<210> SEQ ID NO 267
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 267

Arg Leu Trp His Tyr Pro Cys Thr Ile
1               5

<210> SEQ ID NO 268
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 268
```

Leu Leu Met Trp Glu Ala Val Thr Val
1               5

<210> SEQ ID NO 269
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 269

Gly Met Leu Gly Phe Val Phe Thr Leu
1               5

<210> SEQ ID NO 270
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 270

Leu Gly Tyr Gly Phe Val Asn Tyr Ile
1               5

<210> SEQ ID NO 271
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 271

Leu Ile Val Asp Ala Val Leu Gln Leu
1               5

<210> SEQ ID NO 272
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 272

Phe Leu Leu Asp Ile Leu Gly Ala Thr
1               5

<210> SEQ ID NO 273
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 273

```
Arg Leu Leu Gln Thr Gly Ile His Val
1               5

<210> SEQ ID NO 274
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 274

Phe Leu Gly Glu Arg Val Thr Leu Thr
1               5

<210> SEQ ID NO 275
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 275

Phe Val Asn Tyr Asp Phe Thr Ile Val
1               5

<210> SEQ ID NO 276
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 276

Lys Leu Asn Asp Trp Asp Phe Val Val
1               5

<210> SEQ ID NO 277
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 277

Leu Phe Leu Asn Thr Leu Ser Phe Val
1               5

<210> SEQ ID NO 278
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm
```

```
<400> SEQUENCE: 278

Gly Gly Asn Gly Met Leu Ala Thr Ile
1               5

<210> SEQ ID NO 279
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 279

Ser Phe His Ser Leu His Leu Leu Phe
1               5

<210> SEQ ID NO 280
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 280

Ala Ile Ile Ile Ala Val Leu Leu Val
1               5

<210> SEQ ID NO 281
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 281

Arg Phe Ile Ala Gln Leu Leu Leu Leu
1               5

<210> SEQ ID NO 282
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 282

Ser Ile Tyr Val Tyr Ala Leu Pro Leu
1               5

<210> SEQ ID NO 283
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm
```

```
<400> SEQUENCE: 283

Pro Thr Leu Asp Lys Val Leu Glu Val
1               5

<210> SEQ ID NO 284
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 284

Leu Val Leu Ile Leu Tyr Leu Cys Val
1               5

<210> SEQ ID NO 285
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 285

Gly Met Ser Arg Ile Gly Met Glu Val
1               5

<210> SEQ ID NO 286
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 286

Phe Leu Ser His Asp Phe Thr Leu Val
1               5

<210> SEQ ID NO 287
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 287

Cys Ile Asn Gly Val Cys Trp Ser Val
1               5

<210> SEQ ID NO 288
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
```

```
             TCR-binding algorithm

<400> SEQUENCE: 288

Ser Ile Thr Glu Val Glu Cys Phe Leu
1               5

<210> SEQ ID NO 289
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 289

Arg Leu Glu Arg Lys Trp Leu Asp Val
1               5

<210> SEQ ID NO 290
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 290

Ser Ile Asp Gln Leu Cys Lys Thr Phe
1               5

<210> SEQ ID NO 291
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 291

Gln Leu Phe Asn His Thr Met Phe Ile
1               5

<210> SEQ ID NO 292
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 292

Met Ile Met Gln Gly Gly Phe Ser Val
1               5

<210> SEQ ID NO 293
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

<223> OTHER INFORMATION: Immunogenic peptide used for developing the
       TCR-binding algorithm

<400> SEQUENCE: 293

Lys Cys Ile Asp Phe Tyr Ser Arg Ile
1               5

<210> SEQ ID NO 294
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
       TCR-binding algorithm

<400> SEQUENCE: 294

Ser Leu Lys Lys Asn Ser Arg Ser Leu
1               5

<210> SEQ ID NO 295
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
       TCR-binding algorithm

<400> SEQUENCE: 295

Met Leu Asp Leu Gln Pro Glu Thr Thr
1               5

<210> SEQ ID NO 296
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
       TCR-binding algorithm

<400> SEQUENCE: 296

Met Thr Ile Ile Phe Leu Ile Leu Met
1               5

<210> SEQ ID NO 297
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
       TCR-binding algorithm

<400> SEQUENCE: 297

Asn Asp Phe Cys Cys Val Ala Thr Val
1               5

<210> SEQ ID NO 298
<211> LENGTH: 9
<212> TYPE: PRT
<213> ORGANISM: Homo sapiens
<220> FEATURE:
<221> NAME/KEY: PEPTIDE

```
<222> LOCATION: (1)..(9)
<223> OTHER INFORMATION: Immunogenic peptide used for developing the
      TCR-binding algorithm

<400> SEQUENCE: 298

Tyr Leu Glu Pro Gly Pro Val Thr Ala
1               5

<210> SEQ ID NO 299
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 299

Ile Leu Asp Lys Lys Val Glu Lys Val
1               5

<210> SEQ ID NO 300
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 300

Leu Ala Leu Leu Leu Leu Asp Arg Leu
1               5

<210> SEQ ID NO 301
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 301

Phe Ile Asp Lys Phe Thr Pro Pro Val
1               5

<210> SEQ ID NO 302
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 302

Gly Ile Leu Glu Phe Val Phe Thr Leu
1               5

<210> SEQ ID NO 303
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 303

Tyr Leu Val Ser Ile Phe Leu His Leu
1               5

<210> SEQ ID NO 304
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 304

Phe Val Val Pro Ile Leu Leu Lys Ala
1               5

<210> SEQ ID NO 305
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 305

Cys Leu Pro Ala Cys Val Tyr Gly Leu
1               5

<210> SEQ ID NO 306
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 306

Val Leu Ser Glu Trp Leu Pro Val Thr
1               5

<210> SEQ ID NO 307
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 307

Thr Leu Leu Asp His Ile Arg Thr Ala
1               5

<210> SEQ ID NO 308
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 308

Lys Met Leu Lys Glu Met Gly Glu Val
1               5

<210> SEQ ID NO 309
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 309

Ala Val Ala Asp His Val Ala Ala Val
1               5

<210> SEQ ID NO 310
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 310

Thr Leu Asn Asp Leu Glu Thr Asp Val
1               5

<210> SEQ ID NO 311
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 311

Thr Leu Leu Ala Asn Val Thr Ala Val
1               5

<210> SEQ ID NO 312
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 312

Ser Leu Val Asn Gly Val Val Arg Leu
1               5

<210> SEQ ID NO 313
<211> LENGTH: 9
<212> TYPE: PRT
```

```
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 313

Ala Leu Pro His Ile Ile Asp Glu Val
1               5

<210> SEQ ID NO 314
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 314

Leu Ile Thr Gly Arg Leu Gln Ser Leu
1               5

<210> SEQ ID NO 315
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 315

Thr Leu Thr Ser Tyr Trp Arg Arg Val
1               5

<210> SEQ ID NO 316
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 316

Phe Gln Gly Arg Gly Val Phe Glu Leu
1               5

<210> SEQ ID NO 317
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 317

Ser Leu Met Asp Leu Leu Ser Ser Leu
1               5

<210> SEQ ID NO 318
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 318

Phe Leu Thr Ser Val Ile Asn Arg Val
1               5

<210> SEQ ID NO 319
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 319

Gly Ile Leu Asp Phe Gly Val Lys Leu
1               5

<210> SEQ ID NO 320
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 320

Gln Leu Val Gln Ser Gly Ala Glu Val
1               5

<210> SEQ ID NO 321
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 321

Tyr Leu Leu Lys Pro Val Gln Arg Ile
1               5

<210> SEQ ID NO 322
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 322

Ser Leu Pro Ile Thr Val Tyr Tyr Ala
1               5

<210> SEQ ID NO 323
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 323

Ala Ile Met Asp Lys Asn Ile Thr Leu
1               5

<210> SEQ ID NO 324
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 324

Arg Ile Asn Ala Ile Leu Ala Thr Ala
1               5

<210> SEQ ID NO 325
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 325

Phe Val Asn His Arg Phe Thr Leu Val
1               5

<210> SEQ ID NO 326
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 326

Leu Leu Ser Leu Phe Ser Leu Trp Leu
1               5

<210> SEQ ID NO 327
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 327

Ala Leu Ala Glu Gly Asp Leu Leu Ala
1               5
```

```
<210> SEQ ID NO 328
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 328

Thr Leu Ala Arg Gly Phe Pro Phe Val
1               5

<210> SEQ ID NO 329
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 329

Leu Ile Phe Leu Ala Arg Ser Ala Leu
1               5

<210> SEQ ID NO 330
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 330

Ile Leu Leu Trp Glu Ile Pro Asp Val
1               5

<210> SEQ ID NO 331
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 331

His Leu Met Ile Asp Arg Pro Tyr Val
1               5

<210> SEQ ID NO 332
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 332

Ala Leu Ile Ser Ala Phe Ser Gly Ser
1               5
```

<210> SEQ ID NO 333
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 333

Arg Gln Tyr Asp Pro Val Ala Ala Leu
1               5

<210> SEQ ID NO 334
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 334

Leu Leu Ile Gly Gly Phe Ala Gly Leu
1               5

<210> SEQ ID NO 335
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 335

Phe Ala Asn Tyr Lys Phe Thr Leu Val
1               5

<210> SEQ ID NO 336
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 336

Val Pro Ile Leu Leu Lys Ala Leu Tyr
1               5

<210> SEQ ID NO 337
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 337

Leu Leu Trp Asn Gly Pro Met Ala Val
1               5

```
<210> SEQ ID NO 338
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 338

Lys Leu Ser Asp Tyr Glu Gly Arg Leu
1               5

<210> SEQ ID NO 339
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 339

Gly Met Val Thr Thr Ser Thr Thr Leu
1               5

<210> SEQ ID NO 340
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 340

Ser Leu Val Glu Glu Leu Lys Lys Val
1               5

<210> SEQ ID NO 341
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 341

Ala Leu Ser Ala Leu Leu Thr Lys Leu
1               5

<210> SEQ ID NO 342
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 342

Phe Val Asp Tyr Asn Phe Ser Leu Val
```

-continued

```
<210> SEQ ID NO 343
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 343

Ile Leu Leu Asn Lys His Ile Asp Ala
1               5

<210> SEQ ID NO 344
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 344

Ile Leu Asn Asn Pro Lys Ala Ser Leu
1               5

<210> SEQ ID NO 345
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 345

Phe Gln Gln Leu Phe Leu Asn Thr Leu
1               5

<210> SEQ ID NO 346
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 346

Ala Leu Leu Gly Leu Thr Leu Gly Val
1               5

<210> SEQ ID NO 347
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 347
```

```
Gly Leu Met Trp Leu Ser Tyr Phe Val
1               5

<210> SEQ ID NO 348
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 348

Lys Val Asp Asp Thr Phe Tyr Tyr Val
1               5

<210> SEQ ID NO 349
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 349

Ala Leu Phe His Glu Val Ala Lys Leu
1               5

<210> SEQ ID NO 350
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 350

Ser Leu Pro Arg Ser Arg Thr Pro Ile
1               5

<210> SEQ ID NO 351
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 351

Leu Met Leu Ile Trp Tyr Arg Pro Val
1               5

<210> SEQ ID NO 352
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 352
```

Ile Val Ile Glu Ala Ile His Thr Val
1               5

<210> SEQ ID NO 353
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 353

Ser Leu Ile Leu Val Ser Gln Tyr Thr
1               5

<210> SEQ ID NO 354
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 354

Gly Thr Leu Gly Phe Val Phe Thr Leu
1               5

<210> SEQ ID NO 355
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 355

Arg Leu Asn Glu Val Ala Lys Asn Leu
1               5

<210> SEQ ID NO 356
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 356

Met Ile Asn Ala Tyr Leu Asp Lys Leu
1               5

<210> SEQ ID NO 357
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

```
<400> SEQUENCE: 357

Thr Ile Asp Gln Leu Cys Lys Thr Phe
1               5

<210> SEQ ID NO 358
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 358

Leu Val Leu Pro Ile Leu Ile Thr Ile
1               5

<210> SEQ ID NO 359
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 359

Ala Ile Val Asp Lys Asn Ile Thr Leu
1               5

<210> SEQ ID NO 360
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 360

Arg Leu Ile Gln Asn Ser Ile Thr Ile
1               5

<210> SEQ ID NO 361
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 361

Ile Leu Arg Ser Phe Ile Pro Leu Leu
1               5

<210> SEQ ID NO 362
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm
```

```
<400> SEQUENCE: 362

Phe Ala Asn His Asn Phe Thr Leu Val
1               5

<210> SEQ ID NO 363
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 363

Gln Leu Ser Thr Arg Gly Val Gln Ile
1               5

<210> SEQ ID NO 364
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 364

Leu Leu Ser Ile Leu Cys Ile Trp Val
1               5

<210> SEQ ID NO 365
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 365

Pro Thr Leu Asp Lys Val Leu Glu Leu
1               5

<210> SEQ ID NO 366
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 366

Gly Val Arg Val Leu Glu Asp Gly Val
1               5

<210> SEQ ID NO 367
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
```

```
                TCR-binding algorithm

<400> SEQUENCE: 367

Met Val Met Glu Leu Ile Arg Met Ile
1               5

<210> SEQ ID NO 368
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 368

Ser Ala Pro Leu Pro Ser Asn Arg Val
1               5

<210> SEQ ID NO 369
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 369

Leu Gln Leu Cys Cys Leu Ala Thr Ala
1               5

<210> SEQ ID NO 370
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 370

Glu Leu Thr Glu Val Phe Glu Phe Ala
1               5

<210> SEQ ID NO 371
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 371

Cys Leu Thr Glu Tyr Ile Leu Trp Val
1               5

<210> SEQ ID NO 372
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

```
<223> OTHER INFORMATION: Immunogenic peptide used for developing the
      TCR-binding algorithm

<400> SEQUENCE: 372

Tyr Leu Ile Ile Gly Ile Leu Thr Leu
1               5

<210> SEQ ID NO 373
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 373

Gly Ile Leu Gly Leu Val Phe Thr Leu
1               5

<210> SEQ ID NO 374
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 374

Ala Met Leu Asn Gly Leu Ile Tyr Val
1               5

<210> SEQ ID NO 375
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 375

Arg Met Leu Pro His Ala Pro Gly Val
1               5

<210> SEQ ID NO 376
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 376

Leu Leu Ile Asp Leu Thr Ser Phe Leu
1               5

<210> SEQ ID NO 377
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)
<223> OTHER INFORMATION: Immunogenic peptide used for developing the
      TCR-binding algorithm

<400> SEQUENCE: 377

Leu Leu Leu Gly Thr Leu Asn Ile Val
1               5

<210> SEQ ID NO 378
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 378

Phe Ala Asn Tyr Asn Phe Thr Leu Val
1               5

<210> SEQ ID NO 379
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 379

Leu Gly Tyr Gly Phe Val Asn Tyr Val
1               5

<210> SEQ ID NO 380
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 380

Thr Leu Ala Cys Phe Ala Val Tyr Thr
1               5

<210> SEQ ID NO 381
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 381

Ser Leu Asn Gln Thr Val His Ser Leu
1               5

<210> SEQ ID NO 382
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 382

Arg Leu Asn Thr Val Leu Ala Thr Ala
1               5

<210> SEQ ID NO 383
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 383

Ile Val Ser Pro Phe Ile Pro Leu Leu
1               5

<210> SEQ ID NO 384
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 384

Leu Leu Ile Glu Gly Ile Phe Phe Ile
1               5

<210> SEQ ID NO 385
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 385

Ser Ile Val Ala Tyr Thr Met Ser Leu
1               5

<210> SEQ ID NO 386
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 386

Glu Leu Leu Arg Pro Thr Thr Leu Val
1               5

<210> SEQ ID NO 387
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 387

Phe Ala Phe Lys Asp Leu Phe Val Val
1               5

<210> SEQ ID NO 388
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 388

Asn Ile Val Cys Pro Leu Cys Thr Leu
1               5

<210> SEQ ID NO 389
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 389

Gly Gly Pro Asn Leu Asp Asn Ile Leu
1               5

<210> SEQ ID NO 390
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 390

Thr Ile Pro Glu Ala Leu Ala Ala Val
1               5

<210> SEQ ID NO 391
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 391

Thr Leu Leu Tyr Val Leu Phe Glu Val
1               5

<210> SEQ ID NO 392
<211> LENGTH: 9
<212> TYPE: PRT
```

```
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 392

Phe Leu Tyr Gly Ala Leu Leu Leu Ala
1               5

<210> SEQ ID NO 393
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 393

Leu Leu Asp Val Ala Pro Leu Ser Leu
1               5

<210> SEQ ID NO 394
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 394

Met Gly Leu Pro Gly Val Ala Thr Val
1               5

<210> SEQ ID NO 395
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 395

Phe Ala Asn Cys Asn Phe Thr Leu Val
1               5

<210> SEQ ID NO 396
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 396

Asn Leu Asn Glu Ser Leu Ile Asp Leu
1               5

<210> SEQ ID NO 397
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 397

Leu Leu Trp Ser Tyr Ala Met Gly Val
1               5

<210> SEQ ID NO 398
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 398

Phe Met Val Phe Leu Gln Thr His Ile
1               5

<210> SEQ ID NO 399
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 399

Arg Val Asn Arg Leu Ile Ile Trp Val
1               5

<210> SEQ ID NO 400
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 400

Ser Leu Met Ser Gly Val Glu Pro Leu
1               5

<210> SEQ ID NO 401
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 401

Thr Leu Asp Tyr Lys Pro Leu Ser Val
1               5

<210> SEQ ID NO 402
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 402

Ser Leu Phe Asn Thr Val Ala Thr Leu
1               5

<210> SEQ ID NO 403
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 403

Val Leu Leu Arg His Ser Lys Asn Val
1               5

<210> SEQ ID NO 404
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 404

Val Leu Leu Cys Val Cys Leu Leu Ile
1               5

<210> SEQ ID NO 405
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 405

Ser Leu Leu Met Trp Ile Thr Gln Cys
1               5

<210> SEQ ID NO 406
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 406

Gly Leu Asn Asp Tyr Leu His Ser Val
1               5
```

```
<210> SEQ ID NO 407
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 407

Ala Met Ala Ser Thr Glu Gly Asn Val
1               5

<210> SEQ ID NO 408
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 408

Gly Leu Arg Glu Asp Leu Leu Ser Leu
1               5

<210> SEQ ID NO 409
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 409

Lys Leu Trp Cys Arg His Phe Cys Val
1               5

<210> SEQ ID NO 410
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 410

Ala Leu Ala Ile Ile Ile Ala Val Leu
1               5

<210> SEQ ID NO 411
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 411

Leu Gln Leu Pro Gln Gly Thr Thr Leu
1               5
```

<210> SEQ ID NO 412
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 412

Phe Leu Trp Glu Asp Gln Thr Leu Leu
1               5

<210> SEQ ID NO 413
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 413

Phe Leu Leu Lys Leu Thr Pro Leu Leu
1               5

<210> SEQ ID NO 414
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 414

Gly Ile Trp Gly Phe Val Phe Thr Leu
1               5

<210> SEQ ID NO 415
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 415

Phe Ala Asn His Lys Phe Thr Leu Val
1               5

<210> SEQ ID NO 416
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 416

Gln Met Met Arg Asn Glu Phe Arg Val
1               5

<210> SEQ ID NO 417
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 417

Phe Leu Leu Cys Phe Cys Val Leu Leu
1               5

<210> SEQ ID NO 418
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 418

Gly Ile Leu Thr Val Ser Val Ala Val
1               5

<210> SEQ ID NO 419
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 419

Phe Val Asp Tyr Asn Phe Thr Ile Val
1               5

<210> SEQ ID NO 420
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 420

Ala Leu Tyr Asp Val Val Ser Lys Leu
1               5

<210> SEQ ID NO 421
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 421

Leu Phe Ala Ala Phe Pro Ser Phe Ala

```
<210> SEQ ID NO 422
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 422

Leu Leu Gly Arg Asn Ser Phe Glu Val
1               5

<210> SEQ ID NO 423
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 423

Met Leu Leu Asp Lys Asn Ile Pro Ile
1               5

<210> SEQ ID NO 424
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 424

Met Leu Trp Gly Tyr Leu Gln Tyr Val
1               5

<210> SEQ ID NO 425
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 425

Asn Leu Leu Thr Thr Pro Lys Phe Thr
1               5

<210> SEQ ID NO 426
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 426
```

```
Thr Leu Tyr Ala Val Ala Thr Thr Ile
1               5

<210> SEQ ID NO 427
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 427

Phe Leu Lys Gln Gln Tyr Met Asn Leu
1               5

<210> SEQ ID NO 428
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 428

Lys Asp Leu Val Leu Leu Ala Thr Ile
1               5

<210> SEQ ID NO 429
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 429

Leu Leu Val Ser Glu Ile Asp Trp Leu
1               5

<210> SEQ ID NO 430
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 430

Lys Leu Asn Pro Met Leu Ala Lys Ala
1               5

<210> SEQ ID NO 431
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 431
```

Val Ile Phe Asp Phe Leu His Cys Ile
1               5

<210> SEQ ID NO 432
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 432

Phe Ala Asn Asn Glu Phe Thr Leu Val
1               5

<210> SEQ ID NO 433
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 433

Val Leu Cys Leu Arg Pro Val Gly Ala
1               5

<210> SEQ ID NO 434
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 434

Ser Leu Phe Leu Gly Ile Leu Ser Val
1               5

<210> SEQ ID NO 435
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 435

Ala Leu Ala His Gly Val Arg Ala Leu
1               5

<210> SEQ ID NO 436
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

```
<400> SEQUENCE: 436

Ala Leu Leu Ala Leu Thr Arg Ala Ile
1               5

<210> SEQ ID NO 437
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 437

Asn Leu Leu Ile Arg Cys Leu Arg Cys
1               5

<210> SEQ ID NO 438
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 438

Ser Met Ile Asn Gly Val Val Lys Leu
1               5

<210> SEQ ID NO 439
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 439

Asp Val Ser Arg Pro Thr Ala Val Val
1               5

<210> SEQ ID NO 440
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 440

Ala Leu Asn Thr Leu Val Lys Gln Leu
1               5

<210> SEQ ID NO 441
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm
```

```
<400> SEQUENCE: 441

Phe Ile Ala Gly Leu Ile Ala Ile Val
1               5

<210> SEQ ID NO 442
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 442

Lys Thr Trp Gly Gln Tyr Trp Gln Val
1               5

<210> SEQ ID NO 443
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 443

Arg Met Ser Lys Gly Val Phe Lys Val
1               5

<210> SEQ ID NO 444
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 444

Ile Leu Tyr Gly Pro Leu Thr Arg Ile
1               5

<210> SEQ ID NO 445
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 445

His Leu Ser Leu Arg Gly Leu Pro Val
1               5

<210> SEQ ID NO 446
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
```

```
                        TCR-binding algorithm

<400> SEQUENCE: 446

Ser Leu Phe Gly Gly Met Ser Trp Ile
1               5

<210> SEQ ID NO 447
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 447

Leu Leu Leu Leu Asp Val Ala Pro Leu
1               5

<210> SEQ ID NO 448
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 448

Phe Leu Met Glu Asp Gln Thr Leu Leu
1               5

<210> SEQ ID NO 449
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 449

Ala Met Asp Ser Asn Thr Leu Glu Leu
1               5

<210> SEQ ID NO 450
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 450

Ile Thr Asn Cys Leu Leu Ser Thr Ala
1               5

<210> SEQ ID NO 451
<211> LENGTH: 9
<212> TYPE: PRT
<213> ORGANISM: Homo sapiens
<220> FEATURE:
<221> NAME/KEY: PEPTIDE
<222> LOCATION: (1)..(9)
```

<223> OTHER INFORMATION: Immunogenic peptide used for developing the
      TCR-binding algorithm

<400> SEQUENCE: 451

Ile Leu Ile Glu Gly Ile Phe Phe Ala
1               5

<210> SEQ ID NO 452
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 452

Asp Leu Met Gly Tyr Ile Pro Ala Val
1               5

<210> SEQ ID NO 453
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 453

Ala Met Leu Val Leu Leu Ala Glu Ile
1               5

<210> SEQ ID NO 454
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 454

Met Ile Asn Pro Leu Val Ile Thr Thr
1               5

<210> SEQ ID NO 455
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 455

Phe Ile Leu Pro Val Leu Gly Ala Val
1               5

<210> SEQ ID NO 456
<211> LENGTH: 10
<212> TYPE: PRT
<213> ORGANISM: Homo sapiens
<220> FEATURE:
<221> NAME/KEY: PEPTIDE

```
<222> LOCATION: (1)..(9)
<223> OTHER INFORMATION: Immunogenic peptide used for developing the
      TCR-binding algorithm

<400> SEQUENCE: 456

Ser Phe Ala Phe Arg Asp Leu Cys Ile Val
1               5                   10

<210> SEQ ID NO 457
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 457

Arg Met Phe Pro Asn Ala Pro Tyr Leu
1               5

<210> SEQ ID NO 458
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 458

Lys Val Leu Ile Arg Cys Tyr Leu Cys
1               5

<210> SEQ ID NO 459
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 459

Lys Leu Ile Val Thr Pro Ala Ala Leu
1               5

<210> SEQ ID NO 460
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 460

Val Leu Gln Glu Leu Asn Val Thr Val
1               5

<210> SEQ ID NO 461
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 461

Leu Leu Asn Tyr Ile Leu Lys Ser Val
1               5

<210> SEQ ID NO 462
<211> LENGTH: 9
<212> TYPE: PRT
<213> ORGANISM: Homo sapiens
<220> FEATURE:
<221> NAME/KEY: PEPTIDE
<222> LOCATION: (1)..(9)

<400> SEQUENCE: 462

Met Met Phe Gly Phe His His Ser Val
1               5

<210> SEQ ID NO 463
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 463

Ile Val Leu Gly Leu Ile Ala Thr Ala
1               5

<210> SEQ ID NO 464
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 464

Tyr Leu Asn Lys Ile Gln Asn Ser Leu
1               5

<210> SEQ ID NO 465
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 465

Gln Leu Leu Ser Ser Ser Lys Tyr Thr
1               5

<210> SEQ ID NO 466
<211> LENGTH: 9
<212> TYPE: PRT
<213> ORGANISM: Homo sapiens
<220> FEATURE:
<221> NAME/KEY: PEPTIDE
```

```
<222> LOCATION: (1)..(9)
<223> OTHER INFORMATION: Immunogenic peptide used for developing the
      TCR-binding algorithm

<400> SEQUENCE: 466

Cys Leu Phe Lys Asp Trp Glu Glu Leu
1               5

<210> SEQ ID NO 467
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 467

Ala Ile Ile Asp Pro Leu Ile Tyr Ala
1               5

<210> SEQ ID NO 468
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 468

Thr Leu Gly Ile Val Cys Pro Ile Cys
1               5

<210> SEQ ID NO 469
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 469

Lys Tyr Gln Glu Phe Phe Trp Asp Ala
1               5

<210> SEQ ID NO 470
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 470

Leu Ala Leu Pro Met Pro Ala Thr Ala
1               5

<210> SEQ ID NO 471
<211> LENGTH: 9
<212> TYPE: PRT
<213> ORGANISM: Homo sapiens
<220> FEATURE:
```

```
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 471

Ser Leu Met Ser Trp Ser Ala Ile Leu
1               5

<210> SEQ ID NO 472
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 472

Lys Val Leu Gly Leu Trp Ala Thr Val
1               5

<210> SEQ ID NO 473
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 473

Ile Leu Pro Asp Pro Leu Lys Pro Thr
1               5

<210> SEQ ID NO 474
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 474

Phe Leu Ser Phe Ala Ser Leu Phe Leu
1               5

<210> SEQ ID NO 475
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 475

Ile Leu Ile Glu Gly Val Phe Phe Ala
1               5

<210> SEQ ID NO 476
<211> LENGTH: 9
<212> TYPE: PRT
<213> ORGANISM: Homo sapiens
```

```
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 476

Ala Leu Leu Glu Asp Pro Val Gly Thr
1               5

<210> SEQ ID NO 477
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 477

Phe Val Asn Tyr Asn Phe Thr Leu Val
1               5

<210> SEQ ID NO 478
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 478

Trp Gln Trp Glu His Ile Pro Pro Ala
1               5

<210> SEQ ID NO 479
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 479

Val Met Leu Phe Ile Leu Ala Gly Leu
1               5

<210> SEQ ID NO 480
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 480

Met Thr Tyr Ala Ala Pro Leu Phe Val
1               5

<210> SEQ ID NO 481
<211> LENGTH: 9
<212> TYPE: PRT
```

```
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 481

Tyr Leu Lys Lys Ile Lys Asn Ser Leu
1               5

<210> SEQ ID NO 482
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 482

Ala Met Ala Gly Ala Ser Thr Ser Ala
1               5

<210> SEQ ID NO 483
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 483

Asn Met Leu Ser Thr Val Leu Gly Val
1               5

<210> SEQ ID NO 484
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 484

Ile Leu Ala Lys Phe Leu His Trp Leu
1               5

<210> SEQ ID NO 485
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 485

Lys Leu Gly Pro Gly Glu Glu Gln Val
1               5

<210> SEQ ID NO 486
<211> LENGTH: 9
```

```
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 486

Ser Val Tyr Asp Phe Phe Val Trp Leu
1               5

<210> SEQ ID NO 487
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 487

Val Leu Thr Ser Glu Ser Met His Val
1               5

<210> SEQ ID NO 488
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 488

Ser Leu Ser Arg Phe Ser Trp Gly Ala
1               5

<210> SEQ ID NO 489
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 489

Arg Met Leu Gly Asp Val Met Ala Val
1               5

<210> SEQ ID NO 490
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 490

Tyr Ile Leu Glu Glu Thr Ser Val Met
1               5

<210> SEQ ID NO 491
```

```
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 491

Ile Leu Asp Ala His Ser Leu Tyr Leu
1               5

<210> SEQ ID NO 492
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 492

Gly Ile Phe Glu Asp Arg Ala Pro Val
1               5

<210> SEQ ID NO 493
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 493

Thr Val Cys Gly Gly Ile Met Phe Leu
1               5

<210> SEQ ID NO 494
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 494

Gly Leu Cys Pro His Cys Ile Asn Val
1               5

<210> SEQ ID NO 495
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 495

Ala Phe Leu Gly Glu Arg Val Thr Leu
1               5
```

-continued

```
<210> SEQ ID NO 496
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 496

Asn Gly Val Arg Val Leu Ala Thr Ala
1               5

<210> SEQ ID NO 497
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 497

Gln Leu Leu Asn Ser Val Leu Thr Leu
1               5

<210> SEQ ID NO 498
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 498

Ile Leu His Thr Asn Met Pro Asn Val
1               5

<210> SEQ ID NO 499
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 499

Ala Ile Thr Glu Val Glu Cys Phe Leu
1               5

<210> SEQ ID NO 500
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 500

Gly Met Asp Pro Arg Met Cys Ser Leu
1               5
```

<210> SEQ ID NO 501
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 501

Ala Ile Leu Ile Arg Val Arg Asn Ala
1               5

<210> SEQ ID NO 502
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 502

Lys Thr Val Leu Glu Leu Thr Glu Val
1               5

<210> SEQ ID NO 503
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 503

Val Leu His Lys Arg Thr Leu Gly Leu
1               5

<210> SEQ ID NO 504
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 504

Met Gly Asn Gly Cys Leu Arg Ile Val
1               5

<210> SEQ ID NO 505
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 505

Leu Val Met Ala Gln Leu Leu Arg Ile
1               5

```
<210> SEQ ID NO 506
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 506

Ala Met Leu Asp Leu Leu Lys Ser Val
1               5

<210> SEQ ID NO 507
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 507

Ile Ala Asp Ala Ala Leu Ala Ala Leu
1               5

<210> SEQ ID NO 508
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 508

Asp Leu Ser Leu Arg Arg Phe Met Val
1               5

<210> SEQ ID NO 509
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 509

Leu Gln Asp Ile Glu Ile Thr Cys Val
1               5

<210> SEQ ID NO 510
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 510

Lys Leu Gln Glu Gln Gln Ser Asp Leu
```

-continued

```
<210> SEQ ID NO 511
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 511

Phe Leu Thr Cys Thr Asp Arg Ser Val
1               5

<210> SEQ ID NO 512
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: Immunogenic peptide used for developing the
      TCR-binding algorithm

<400> SEQUENCE: 512

Ser Val Gly Gly Val Phe Thr Ser Val
1               5

<210> SEQ ID NO 513
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: immunogenic peptides from the mutations in head
      and neck cancer

<400> SEQUENCE: 513

Ser Thr Arg Asp Pro Leu Ser Lys Ile
1               5

<210> SEQ ID NO 514
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: immunogenic peptides from the mutations in head
      and neck cancer

<400> SEQUENCE: 514

Arg Leu Leu Ile Glu Leu Ile Trp Lys
1               5

<210> SEQ ID NO 515
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: immunogenic peptides from the mutations in head
      and neck cancer

<400> SEQUENCE: 515
```

```
Ser Thr Val Glu Ser Leu Thr Ser Gln
1               5

<210> SEQ ID NO 516
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: immunogenic peptides from the mutations in head
      and neck cancer

<400> SEQUENCE: 516

Leu Leu Ile Glu Leu Ile Trp Lys Arg
1               5

<210> SEQ ID NO 517
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: immunogenic peptides from the mutations in head
      and neck cancer

<400> SEQUENCE: 517

Leu Ile Glu Leu Ile Trp Lys Arg Glu
1               5

<210> SEQ ID NO 518
<211> LENGTH: 9
<212> TYPE: PRT
<213> ORGANISM: Homo sapiens
<220> FEATURE:
<221> NAME/KEY: PEPTIDE
<222> LOCATION: (1)..(9r)
<223> OTHER INFORMATION: immunogenic peptides from the mutations in head
      and neck cancer

<400> SEQUENCE: 518

Lys Ile Thr Glu Gln Glu Lys Asp Phe
1               5

<210> SEQ ID NO 519
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: immunogenic peptides from the mutations in head
      and neck cancer

<400> SEQUENCE: 519

Leu Thr Ser Gln Arg Lys Glu Met Lys
1               5
```